United States Patent
Kakizuka et al.

(10) Patent No.: US 9,931,351 B2
(45) Date of Patent: Apr. 3, 2018

(54) METHOD FOR IMPROVING LEPTIN RESISTANCE

(71) Applicant: Kyoto University, Kyoto (JP)

(72) Inventors: Akira Kakizuka, Takatsuki (JP); Ken Ebihara, Shimotsuke (JP); Megumi Abe, Kyoto (JP); Chihiro Ebihara, Shimotsuke (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 14/916,085

(22) PCT Filed: Sep. 3, 2014

(86) PCT No.: PCT/JP2014/073256
§ 371 (c)(1),
(2) Date: Jun. 16, 2016

(87) PCT Pub. No.: WO2015/033981
PCT Pub. Date: Mar. 12, 2015

(65) Prior Publication Data
US 2016/0303144 A1    Oct. 20, 2016

(30) Foreign Application Priority Data
Sep. 4, 2013   (JP) .................................. 2013-183265

(51) Int. Cl.
| | |
|---|---|
| *A61K 31/655* | (2006.01) |
| *C07D 213/76* | (2006.01) |
| *C07D 409/04* | (2006.01) |
| *A61K 45/06* | (2006.01) |
| *C07C 245/10* | (2006.01) |

(52) U.S. Cl.
CPC ............ *A61K 31/655* (2013.01); *A61K 45/06* (2013.01); *C07C 245/10* (2013.01); *C07D 213/76* (2013.01); *C07D 409/04* (2013.01)

(58) Field of Classification Search
CPC .......................... A61K 31/655; C07C 245/10
See application file for complete search history.

(56) References Cited

U.S. PATENT DOCUMENTS

| | | | |
|---|---|---|---|
| 2013/0184241 A1* | 7/2013 | Kakizuka | ............. C07C 309/47 514/150 |
| 2014/0024661 A1 | 1/2014 | Zhou et al. | |
| 2014/0148416 A1 | 5/2014 | Kakizuka et al. | |
| 2016/0000810 A1 | 1/2016 | Kakizuka et al. | |

FOREIGN PATENT DOCUMENTS

| | | |
|---|---|---|
| WO | 00/50414 A1 | 8/2000 |
| WO | 2007/041282 A2 | 4/2007 |
| WO | 2012/014994 A1 | 2/2012 |
| WO | 2012/043891 A1 | 4/2012 |
| WO | 2014/129495 A1 | 8/2014 |

OTHER PUBLICATIONS

Könner et al., "Selective Insulin and Leptin Resistance in Metabolic Disorders," Cell Metabolism, 16: 144-152 (2012).
Morris et al., "Recent advances in understanding leptin signaling and leptin resistance," American Journal of Physiology Endocrinology and Metabolism, 297: E1247-E1259 (2009).
Ogawa et al., "Increased Glucose Metabolism and Insulin Sensitivity in Transgenic Skinny Mice Overexpressing Leptin," Diabetes, 48: 1822-1829 (1999).
Zhang et al., "Positional cloning of the mouse obese gene and its human homologue," Nature, 372: 425-432 (1994).
Moitra et al., "Life without white fat: a transgenic mouse," Genes & Development, 12: 3168-3181 (1998).
Aizawa-Abe et al., "Generation of leptin-deficient Lepmkyo/Lepmkyo rats and identification of leptin-responsive genes in the liver," Physiological Genomics, 45: 786-793 (2013).
International Preliminary Report on Patentability and Written Opinion issued in corresponding International Patent Application No. PCT/JP2014/073256 dated Nov. 18, 2014.
International Search Report issued in corresponding International Patent Application No. PCT/JP2014/073256 dated Nov. 18, 2014.
Extended European Search Report issued in corresponding European Patent Application No. 14843063.0 dated Feb. 28, 2017.

* cited by examiner

*Primary Examiner* — Sudhakar Katakam
(74) *Attorney, Agent, or Firm* — Morgan, Lewis & Bockius LLP

(57) ABSTRACT

The present invention provides a compound of formula (I) which improves leptin resistance, a pharmaceutical composition comprising the compound, a method for manufacturing a pharmaceutical for improving leptin resistance comprising using the compound, use of the compound for manufacturing a pharmaceutical for improving leptin resistance, and a method for improving leptin resistance comprising administering the compound or the pharmaceutical composition. The improvement of leptin resistance can lead treatment and/or prevention of a disorder associated with leptin resistance, including, particularly, metabolic disorder, obesity, hyperphagia, steatosis, diabetes, and dyslipidemia.

20 Claims, 28 Drawing Sheets

Fig. 1
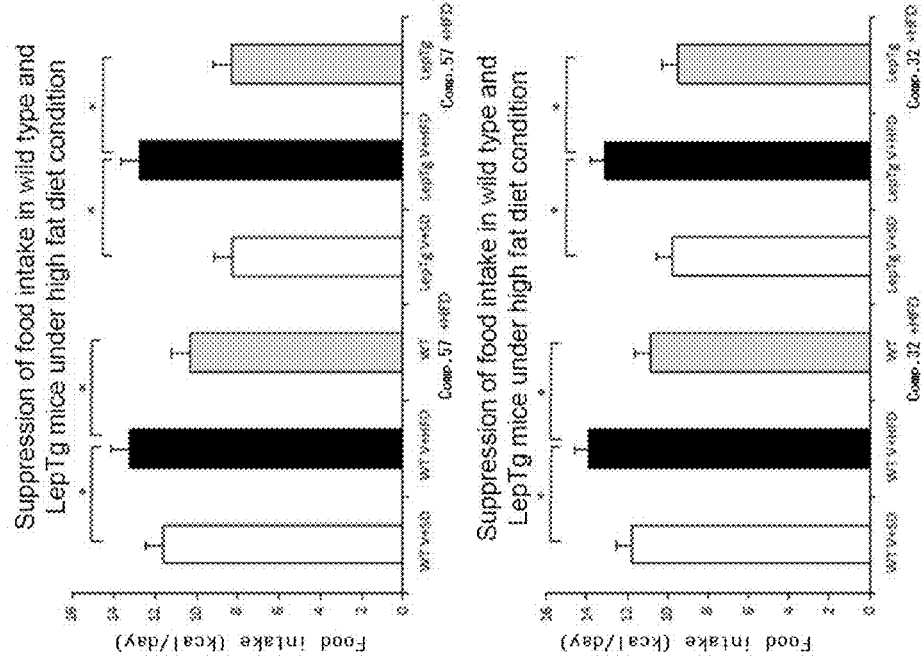
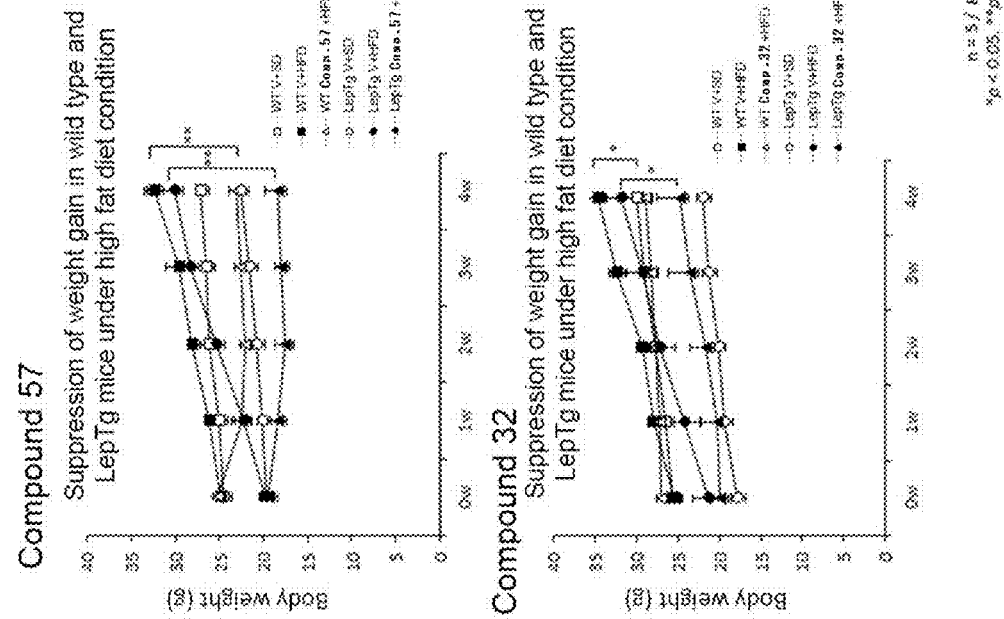

Fig. 2 Suppression of increase of weight of adipose tissues, liver weight and liver triglyceride levels in wild type and LepTg mice under high fat diet condition Fig. 6
Effects on weight of adipose tissues, liver weight, and liver triglyceride levels in leptin-deficient ob/ob mice
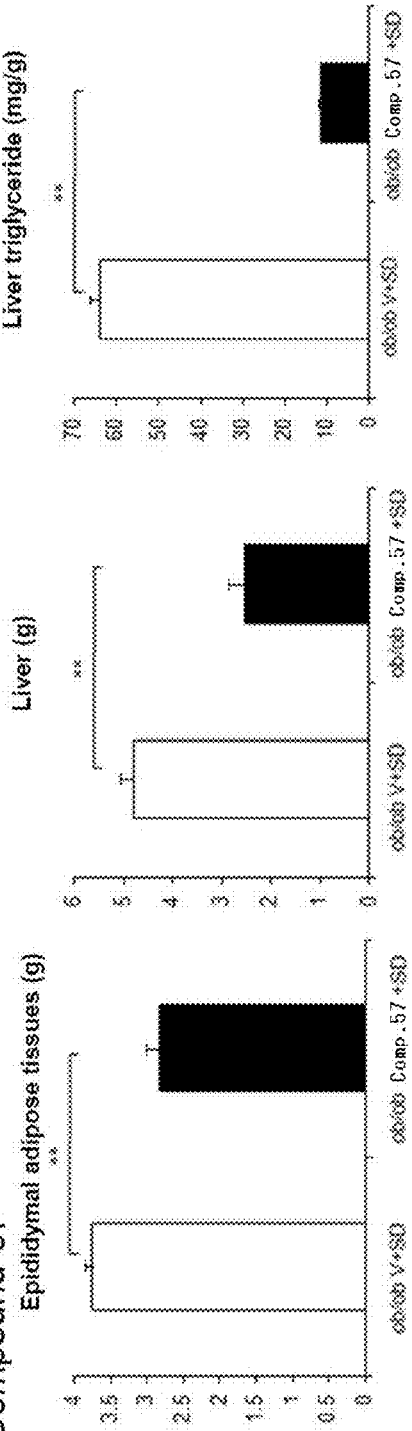
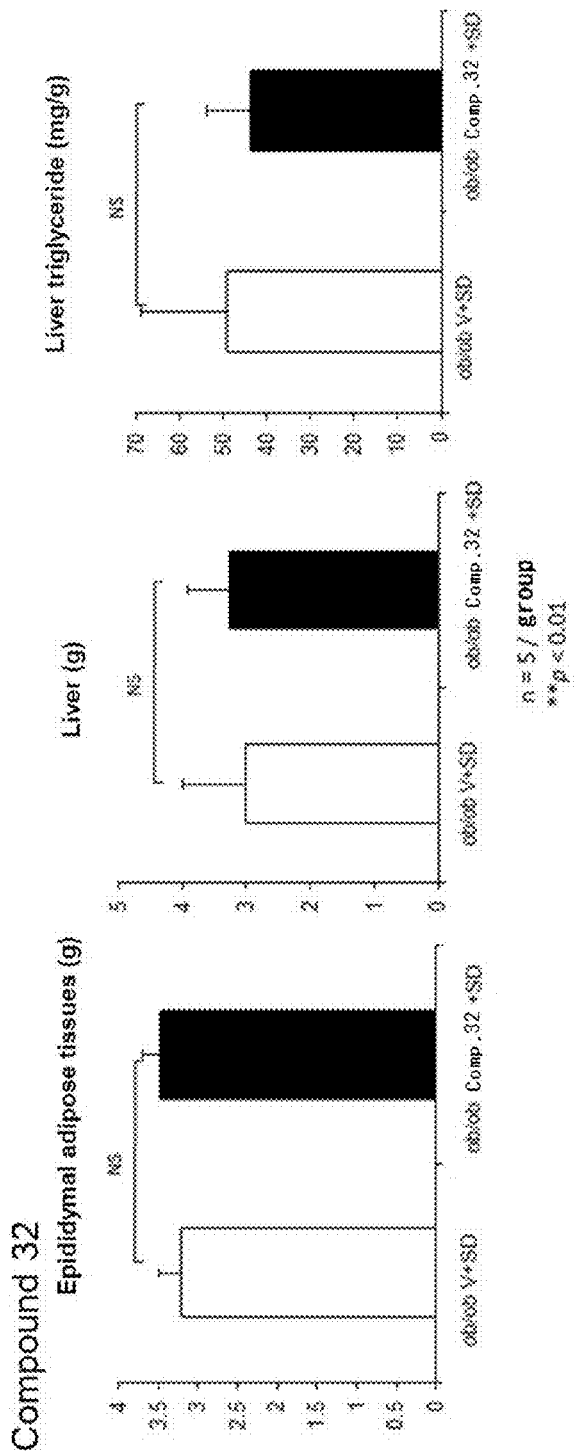

Fig. 7    Effects on insulin resistance in leptin-deficient ob/ob mice
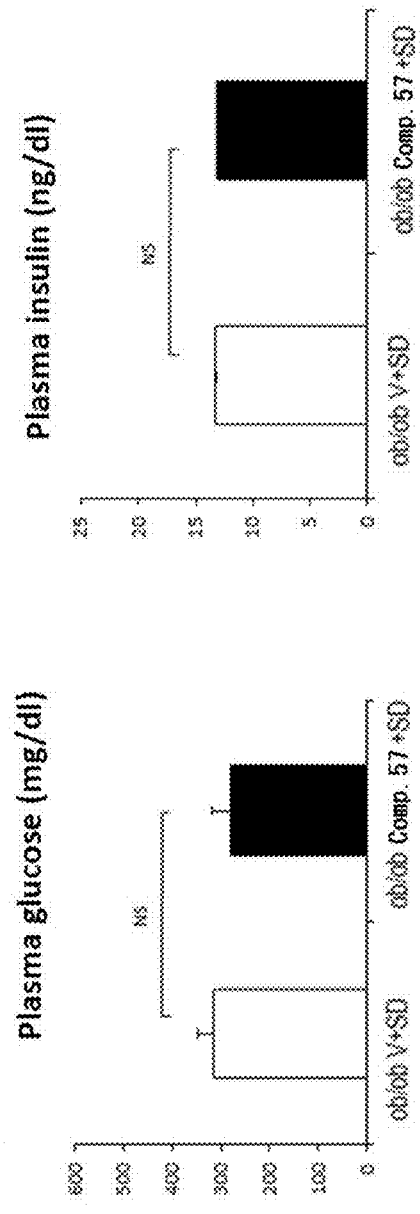
Compound 57
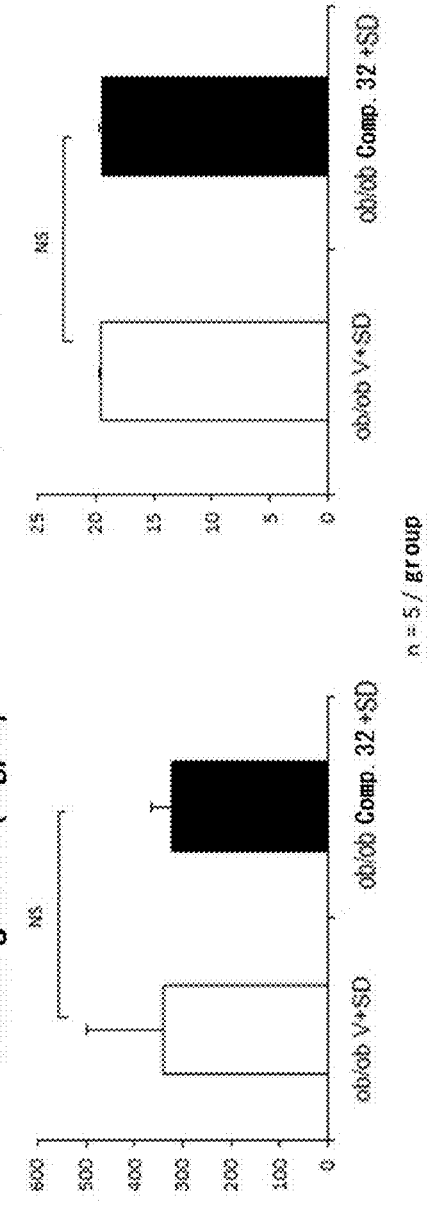
Compound 32
n = 5 / group

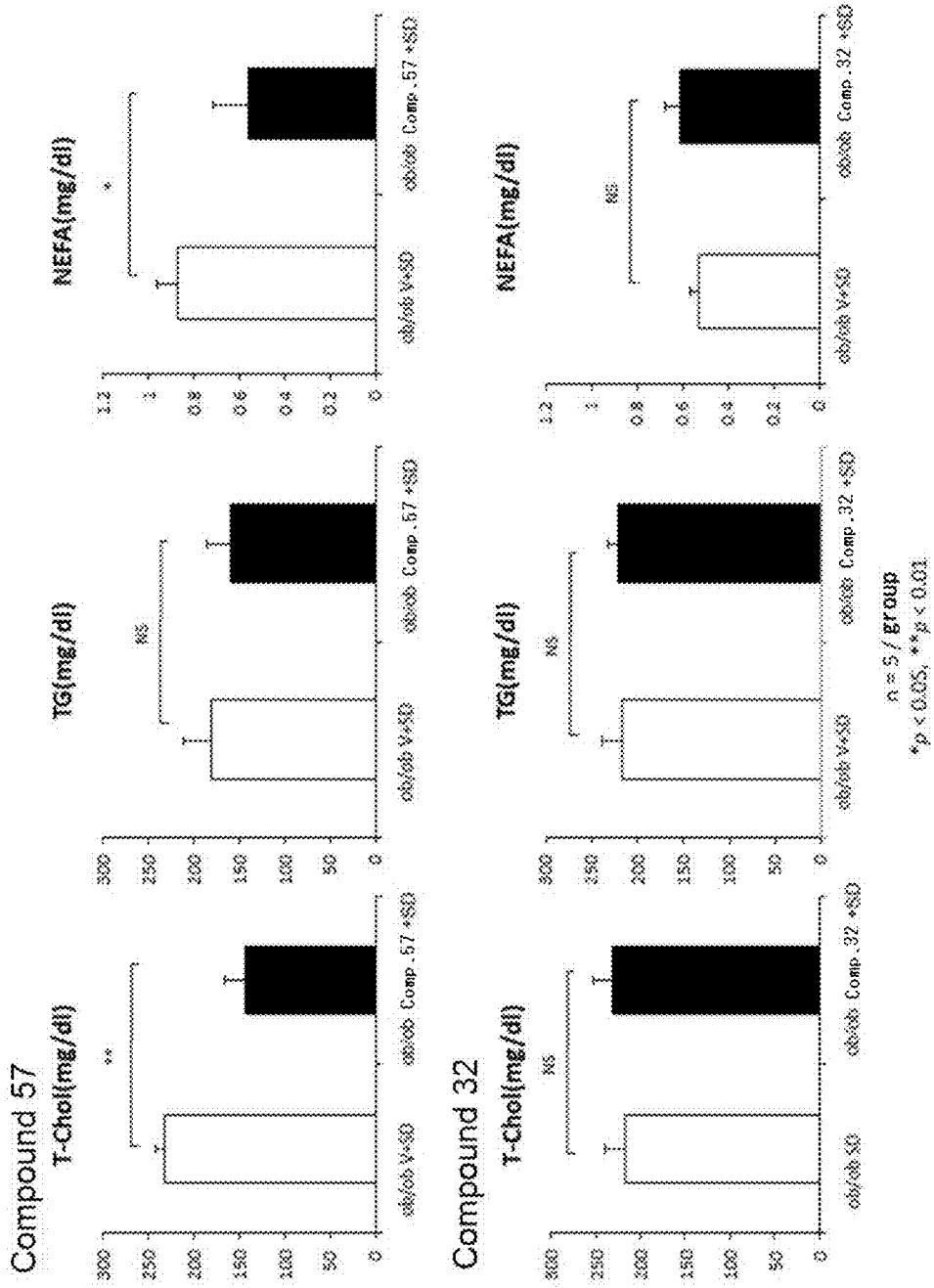

Fig. 9
Compound 57
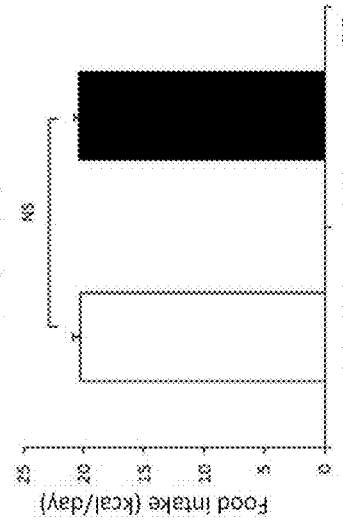
Effects on body weight in mice of lipodystrophy model
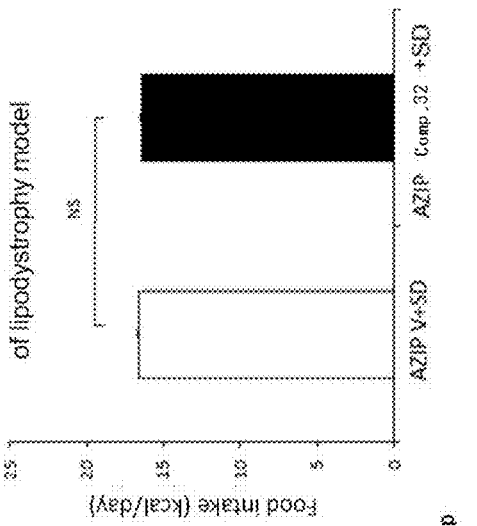
Effects on food intake in mice of lipodystrophy model
Compound 32
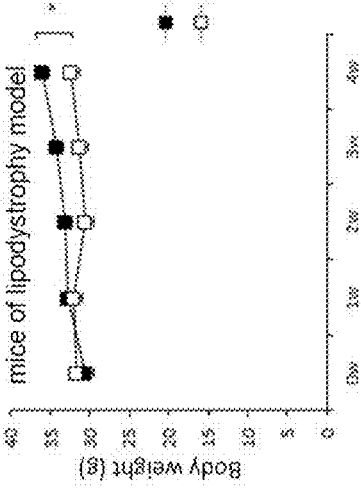
Effects on body weight in mice of lipodystrophy model
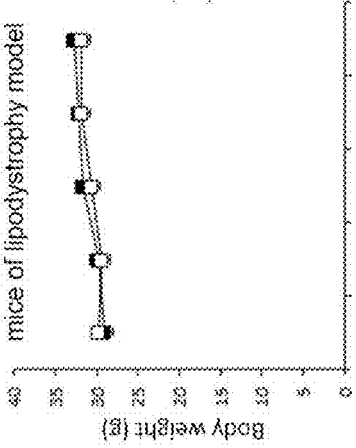
Effects on food intake in mice of lipodystrophy model
n = 5 / group
*p < 0.05

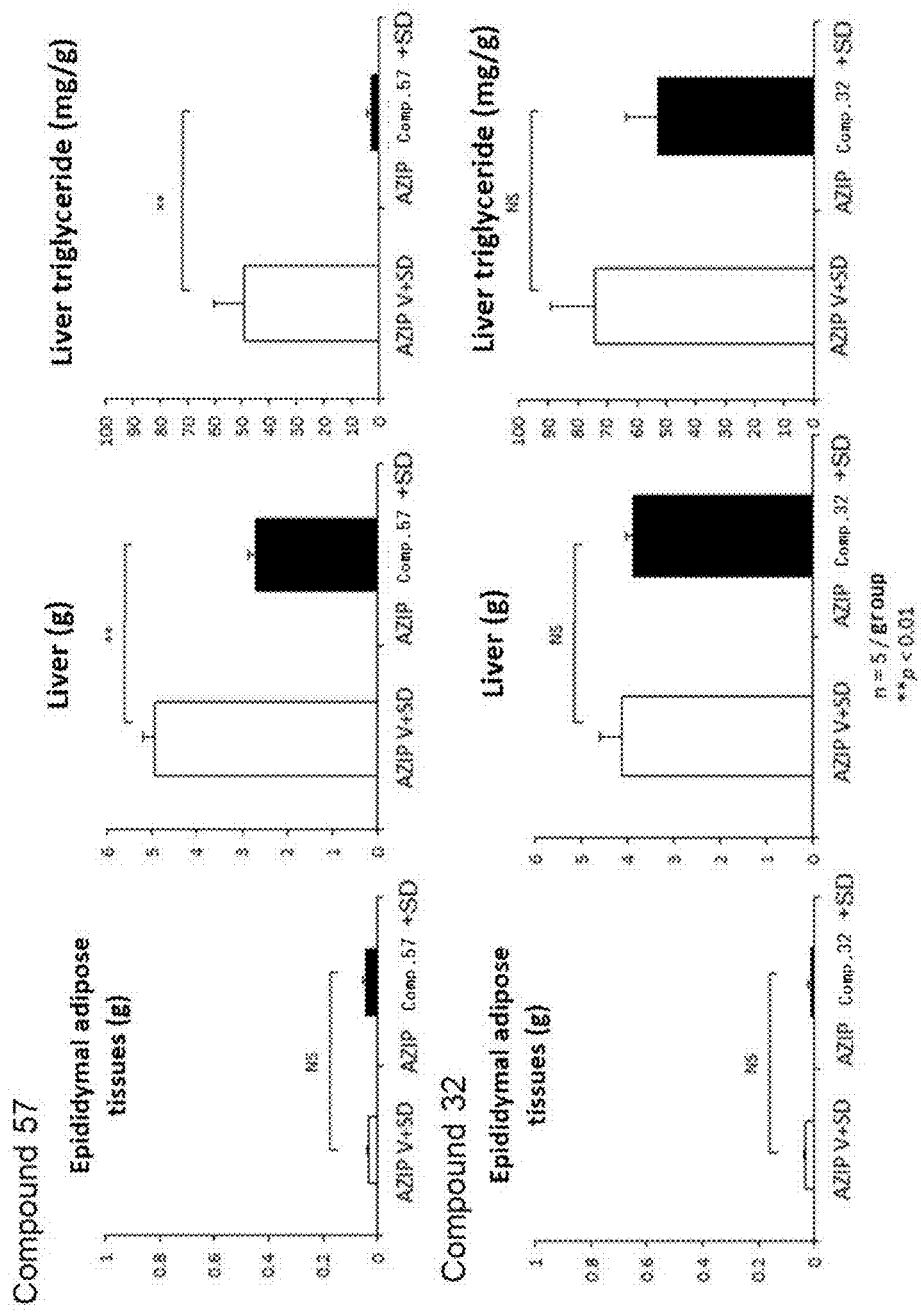
Fig. 10 Effects on weight of adipose tissues, liver weight, and liver triglyceride levels in mice of lipodystrophy model Fig. 11 Effects on insulin resistance in mice of lipodystrophy model
Compound 57
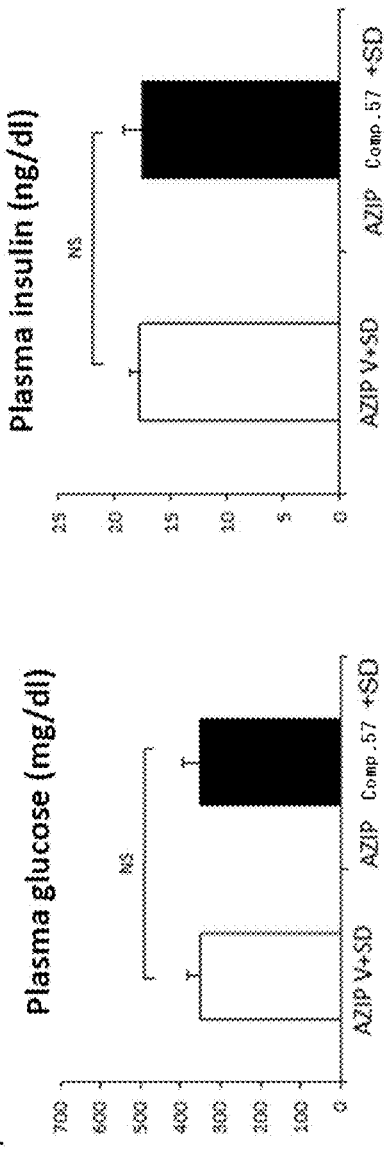
Compound 32
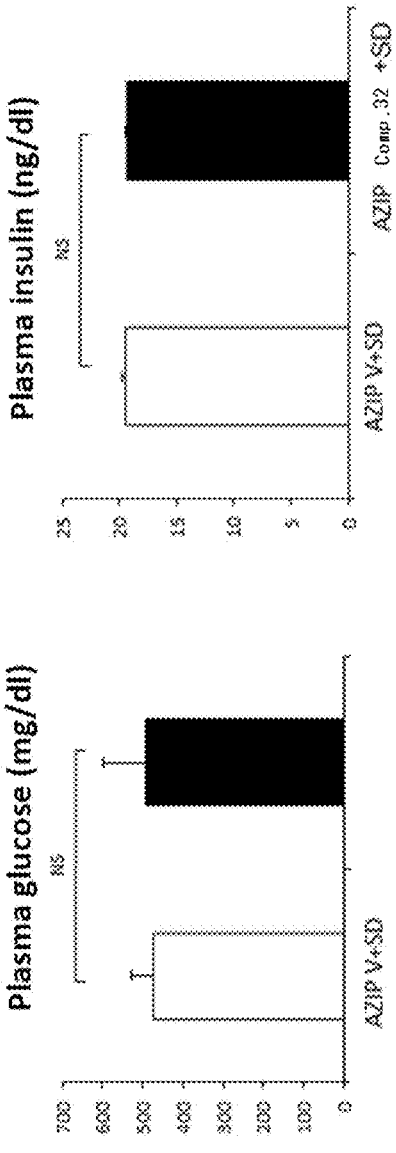
n = 5 / group

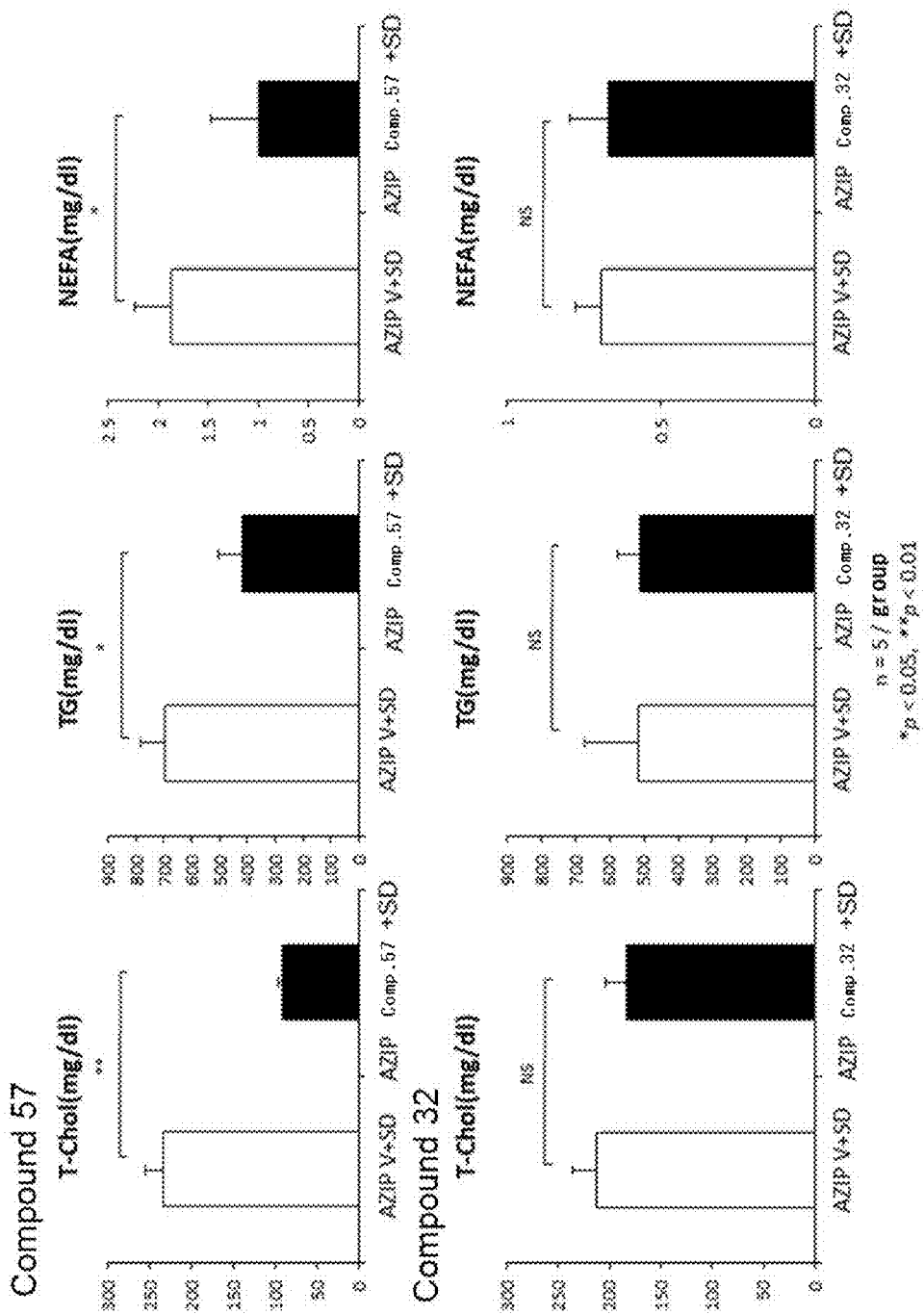
Fig. 12 Effects on lipid metabolism in mice of lipodystrophy model

Fig. 16 Effects of Compounds 57 and 32 to decrease liver weight in mice having diet-induced obesity Effects of Compounds 57 and 32 to suppress weight gain in wild type rats under high fat diet condition n=5 / group
**$p < 0.01$ Fig. 24 Effects of Compounds 57 and 32 on insulin resistance in Seipin KO rats, model of generalized lipodystrophy Effects of Compounds 57 and 32 to decrease weight of adipose tissues in rats having high fat diet-induced obesity n = 5 / group
*$p < 0.05$ Fig. 27 Effects of Compounds 57 and 32 to improve insulin resistance in rats having high fat diet-induced obesity

METHOD FOR IMPROVING LEPTIN RESISTANCE

This application is a national stage application of PCT/JP2014/073256 filed Sep. 3, 2014, which claims priority to Japanese Application No. 2013-183265 filed on Sep. 4, 2013.

TECHNICAL FIELD

The present invention provides a compound for use in improving leptin resistance, a pharmaceutical composition comprising the compound, a method for manufacturing a pharmaceutical for improving leptin resistance comprising using the compound, use of the compound in manufacture of a pharmaceutical for improving leptin resistance, and a method for improving leptin resistance comprising administering the compound or the pharmaceutical composition. The improvement of leptin resistance leads treatment and/or prevention of a disorder associated with leptin resistance, including, particularly, metabolic disorder, obesity, hyperphagia, steatosis, diabetes, and dyslipidemia.

BACKGROUND ART

Adipose tissues secrete a variety of signaling molecules that regulate systemic glucose and lipid metabolism. Leptin, which was discovered in 1994, is a primary adipose hormone that conveys an adiposity signal to the brain. The brain, particularly the hypothalamus, integrates leptin and various other metabolic signals to regulate energy homeostasis and body weight by controlling both behavior and metabolic responses. Leptin decreases body weight both by suppressing appetite and by increasing energy expenditure.

Obesity represents a risk factor for many diseases such as colon cancer, hyperlipidemia, hypertension, arteriosclerosis, and diabetes. No method for treating or preventing obesity with a medicine has been established. On the basis of the recent findings about leptin, treatment of obesity by administering leptin was attempted but ended in failure. This may be caused by "leptin resistance", which means decreased response to leptin, developed in patients of obesity. Leptin resistance likely results from the impairment in leptin transport to the brain, leptin signaling, and/or the neurocircuitry in the hypothalamus that regulate energy homeostasis, but the mechanism causing leptin resistance has not been completely revealed.

CITATION LIST

Non-Patent Literature

Non-Patent Literature 1: A. Christine Koenner and Jens C. Bruening, Cell Metabolism 16, Aug. 8, 2012, 144-152
Non-Patent Literature 2: David L. Morris and Liangyou Rui, Am. J. Physiol Endocrinol Metab 297: E1247-E1259, 2009

SUMMARY OF INVENTION

The inventors presumed that the improvement of leptin resistance would be effective for treating or preventing a disorder associated with leptin resistance such as obesity. An object of the invention is to provide a pharmaceutical for improving leptin resistance. Another object of the invention is to provide a pharmaceutical for treating and/or preventing a disorder associated with leptin resistance.

In an aspect, the present invention provides a compound of formula (I):

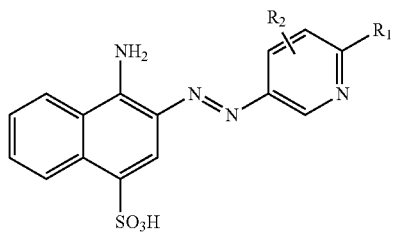

wherein
$R_1$ is aryl or heteroaryl, wherein the aryl or heteroaryl may be substituted with 1 to 3 substituents selected from the group consisting of halo, hydroxy, alkyl, halo-substituted alkyl, aryl, halo- or alkyl-substituted aryl, alkoxy, hydroxy- or carboxy-substituted alkoxy, alkylthio, aryloxy, CHO, C(O)-alkyl, C(O)-aryl, C(O)-alkylene-carboxyl, C(O)-alkylene-carboxy ester, cyano, oxo, heterocycloalkyl, and heteroaryl-substituted alkoxy, and
$R_2$ is hydrogen, halo, alkyl, phenyl, or pyridyl,
or an oxide, ester, prodrug, pharmaceutically acceptable salt, or solvate thereof (hereinafter referred to as the compound of the invention) for use in improving leptin resistance and/or treating and/or preventing a disorder associated with leptin resistance.

In a further aspect, the present invention provides a pharmaceutical composition for use in improving leptin resistance and/or treating and/or preventing a disorder associated with leptin resistance comprising a compound of formula (I) or an oxide, ester, prodrug, pharmaceutically acceptable salt, or solvate thereof.

In a further aspect, the present invention provides use of a compound of formula (I) or an oxide, ester, prodrug, pharmaceutically acceptable salt, or solvate thereof for manufacturing a pharmaceutical composition for improving leptin resistance and/or treating and/or preventing a disorder associated with leptin resistance.

In a further aspect, the present invention provides a method for improving leptin resistance and/or treating and/or preventing a disorder associated with leptin resistance comprising administering a therapeutically effective amount of a compound of formula (I) or an oxide, ester, prodrug, pharmaceutically acceptable salt, or solvate thereof to a subject in need thereof.

In a further aspect, a disorder associated with leptin resistance is a metabolic disorder, obesity, hyperphagia, steatosis, diabetes, or dyslipidemia.

The compounds of the invention enable improvement of leptin resistance. Accordingly, the compounds of the invention enable treatment and/or prevention of a disorder associated with leptin resistance such as a metabolic disorder, obesity, hyperphagia, steatosis, diabetes, or dyslipidemia via a novel mechanism which has not been known before.

BRIEF DESCRIPTION OF DRAWINGS

FIG. 1 shows the effects of Compounds 57 and 32 to suppress the weight gain and the food intake in the wild type mice and the transgenic mice overexpressing leptin (LepTg) under the high fat diet condition.

FIG. 6 shows the effects of Compounds 57 and 32 on the weight of the adipose tissues, the liver weight, and the liver triglyceride levels in the leptin-deficient ob/ob mice.

FIG. 7 shows the effects of Compounds 57 and 32 on insulin resistance in the leptin-deficient ob/ob mice.

FIG. 8 shows the effects of Compounds 57 and 32 on lipid metabolism in the leptin-deficient ob/ob mice.

FIG. 9 shows the effects of Compounds 57 and 32 on the body weight and the food intake in the mice of a lipodystrophy model.

FIG. 10 shows the effects of Compounds 57 and 32 on the weight of the adipose tissues, the liver weight, and the liver triglyceride levels in the mice of the lipodystrophy model.

FIG. 11 shows the effects of Compounds 57 and 32 on insulin resistance in the mice of the lipodystrophy model.

FIG. 12 shows the effects of Compounds 57 and 32 on lipid metabolism in the mice of the lipodystrophy model.

DESCRIPTION OF EMBODIMENTS

Definitions

Figure 2:
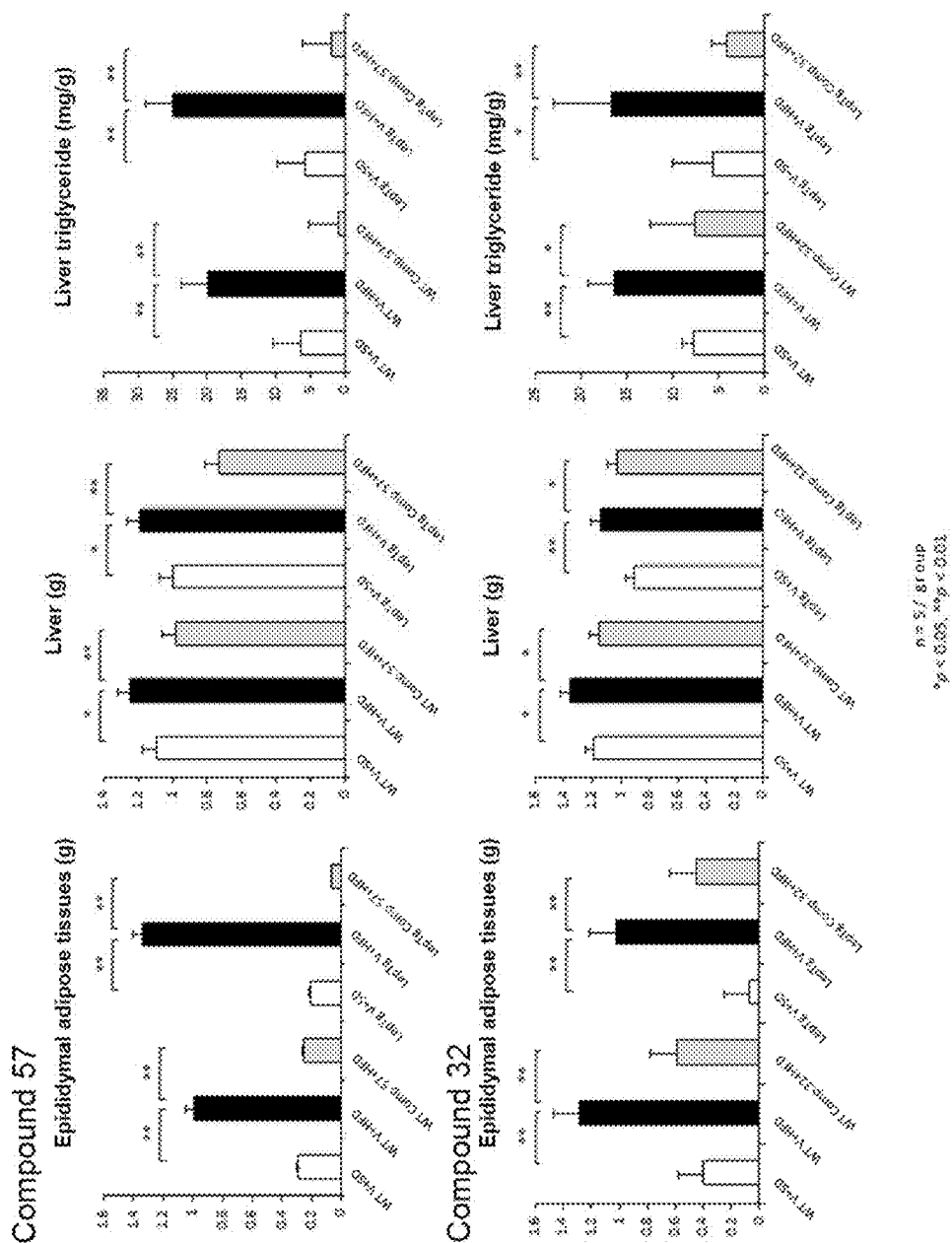
FIG. 2 shows the effects of Compounds 57 and 32 to suppress the increase of the weight of the adipose tissues, the liver weight and the liver triglyceride levels in the wild type and the LepTg mice under the high fat diet condition.

Unless defined otherwise, the terms used herein have the meaning as commonly understood to those skilled in the art in the fields including organic chemistry, medicine, pharmacology, molecular biology, and microbiology. Definitions of several terms used herein are described below. The definitions herein take precedence over the general understanding.

"Alkyl" refers to a monovalent saturated aliphatic hydrocarbyl group having from 1 to 10 carbon atoms, preferably 1 to 6 carbon atoms. Examples of the alkyl include, but not limited to, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)$ CH—), t-butyl (($CH_3)_3C$—), n-pentyl ($CH_3CH_2CH_2CH_2CH_2$—), and neopentyl (($CH_3)_3CCH_2$—).

The wording "substituted" as a word qualifying a name of a group means that one or more hydrogen atom of the group is, identically or differently, replaced by one or more substituent defined herein.

"Alkylene" refers to a divalent saturated aliphatic hydrocarbyl group having from 1 to 10 carbon atoms, preferably 1 to 6 carbon atoms. Alkylidene and alkylene groups include branched and straight chain hydrocarbyl groups.

"Alkoxy" refers to the group —O-alkyl, in which alkyl is as defined herein. Examples of the alkoxy include methoxy, ethoxy, n-propoxy, isopropoxy, n-butoxy, t-butoxy, sec-butoxy, and n-pentoxy.

"Alkylthio" refers to the group —S-alkyl, in which alkyl is as defined herein. Examples of the alkylthio include methylthio, ethylthio, n-propylthio, isopropylthio, n-butylthio, t-butylthio, sec-butylthio, and n-pentylthio.

"Aryl" or "Ar" refers to a monovalent aromatic carbocyclic group of from 6 to 14 carbon atoms having a single ring (e.g., phenyl) or multiple condensed rings (e.g., naphthyl, fluorenyl or anthryl). Typical aryl groups include phenyl, naphthyl, and fluorenyl.

"Aryloxy" refers to the group —O-aryl, in which aryl is as defined herein. Examples of the aryloxy include phenoxy and naphthoxy.

"Cyano" refers to the group —CN.

"Oxo" refers to an oxygen atom (=O).

"Carboxyl" or "carboxy" refers to the group —COOH or a salt thereof.

"Carboxy ester" refers to the group —C(O)O-alkyl, in which alkyl is as defined herein.

"Halo" or "halogen" refers to fluoro, chloro, bromo, or iodo.

"Hydroxy" or "hydroxyl" refers to the group —OH.

Interchangeably used "heterocycle", "heterocyclyl", and "heterocycloalkyl" refer to a saturated, partially saturated, or unsaturated non-aromatic group having a single ring or multiple condensed rings, including fused bridged and spiro ring systems, and having 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties. For example, heterocycloalkyl includes morpholinyl.

"Heteroaryl" refers to an aromatic group of from 1 to 12 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl, benzothienyl or dibenzothienyl), wherein one or more of the rings of the polycyclic heteroaryl may be cycloalkyl, aryl, or heteroaryl. In one embodiment, the nitrogen and/or the sulfur ring atom(s) of the heteroaryl group are optionally oxidized to provide for the N-oxide (N—>O), sulfinyl, or sulfonyl moieties. Heteroaryl includes, for example, furanyl, benzofuranyl, dibenzofuranyl, thiophenyl, benzothiophenyl, dibenzothiophenyl, pyrrolyl, indolyl, carbazole, benzothiazole, oxazole, isoxazole, pyridyl, quinolyl, isoquinolyl, thianthrenyl, phenoxathiinyl, phenothiazyl, or phenoxazyl.

Unless indicated otherwise, a substituent that is not explicitly defined herein is named by describing the name of the terminal functional group of the substituent first and sequentially describing the adjacent functional group toward the point binding to the rest of the compound. For example, the substituent "arylalkyloxycarbonyl" refers to (aryl)-(alkyl)-O—C(O)—.

It is understood that the definitions described above are not intended to include impermissible substitution patterns (e.g., methyl substituted with five fluoro groups). Those skilled in the art are familiar with such impermissible substitution patterns.

"Compound" as used herein refers to a compound encompassed by formula (I) disclosed herein and a specific compound represented by formula (I), including the oxides, esters, prodrugs, pharmaceutically acceptable salts, and solvates thereof. The term further includes the stereoisomers and tautomers of the compounds.

"Solvate" of a compound refers to the compound as defined above that is bound to a stoichiometric or non-stoichiometric amount of a solvent. The solvate includes solvates of an oxide, ester, prodrug, or pharmaceutically acceptable salt of the compound of formula (I). The solvent is volatile, non-toxic, and/or acceptable for administration to a human in a trace amount. For example, the solvate include hydrates and alcoholates, preferably hydrates.

"Stereoisomer" refers to a compound that differs from a compound having the same structure only in the chirality at one or more stereocenters. The stereoisomer includes enantiomers and diastereomers. The compound of formula (I) as well as the pharmaceutically acceptable salt, ester, oxide, and prodrug thereof may comprise an asymmetrically substituted carbon atom. Such asymmetrically substituted carbon atom may result in the compound existing in enantiomers, diastereomers, and other stereoisomeric forms that may be defined, in terms of absolute stereochemistry, such as in (R)— or (S)— forms. As a result, all such possible isomers, individual stereoisomers in their optically pure forms, mixtures thereof, racemic mixtures (or "racemates"), mixtures of diastereomers, as well as single diastereomers of the compounds are contemplated. The terms "S" and "R" configurations, as used herein, are as defined by the IUPAC 1974 RECOMMENDATIONS FOR SECTION E, FUNDAMENTAL STEREOCHEMISTRY, Pure Appl. Chem. 45:13-30 (1976).

"Tautomer" refers to alternate forms of a compound that differ only in the position of a proton, such as enol-keto and imine-enamine tautomers, or the tautomeric forms of heteroaryl groups containing a ring atom attached to both a ring —NH— moiety and a ring =N— moiety, such as pyrazoles, imidazoles, benzimidazoles, triazoles, and tetrazoles.

"Pharmaceutically acceptable salt" refers to a pharmaceutically acceptable salt derived from any of a variety of organic and inorganic counter ions well known in the art and includes, for example, salts of sodium, potassium, calcium, magnesium, ammonium, and tetraalkylammonium, and salts of organic or inorganic acids, such as hydrochloride, hydrobromide, tartrate, mesylate, acetate, maleate, and oxalate. Pharmaceutically acceptable salts include salts of the oxides, esters, or prodrugs of the compounds of formula (I).

As used herein, the term "pharmaceutically acceptable salt" includes nontoxic acid or alkaline earth metal salts of the compounds of formula (I). These salts can be prepared in situ during the final isolation and purification of the compounds of formula (I), or by separately reacting the base or acid functions in the compounds with a suitable organic or inorganic acid or base, respectively. Representative salts include, but are not limited to, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate, and undecanoate. The basic nitrogen-containing groups may be quaternized with reactive agents including alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides such as benzyl and phenethyl chlorides. Water or oil-soluble or dispersible products are thereby obtained.

Examples of the acid which may be employed to form pharmaceutically acceptable acid addition salts include inorganic acids such as hydrochloric acid, sulfuric acid and, phosphoric acid, and organic acids such as oxalic acid, maleic acid, methanesulfonic acid, succinic acid, and citric acid. Base addition salts can be prepared in situ during the final isolation and purification of the compounds of formula (I), or through a further reaction of the carboxylic acid group of the compound with a suitable base such as hydroxide, carbonate, or bicarbonate of a pharmaceutically acceptable metal cation, or ammonia, or an organic primary, secondary or tertiary amine. Pharmaceutically acceptable salts include, but are not limited to, cations of alkali and alkaline earth metals, such as sodium, lithium, potassium, calcium, magnesium, and aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine. Other representative organic amines useful for the formation of the base addition salts include diethylamine, ethylenediamine, ethanolamine, diethanolamine, and piperazine.

The term "oxide" as used herein refers to an oxide wherein a nitrogen and/or sulfur atom of a heteroaryl group is oxidized to form N-oxide, sulfinyl, or sulfonyl.

The term "ester" as used herein refers to an ester that hydrolyzes in vivo, including those that break down readily in a human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than six carbon atoms. Examples of particular esters include formates, acetates, propionates, butyrates, acrylates, and ethylsuccinates.

The term "prodrug" as used herein refers to a prodrug of the compound which is, within the scope of sound medical judgment, suitable for use in contact with the tissues of humans and animals without an undue adverse effect such as toxicity, irritation, and allergic response, commensurate with a reasonable benefit/risk ratio, and effective for their intended use, as well as the zwitterionic forms, where possible, of the compounds of the invention. The prodrug is a compound that is rapidly transformed in vivo to yield the parent compound of the formula above, for example by hydrolysis in blood. A general discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of formula (I) or the pharmaceutically acceptable salts, esters, oxides, and prodrugs of any of them, may be processed in vivo through metabolism in a human or animal body or cells to produce metabolites. The term "metabolite" as used herein refers to any derivatives of a parent compound produced in a subject after the administration of the parent compound. The derivatives may be produced from the parent compound through various biochemical transformations in the subject such as, for example, oxidation, reduction, hydrolysis, or conjugation, and include, for example, oxides and demethylated derivatives. The metabolites of the compounds of the invention may be identified using routine techniques known in the art. See, e.g., Bertolini, G. et al., J. Med. Chem. 40:2011-2016 (1997); Shan, D. et al., J. Pharm. Sci. 86(7):765-767; Bagshawe K., Drug Dev. Res. 34:220-230 (1995); Bodor, N., Advances in Drug Res. 13:224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991). It should be understood that individual chemical compounds that are metabolites of the compounds of formula (I) or the pharmaceutically acceptable salts, esters, oxides, and prodrugs of any of them, are included within the embodiments provided herein.

In an embodiment, the compound of the invention is a compound of formula (I), wherein $R_1$ is aryl or heteroaryl, wherein the aryl or heteroaryl may be substituted with 1 to 3 substituents selected from the group consisting of halo, hydroxy, alkyl, halo-substituted alkyl, aryl, halo- or alkyl-substituted aryl, alkoxy, hydroxy- or carboxy-substituted alkoxy, aryloxy, CHO, C(O)-alkyl, C(O)-aryl, C(O)-alkylene-carboxyl, C(O)-alkylene-carboxy ester, cyano, heterocycloalkyl, and heteroaryl-substituted alkoxy, and $R_2$ is hydrogen, alkyl, phenyl or pyridyl, or an oxide, ester, prodrug, pharmaceutically acceptable salt, or solvate thereof.

In an embodiment, the compound of the invention is a compound of formula (I), wherein $R_1$ is phenyl which may be substituted with 1 to 3 substituents independently selected from the group consisting of halo, hydroxy, alkyl, halo-substituted alkyl, aryl, halo- or alkyl-substituted aryl, alkoxy, hydroxy- or carboxy-substituted alkoxy, alkylthio, aryloxy, CHO, C(O)-alkyl, C(O)-aryl, C(O)-alkylene-carboxyl, C(O)-alkylene-carboxy ester, cyano, heterocycloalkyl, and heteroaryl-substituted alkoxy, or an oxide, ester, prodrug, pharmaceutically acceptable salt, or solvate thereof.

In an embodiment, the compound of the invention is a compound of formula (I), wherein $R_1$ is phenyl which may be substituted with 1 to 3 substituents independently selected from the group consisting of halo, hydroxy, alkyl, halo-substituted alkyl, aryl, halo- or alkyl-substituted aryl, alkoxy, hydroxy- or carboxy-substituted alkoxy, aryloxy, CHO, C(O)-alkyl, C(O)-aryl, C(O)-alkylene-carboxyl, C(O)-alkylene-carboxy ester, cyano, heterocycloalkyl, and heteroaryl-substituted alkoxy, or an oxide, ester, prodrug, pharmaceutically acceptable salt, or solvate thereof.

In an embodiment, the compound of the invention is a compound of formula (I), wherein $R_1$ is phenyl which may be substituted with 1 to 3 substituents independently selected from the group consisting of halo, hydroxy, alkyl, halo-substituted alkyl, alkoxy, alkylthio, phenyl, halo- or alkyl-substituted phenyl, pyridyl, and morpholinyl, or an oxide, ester, prodrug, pharmaceutically acceptable salt, or solvate thereof.

In an embodiment, the compound of the invention is a compound of formula (I), wherein $R_1$ is phenyl which may be substituted with 1 to 3 substituents independently selected from the group consisting of halo, hydroxy, alkyl, halo-substituted alkyl, alkoxy, phenyl, halo- or alkyl-substituted phenyl, pyridyl, and morpholinyl, or an oxide, ester, prodrug, pharmaceutically acceptable salt, or solvate thereof.

In an embodiment, the compound of the invention is a compound of formula (I), wherein $R_1$ is phenyl which may be substituted with 1 to 3 substituents independently selected from the group consisting of halo, alkyl, halo-substituted alkyl, alkoxy, and alkylthio, or an oxide, ester, prodrug, pharmaceutically acceptable salt, or solvate thereof.

In an embodiment, the compound of the invention is a compound of formula (I), wherein $R_1$ is phenyl which may be substituted with 1 to 3 substituents independently selected from the group consisting of halo and alkyl, or an oxide, ester, prodrug, pharmaceutically acceptable salt, or solvate thereof.

In an embodiment, the compound of the invention is a compound of formula (I), wherein
$R_1$ is phenyl which is substituted with halo and alkyl,
or an oxide, ester, prodrug, pharmaceutically acceptable salt, or solvate thereof.

In an embodiment, the compound of the invention is a compound of formula (I), wherein
$R_1$ is phenyl which is substituted with fluoro and methyl,
or an oxide, ester, prodrug, pharmaceutically acceptable salt, or solvate thereof.

In an embodiment, the compound of the invention is a compound of formula (I), wherein
$R_1$ is naphthyl, fluorenyl, furanyl, benzofuranyl, dibenzofuranyl, thiophenyl, benzothiophenyl, dibenzothiophenyl, pyrrolyl, indolyl, carbazole, benzothiazole, oxazole, isoxazole, pyridyl, quinolyl, isoquinolyl, thianthrenyl, phenoxathiinyl, phenothiazyl, or phenoxazyl which may be substituted with 1 to 3 substituents independently selected from the group consisting of halo, oxo, and alkyl,
or an oxide, ester, prodrug, pharmaceutically acceptable salt, or solvate thereof.

In an embodiment, the compound of the invention is a compound of formula (I), wherein
$R_1$ is naphthyl, furanyl, benzofuranyl, dibenzofuranyl, thiophenyl, benzothiophenyl, dibenzothiophenyl, pyrrolyl, indolyl, carbazole, oxazole, isoxazole, pyridyl, quinolyl, isoquinolyl, thianthrenyl, phenoxathiinyl, phenothiazyl, or phenoxazyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is naphthyl, benzofuranyl, dibenzofuranyl, benzothiophenyl, dibenzothiophenyl, indolyl, carbazole, benzothiazole, quinolyl, isoquinolyl, thianthrenyl, phenoxathiinyl, phenothiazyl, or phenoxazyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is naphthyl, benzofuranyl, dibenzofuranyl, benzothiophenyl, dibenzothiophenyl, indolyl, carbazole, quinolyl, isoquinolyl, thianthrenyl, phenoxathiinyl, phenothiazyl, or phenoxazyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is benzofuranyl, dibenzofuranyl, benzothiophenyl, dibenzothiophenyl, or thianthrenyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is dibenzofuranyl, benzothiophenyl, dibenzothiophenyl, carbazole, benzothiazole, or thianthrenyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is dibenzofuranyl, benzothiophenyl, dibenzothiophenyl, or thianthrenyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is benzothiophenyl or dibenzothiophenyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is dibenzothiophenyl which may be substituted with 1 to 3 substituents independently selected from the group consisting of halo and alkyl,
or an oxide, ester, prodrug, pharmaceutically acceptable salt, or solvate thereof.

In an embodiment, the compound of the invention is a compound of formula (I), wherein
$R_1$ is unsubstituted benzothiophenyl or dibenzothiophenyl,
or an oxide, ester, prodrug, pharmaceutically acceptable salt, or solvate thereof.

In an embodiment, the compound of the invention is a compound of formula (I), wherein
$R_1$ is unsubstituted dibenzothiophenyl,
or an oxide, ester, prodrug, pharmaceutically acceptable salt, or solvate thereof.

In an embodiment, the compound of the invention is a compound of formula (I), wherein
$R_2$ is hydrogen, halo or alkyl,
or an oxide, ester, prodrug, pharmaceutically acceptable salt, or solvate thereof.

In an embodiment, the compound of the invention is a compound of formula (I), wherein
$R_2$ is hydrogen or alkyl,
or an oxide, ester, prodrug, pharmaceutically acceptable salt, or solvate thereof.

In an embodiment, the compound of the invention is a compound of formula (I), wherein
$R_2$ is hydrogen,
or an oxide, ester, prodrug, pharmaceutically acceptable salt, or solvate thereof.

In an embodiment, the compound of the invention is a compound selected from Compounds 1 to 76 listed in Table 1 below, or a free acid form, oxide, ester, prodrug, pharmaceutically acceptable salt, or solvate thereof.

TABLE 1

| No. | Structure | Compound Name |
| --- | --- | --- |
| 1 | 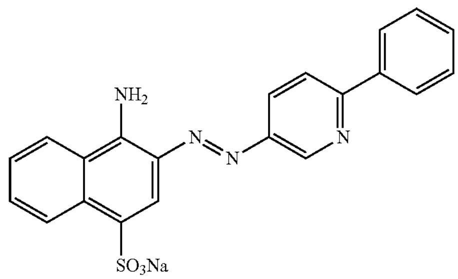 | 4-amino-3-(6-phenylpyridine-3-ylazo)naphthalene-1-sulfonic acid sodium salt |
| 2 | 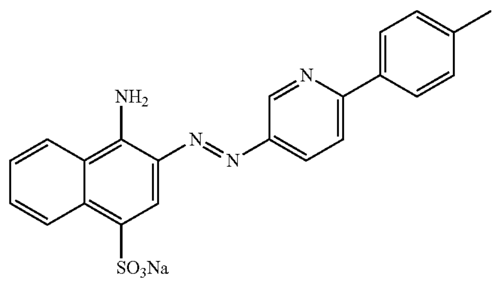 | 4-amino-3-(6-p-tolylpyridine-3-ylazo)naphthalene-1-sulfonic acid sodium salt |
| 3 | 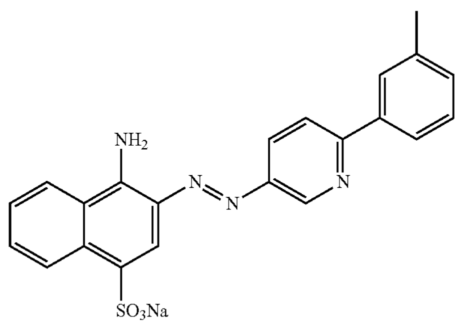 | 4-amino-3-(6-m-tolylpyridine-3-ylazo)naphthalene-1-sulfonic acid sodium salt |
| 4 | 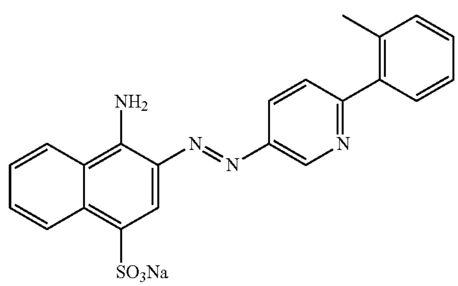 | 4-amino-3-(6-o-tolylpyridine-3-ylazo)naphthalene-1-sulfonic acid sodium salt |
| 5 | 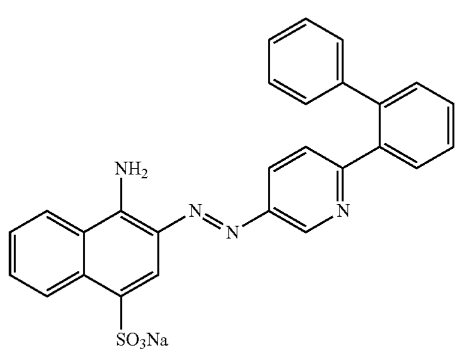 | 4-amino-3-(6-biphenyl-2-ylpyridine-3-ylazo)naphthalene-1-sulfonic acid sodium salt |

TABLE 1-continued

| No. | Structure | Compound Name |
|---|---|---|
| 6 | 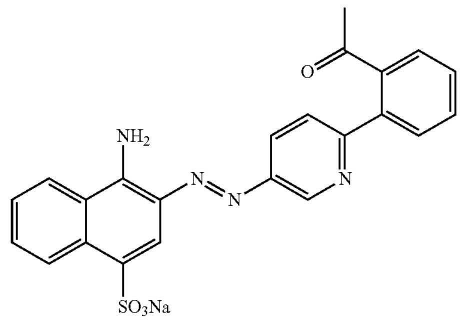 | 3-[6-(2-acetylphenyl)pyridine-3-ylazo]-4-aminonaphthalene-1-sulfonic acid sodium salt |
| 7 | 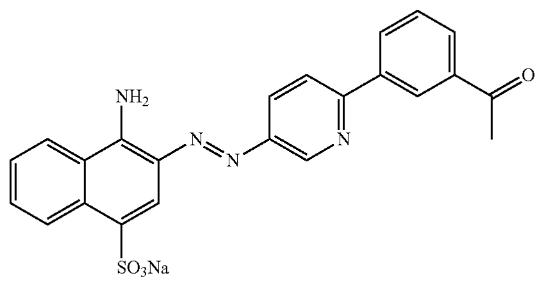 | 3-[6-(3-acetylphenyl)pyridine-3-ylazo]-4-aminonaphthalene-1-sulfonic acid sodium salt |
| 8 | 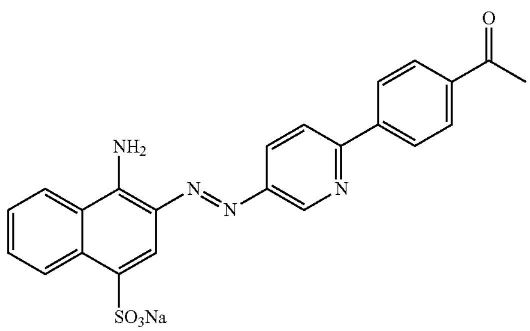 | 3-[6-(4-acetylphenyl)pyridine-3-ylazo]-4-aminonaphthalenesulfonic acid sodium salt |
| 9 | 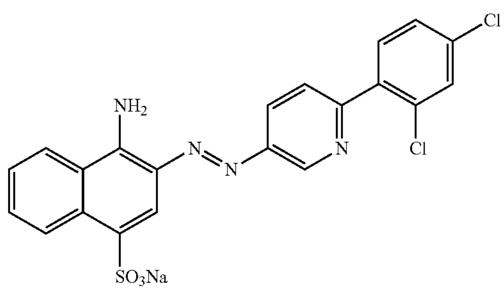 | 4-amino-3-[6-(2,4-dichlorophenyl)pyridine-3-ylazo]naphthalene-1-sulfonic acid sodium salt |
| 10 | 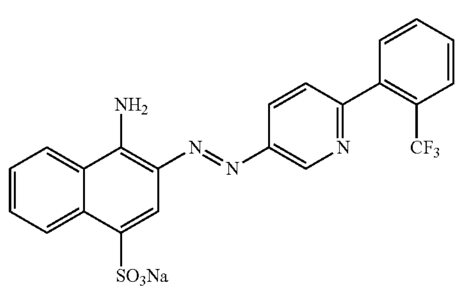 | 4-amino-3-[6-(2-trifluoromethylphenyl)pyridine-3-ylazo]naphthalene-1-sulfonic acid sodium salt |

TABLE 1-continued

| No. | Structure | Compound Name |
| --- | --- | --- |
| 11 | 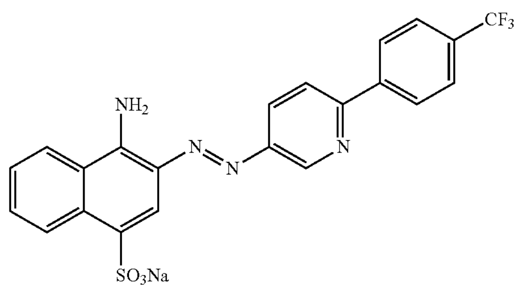 | 4-amino-3-[6-(4-trifluoromethylphenyl)pyridine-3-ylazo]naphthalene-1-sulfonic acid sodium salt |
| 12 | 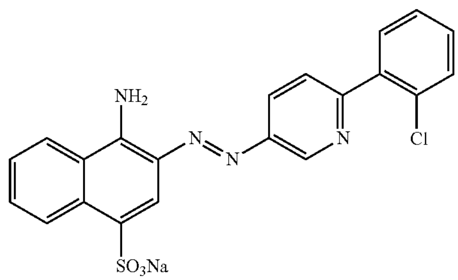 | 4-amino-3-[6-(2-chlorophenyl)pyridine-3-ylazo]naphthalene-1-sulfonic acid sodium salt |
| 13 | 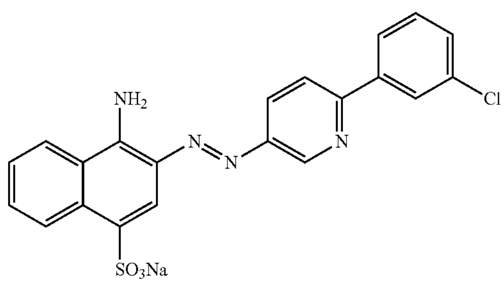 | 4-amino-3-[6-(3-chlorophenyl)pyridine-3-ylazo]naphthalene-1-sulfonic acid sodium salt |
| 14 | 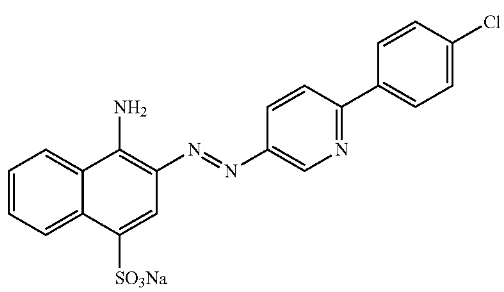 | 4-amino-3-[6-(4-chlorophenyl)pyridine-3-ylazo]naphthalene-1-sulfonic acid sodium salt |
| 15 | 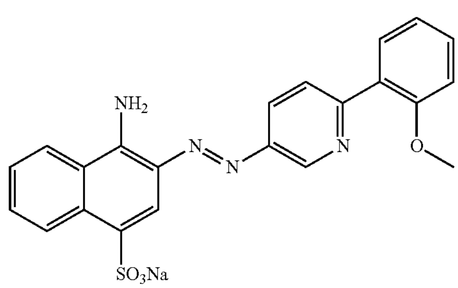 | 4-amino-3-[6-(2-methoxyphenyl)pyridine-3-ylazo]naphthalene-1-sulfonic acid sodium salt |

TABLE 1-continued

| No. | Structure | Compound Name |
|---|---|---|
| 16 | 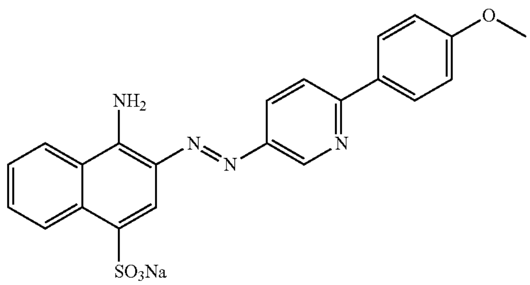 | 4-amino-3-[6-(4-methoxyphenyl)pyridine-3-ylazo]naphthalene-1-sulfonic acid sodium salt |
| 17 | 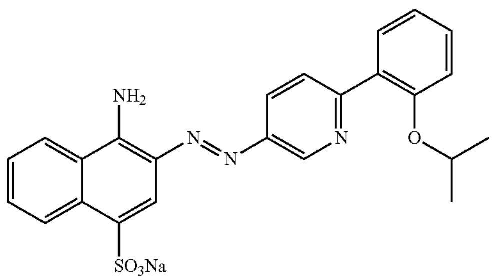 | 4-amino-3-[6-(2-isopropoxyphenyl)pyridine-3-ylazo]naphthalene-1-sulfonic acid sodium salt |
| 18 | 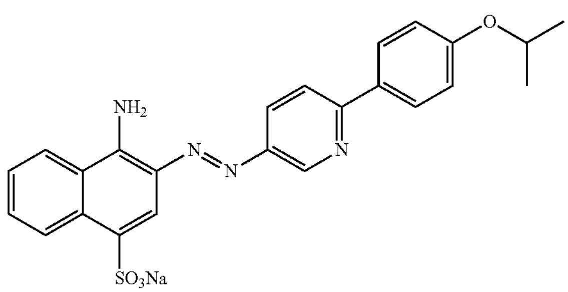 | 4-amino-3-[6-(4-isopropoxyphenyl)pyridine-3-ylazo]naphthalene-1-sulfonic acid sodium salt |
| 19 | 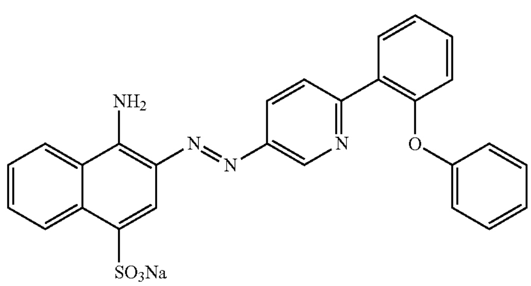 | 4-amino-3-[6-(2-phenoxyphenyl)pyridine-3-ylazo]naphthalene-1-sulfonic acid sodium salt |
| 20 | 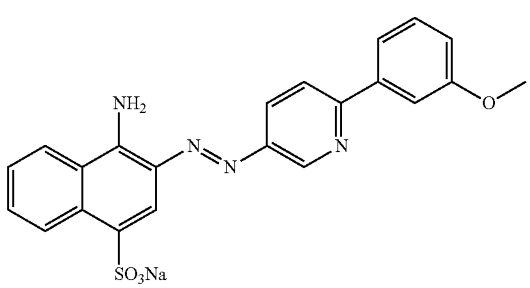 | 4-amino-3-[6-(3-methoxyphenyl)pyridine-3-ylazo]naphthalene-1-sulfonic acid sodium salt |

TABLE 1-continued

| No. | Structure | Compound Name |
|---|---|---|
| 21 | 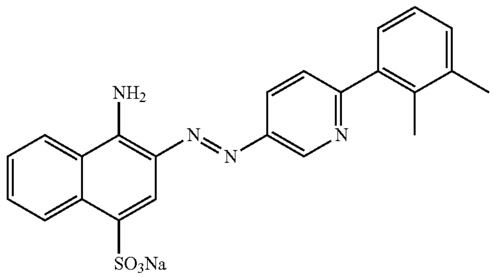 | 4-amino-3-[6-(2,3-dimethylphenyl)pyridine-3-ylazo]naphthalene-1-sulfonic acid sodium salt |
| 22 | 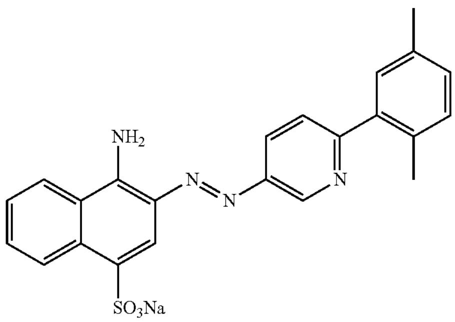 | 4-amino-3-[6-(2,5-dimethylphenyl)pyridine-3-ylazo]naphthalene-1-sulfonic acid sodium salt |
| 23 | 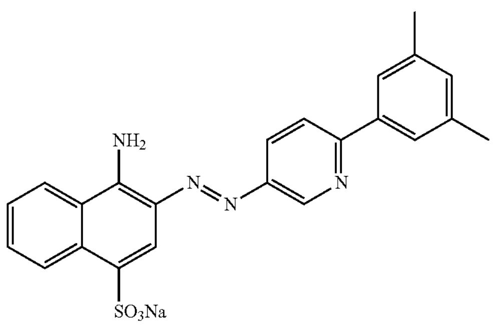 | 4-amino-3-[6-(3,5-dimethylphenyl)pyridine-3-ylazo]naphthalene-1-sulfonic acid sodium salt |
| 24 | 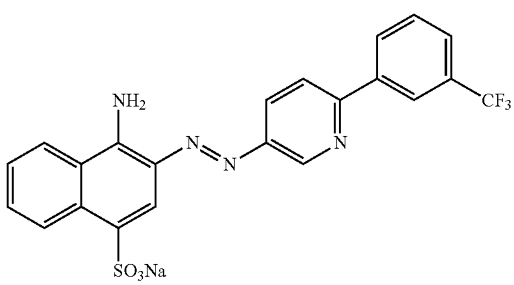 | 4-amino-3-[6-(3-trifluoromethylphenyl)pyridine-3-ylazo]naphthalene-1-sulfonic acid sodium salt |
| 25 | 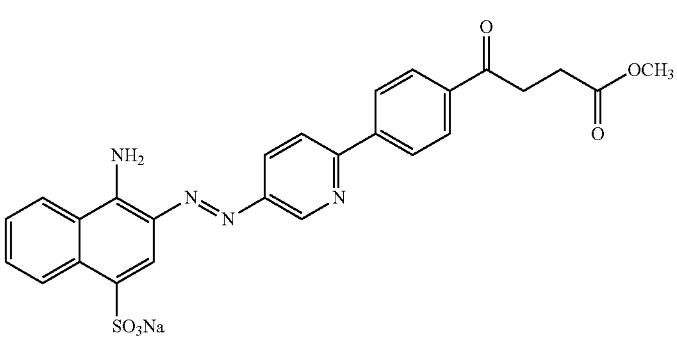 | methyl 4-{4-[5-(1-amino-4-sulfonaphthalene-2-ylazo)pyridine-2-yl]phenyl}-4-oxobutyrate sodium salt |

TABLE 1-continued

| No. | Structure | Compound Name |
|---|---|---|
| 26 | 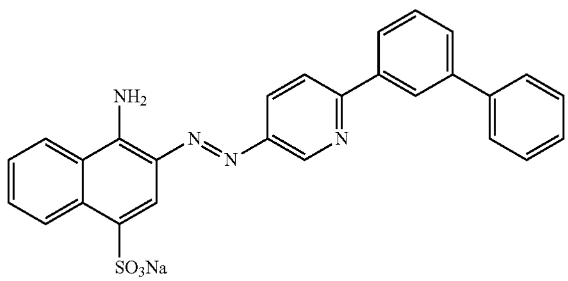 | 4-amino-3-(6-biphenyl-3-ylpyridine-3-ylazo)naphthalene-1-sulfonic acid sodium salt |
| 27 | 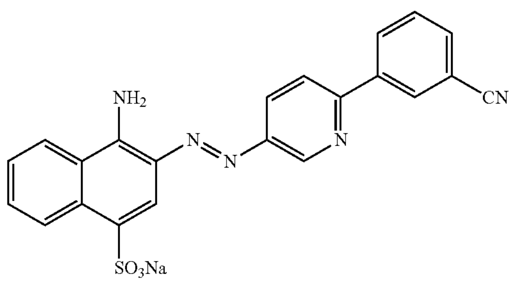 | 4-amino-3-[6-(3-cyanophenyl)pyridine-3-ylazo]naphthalene-1-sulfonic acid sodium salt |
| 28 | 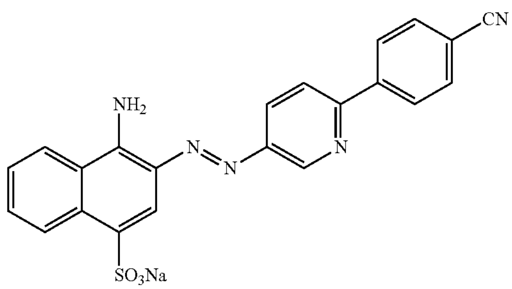 | 4-amino-3-[6-(4-cyanophenyl)pyridine-3-ylazo]naphthalene-1-sulfonic acid sodium salt |
| 29 | 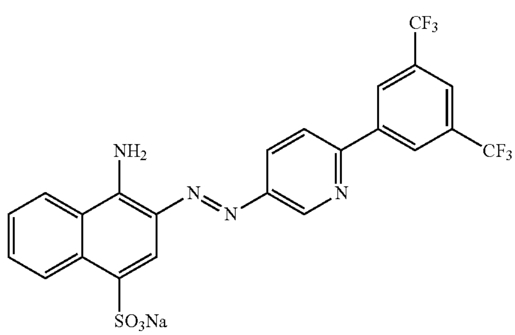 | 4-amino-3-[6-(3,5-bistrifluoromethylphenyl)pyridine-3-ylazo]naphthalenesulfonic acid sodium salt |
| 30 | 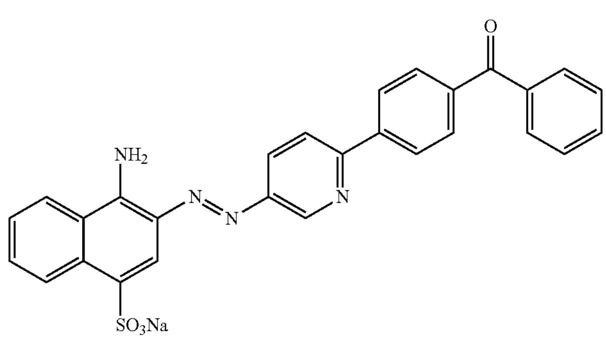 | 4-amino-3-[6-(4-benzoylphenyl)pyridine-3-ylazo]naphthalene-1-sulfonic acid sodium salt |

TABLE 1-continued

| No. | Structure | Compound Name |
|---|---|---|
| 31 | 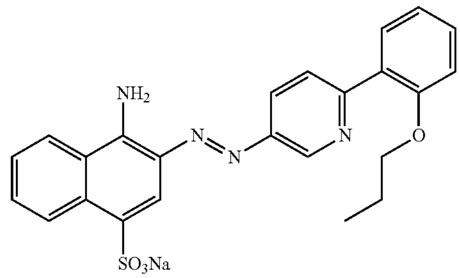 | 4-amino-3-[6-(2-propoxyphenyl)pyridine-3-ylazo]naphthalene-1-sulfonic acid sodium salt |
| 32 | 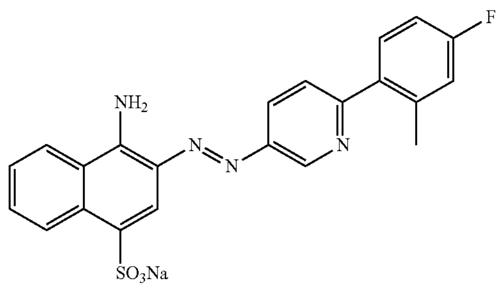 | 4-amino-3-[6-(4-fluoro-2-methylphenyl)pyridine-3-ylazo]naphthalene-1-sulfonic acid sodium salt |
| 33 | 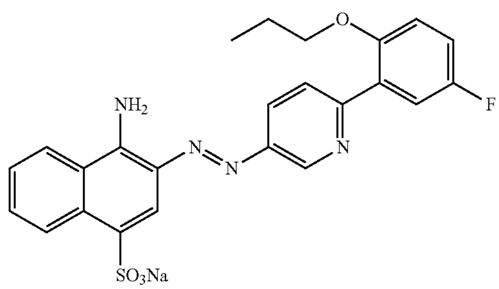 | 4-amino-3-[6-(5-fluoro-2-propoxyphenyl)pyridine-3-ylazo]naphthalene-1-sulfonic acid sodium salt |
| 34 | 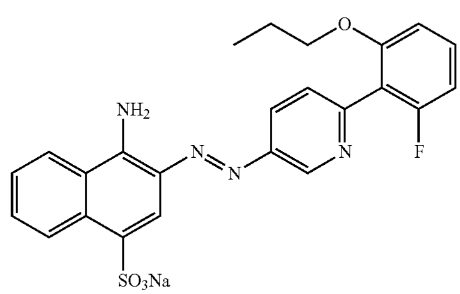 | 4-amino-3-[6-(2-fluoro-6-propoxyphenyl)pyridine-3-ylazo]naphthalene-1-sulfonic acid sodium salt |
| 35 | 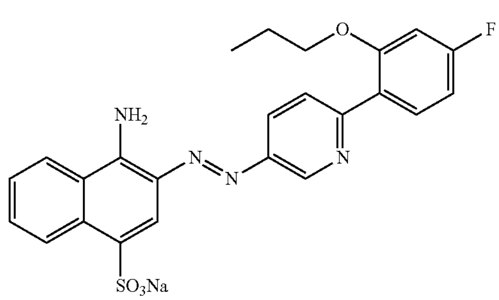 | 4-amino-3-[6-(4-fluoro-2-propoxyphenyl)pyridine-3-ylazo]naphthalene-1-sulfonic acid sodium salt |

TABLE 1-continued

| No. | Structure | Compound Name |
|-----|-----------|---------------|
| 36 | 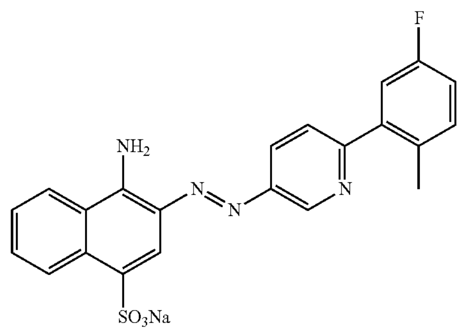 | 4-amino-3-[6-(5-fluoro-2-methylphenyl)pyridine-3-ylazo]naphthalene-1-sulfonic acid sodium salt |
| 37 | 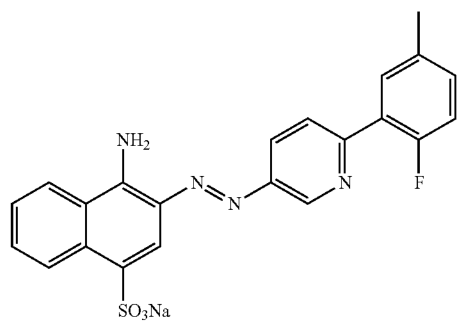 | 4-amino-3-[6-(2-fluoro-5-methylphenyl)pyridine-3-ylazo]naphthalene-1-sulfonic acid sodium salt |
| 38 | 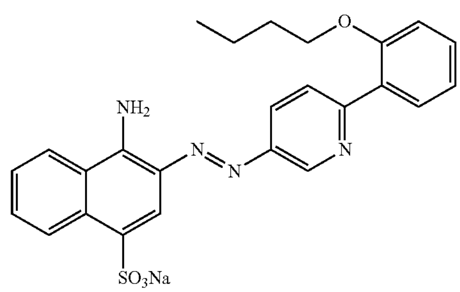 | 4-amino-3-[6-(2-butoxyphenyl)pyridine-3-ylazo]naphthalene-1-sulfonic acid sodium salt |
| 39 | 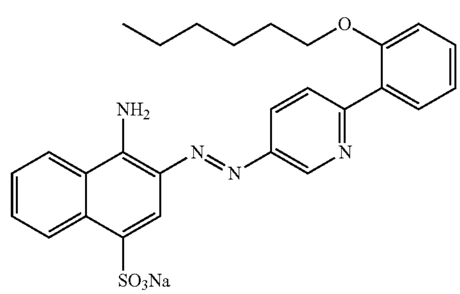 | 4-amino-3-[6-(2-hexyloxyphenyl)pyridine-3-ylazo]naphthalene-1-sulfonic acid sodium salt |
| 40 | 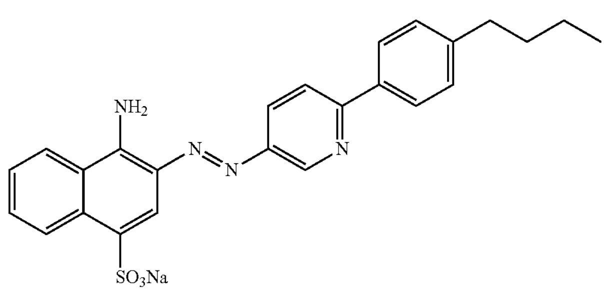 | 4-amino-3-[6-(4-butylphenyl)pyridine-3-ylazo]naphthalene-1-sulfonic acid sodium salt |

TABLE 1-continued

| No. | Structure | Compound Name |
| --- | --- | --- |
| 41 | 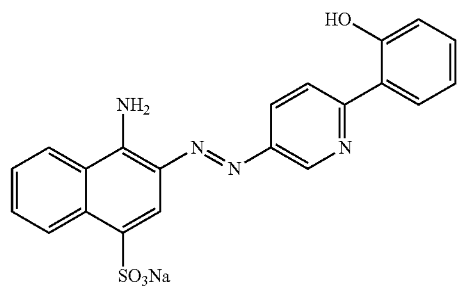 | 4-amino-3-[6-(2-hydroxyphenyl)pyridine-3-ylazo]naphthalene-1-sulfonic acid sodium salt |
| 42 | 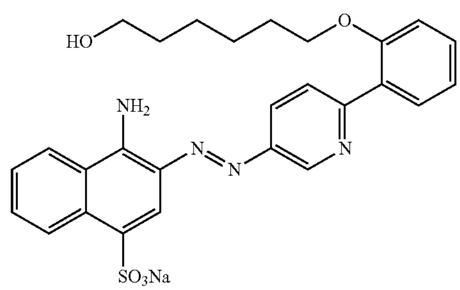 | 4-amino-3-{6-[2-(6-hydroxyhexyloxy)phenyl]pyridine-3-ylazo}naphthalene-1-sulfonic acid sodium salt |
| 43 | 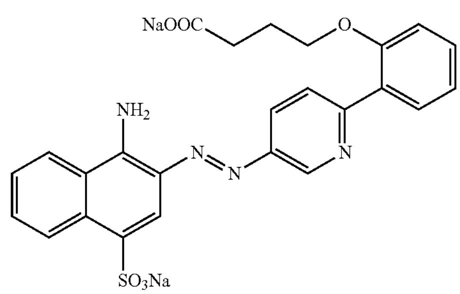 | 4-{2-[5-(1-amino-4-sulfonaphthalene-2-ylazo)pyridine-2-yl]phenoxy} butyric acid disodium salt |
| 44 | 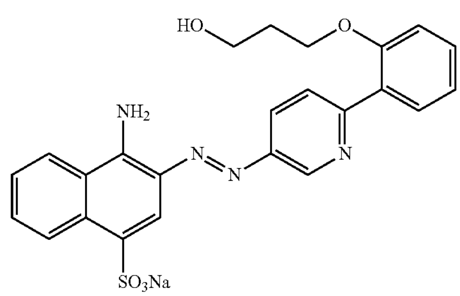 | 4-amino-3-{6-[2-(3-hydroxypropoxy)phenyl]pyridine-3-ylazo}naphthalene-1-sulfonic acid sodium salt |
| 45 | 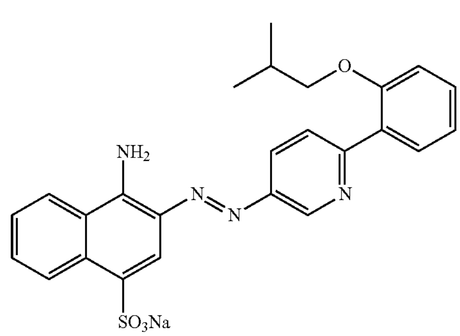 | 4-amino-3-[6-(2-isobutoxyphenyl)pyridine-3-ylazo]naphthalene-1-sulfonic acid sodium salt |

TABLE 1-continued

| No. | Structure | Compound Name |
|---|---|---|
| 46 | 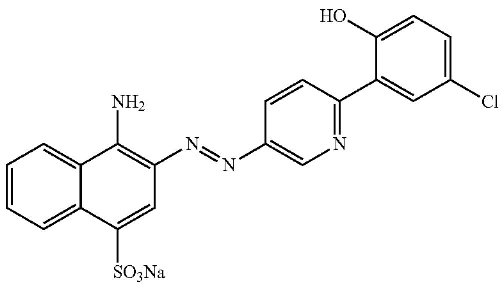 | 4-amino-3-[6-(5-chloro-2-hydroxyphenyl)pyridine-3-ylazo]naphthalene-1-sulfonic acid sodium salt |
| 47 | 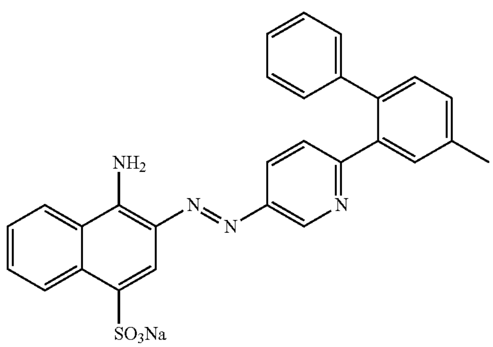 | 4-amino-3-[6-(4-methylbiphenyl-2-yl)pyridine-3-ylazo]naphthalene-1-sulfonic acid sodium salt |
| 48 | 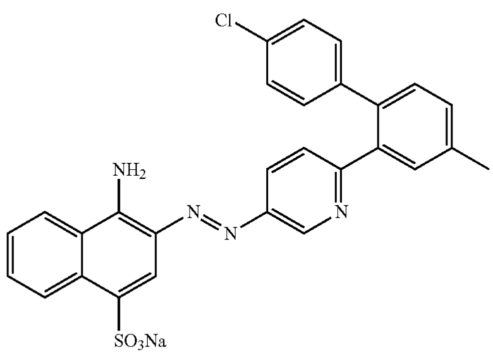 | 4-amino-3-[6-(4'-chloro-4-methylbiphenyl-2-yl)pyridine-3-ylazo]naphthalene-1-sulfonic acid sodium salt |
| 49 | 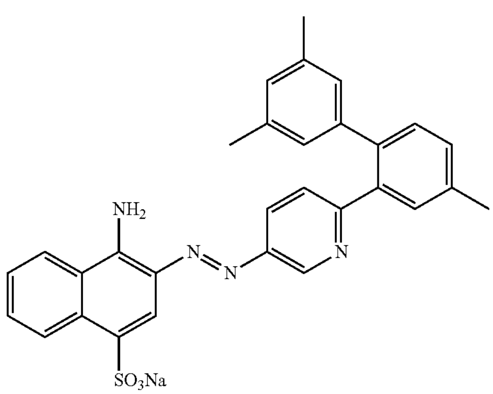 | 4-amino-3-[6-(4,3'-,5'-trimethylbiphenyl-2-yl)pyridine-3-ylazo]naphthalene-1-sulfonic acid sodium salt |

TABLE 1-continued

| No. | Structure | Compound Name |
|---|---|---|
| 50 | 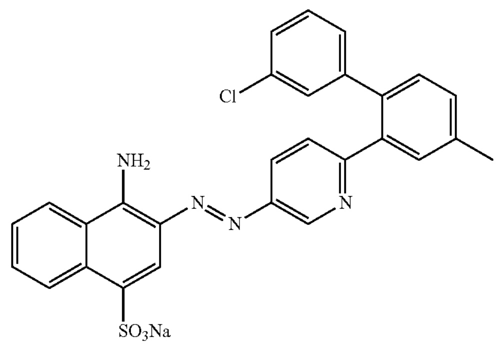 | 4-amino-3-[6-(3'-chloro-4-methylbiphenyl-2-yl)pyridine-3-ylazo]naphthalene-1-sulfonic acid sodium salt |
| 51 | 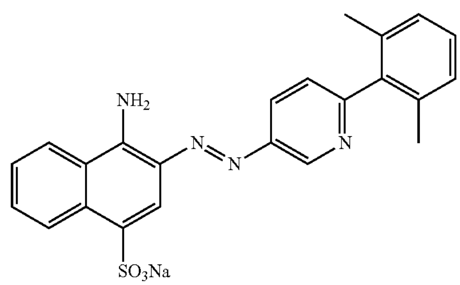 | 4-amino-3-[6-(2,6-dimethylphenyl)pyridine-3-ylazo]naphthalene-1-sulfonic acid sodium salt |
| 52 | 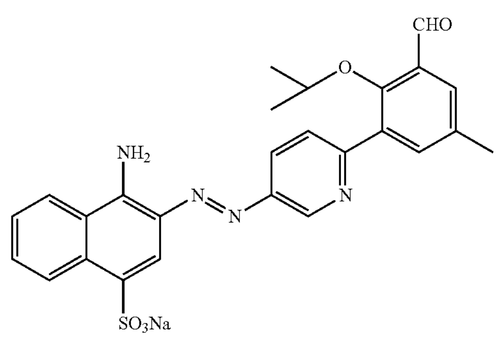 | 4-amino-3-[6-(3-formyl-2-isopropoxy-5-methylphenyl)pyridine-3-ylazo]naphthalene-1-sulfonic acid sodium salt |
| 53 | 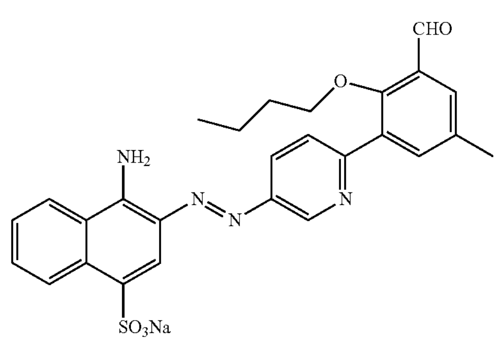 | 4-amino-3-[6-(3-formyl-2-butoxy-5-methylphenyl)pyridine-3-ylazo]naphthalene-1-sulfonic acid sodium salt |

TABLE 1-continued

| No. | Structure | Compound Name |
|---|---|---|
| 54 | 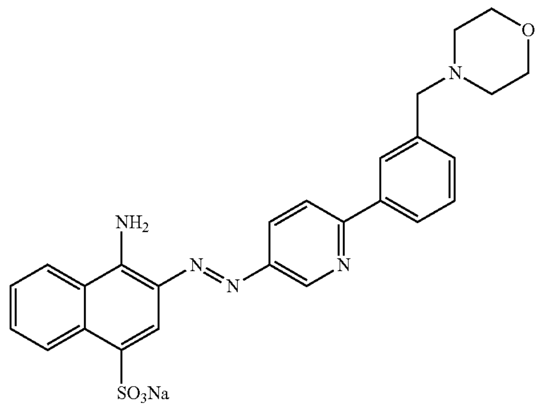 | 4-amino-3-[6-(3-morpholine-4-ylmethylphenyl)pyridine-3-ylazo]naphthalene-1-sulfonic acid sodium salt |
| 55 | 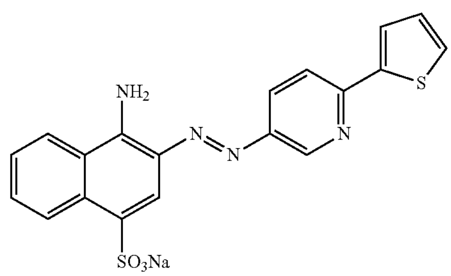 | 4-amino-3-(6-thiophene-2-ylpyridine-3-ylazo)naphthalene-1-sulfonic acid sodium salt |
| 56 | 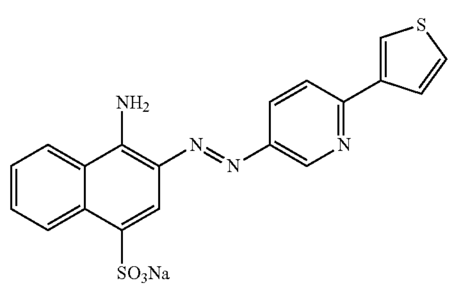 | 4-amino-3-(6-thiophene-3-ylpyridine-3-ylazo)naphthalene-1-sulfonic acid sodium salt |
| 57 | 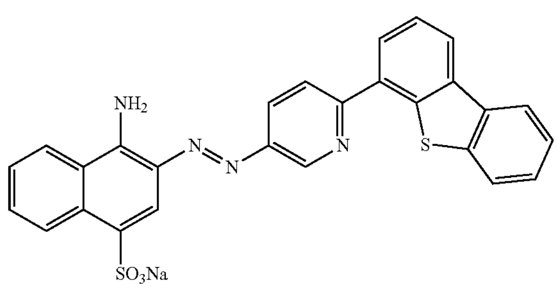 | 4-amino-3-(6-dibenzothiophene-4-ylpyridine-3-ylazo)naphthalene-1-sulfonic acid sodium salt |
| 58 | 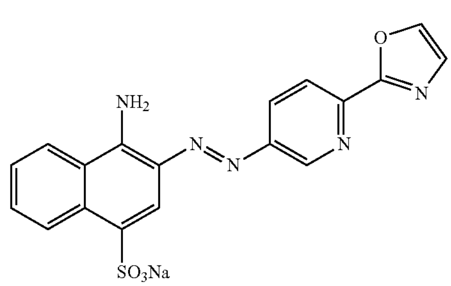 | 4-amino-3-(6-oxazole-2-ylpyridine-3-ylazo)naphthalene-1-sulfonic acid sodium salt |

TABLE 1-continued

| No. | Structure | Compound Name |
|---|---|---|
| 59 | 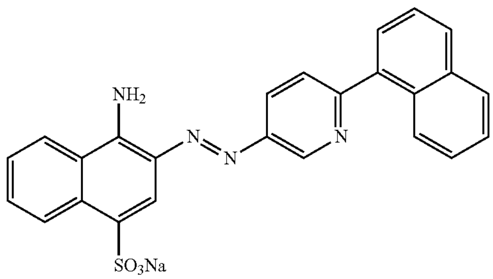 | 4-amino-3-(6-naphthalene-1-ylpyridine-3-ylazo)naphthalene-1-sulfonic acid sodium salt |
| 60 | 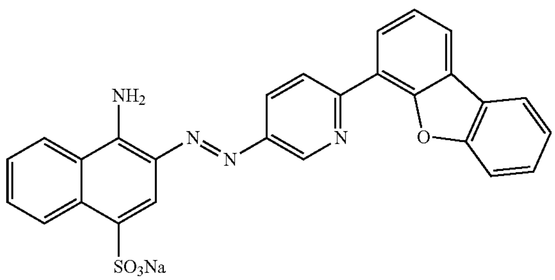 | 4-amino-3-(6-dibenzofuran-4-ylpyridine-3-ylazo)naphthalene-1-sulfonic acid sodium salt |
| 61 | 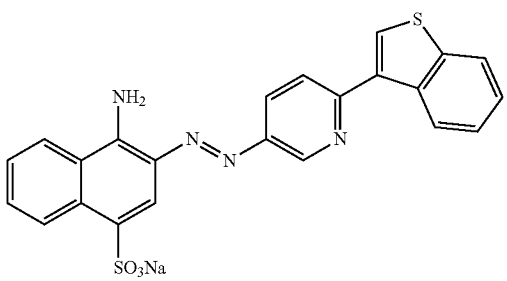 | 4-amino-3-(6-benzo[b]thiophene-3-ylpyridine-3-ylazo)naphthalene-1-sulfonic acid sodium salt |
| 62 | 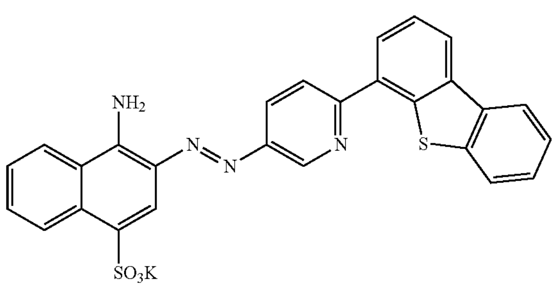 | 4-amino-3-(6-dibenzothiophene-4-ylpyridine-3-ylazo)naphthalene-1-sulfonic acid potassium salt |
| 63 | 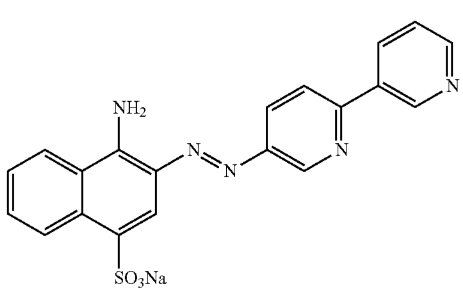 | 4-amino-3-([2,3']bipyridinyl-5-ylazo)naphthalene-1-sulfonic acid sodium salt |

TABLE 1-continued

| No. | Structure | Compound Name |
|---|---|---|
| 64 | 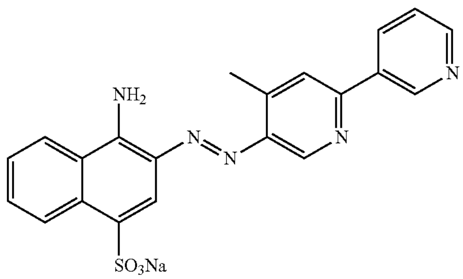 | 4-amino-3-(4-methyl-[2,3']bipyridinyl-5-ylazo)naphthalene-1-sulfonic acid sodium salt |
| 65 | 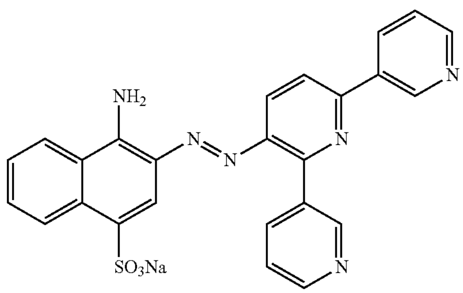 | 4-amino-3-([3,2';6',3'']terpyridine-3'-ylazo)naphthalene-1-sulfonic acid sodium salt |
| 66 | 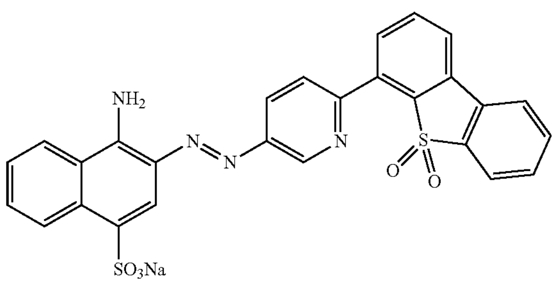 | 4-amino-3-[6-(5,5-dioxo-5H-5λ6-dibenzothiophene-4-yl)pyridine-3-ylazo]naphthalene-1-sulfonic acid sodium salt |
| 67 | 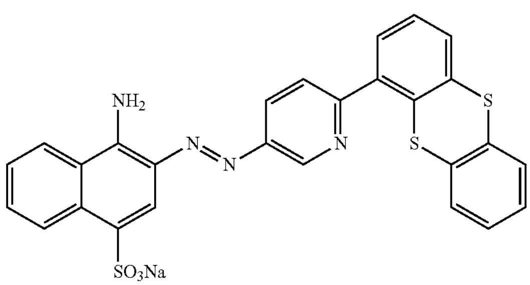 | 4-amino-3-(6-thianthrene-1-ylpyridine-3-ylazo)naphthalene-1-sulfonic acid sodium salt |
| 68 | 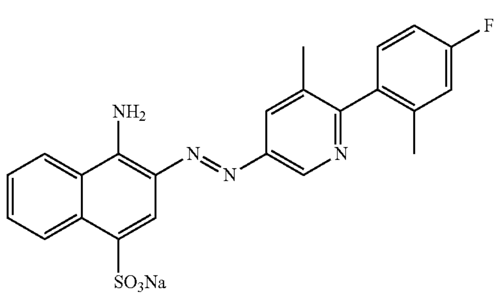 | 4-amino-3-[6-(4-fluoro-2-methylphenyl)-5-methylpyridine-3-ylazo]naphthalene-1-sulfonic acid sodium salt |

| No. | Structure | Compound Name |
|---|---|---|
| 69 | 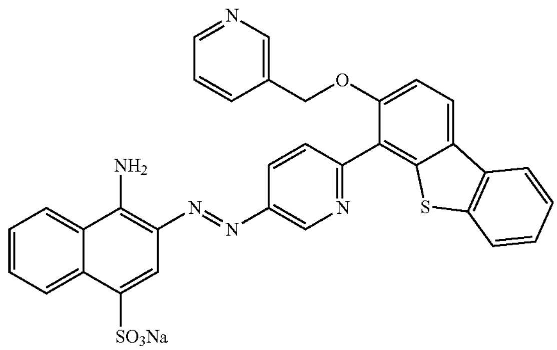 | 4-amino-3-{6-[3-(pyridine-3-ylmethoxy)dibenzothiophene-4-yl]pyridine-3-ylazo}naphthalene-1-sulfonic acid sodium salt |
| 70 | 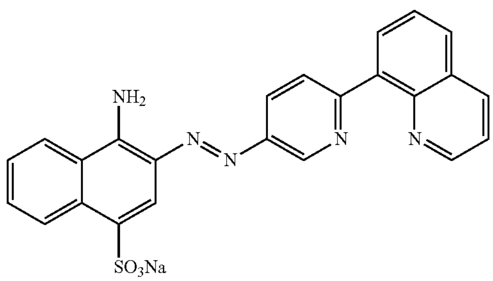 | 4-amino-3-(6-quinoline-8-ylpyridine-3-ylazo)naphthalene-1-sulfonic acid sodium salt |
| 71 | 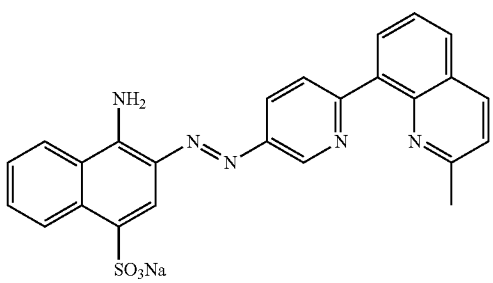 | 4-amino-3-[6-(2-methylquinoline-8-yl)pyridine-3-ylazo]naphthalene-1-sulfonic acid sodium salt |
| 72 | 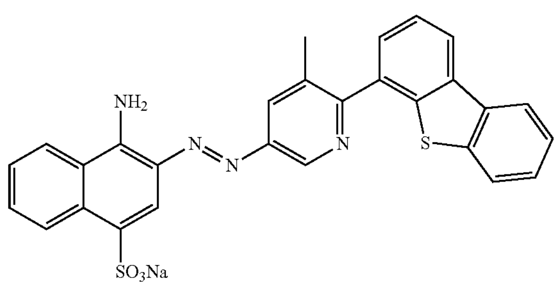 | 4-amino-3-(6-dibenzothiophene-4-yl-5-methylpyridine-3-ylazo)naphthalene-1-sulfonic acid sodium salt |
| 73 | 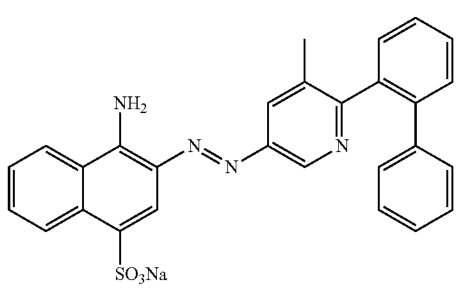 | 4-amino-3-(6-biphenyl-2-yl-5-methylpyridine-3-ylazo)naphthalene-1-sulfonic acid sodium salt |

TABLE 1-continued

| No. | Structure | Compound Name |
|---|---|---|
| 74 | 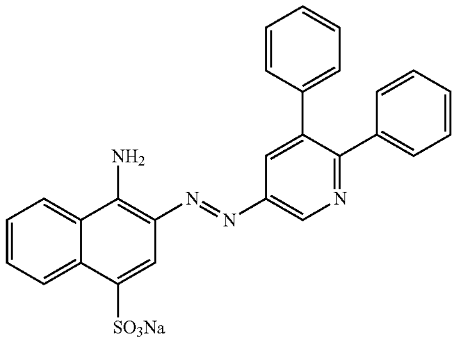 | 4-amino-3-(5,6-diphenylpyridine-3-ylazo)naphthalene-1-sulfonic acid sodium salt |
| 75 | 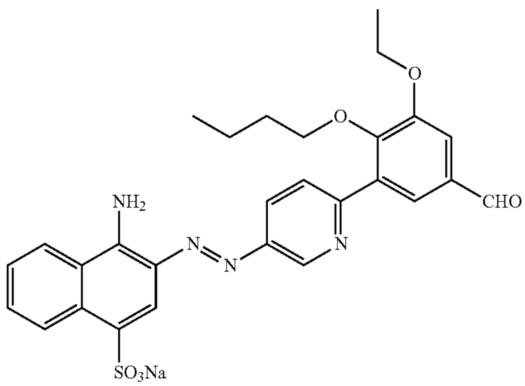 | 4-amino-3-[6-(2-butoxy-3-ethoxy-5-formylphenyl)pyridine-3-ylazo]naphthalene-1-sulfonic acid sodium salt |
| 76 | 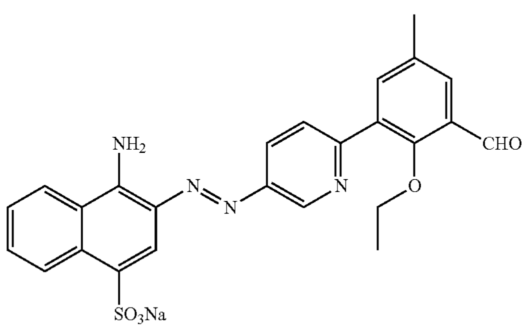 | 4-amino-3-[6-(2-ethoxy-3-formyl-5-methylphenyl)pyridine-3-ylazo]naphthalene-1-sulfonic acid sodium salt |

In an embodiment, the compound of the invention is the compound of the formula

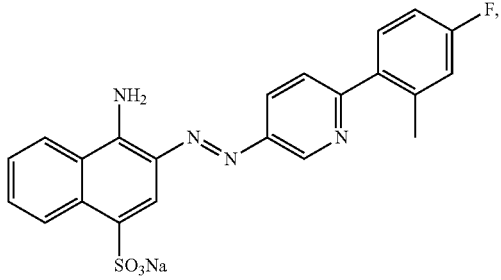

which is Compound 32 listed in Table 1 above, or an oxide, ester, prodrug, pharmaceutically acceptable salt, or solvate thereof, particularly a sodium salt thereof.

In an embodiment, the compound of the invention is the compound of the formula

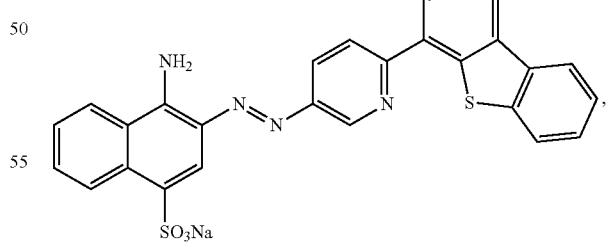

which is Compound 57 listed in Table 1 above, or an oxide, ester, prodrug, pharmaceutically acceptable salt, or solvate thereof, particularly a sodium salt thereof.

Methods for synthesizing the compounds of formula (I), especially the compounds of numbers 1 to 76, is described in WO2012/014994 and WO2012/043891 in detail, the contents of which are incorporated herein by reference in their entirety.

Administration and Pharmaceutical Composition

An embodiment of the present invention provides a pharmaceutical composition for use in improving leptin resistance and/or treating and/or preventing a disorder associated with leptin resistance comprising at least one compound of formula (I) or an oxide, ester, prodrug, pharmaceutically acceptable salt, or solvate thereof, either alone or together with a further agent, together with a pharmaceutically acceptable carrier suitable for administration to a human or animal subject.

An embodiment of the present invention provides use of at least one compound of formula (I) or an oxide, ester, prodrug, pharmaceutically acceptable salt, or solvate thereof for manufacturing a pharmaceutical composition for improving leptin resistance and/or treating and/or preventing a disorder associated with leptin resistance.

An embodiment of the present invention provides a method for improving leptin resistance and/or treating and/or preventing a disorder associated with leptin resistance comprising administering a therapeutically effective amount of at least one compound of formula (I) or an oxide, ester, prodrug, pharmaceutically acceptable salt, or solvate thereof to a human or animal subject in need thereof.

"Leptin resistance" as used herein means a condition wherein the ability of leptin in circulating blood to suppress appetite and/or weight gain and/or to enhance energy expenditure is impaired. "Improving leptin resistance" as used herein means preventing development of leptin resistance and alleviating, reducing and/or eliminating leptin resistance.

"Disorder associated with leptin resistance" as used herein means a disorder that can be treated and/or prevented by the improvement of leptin resistance, including, but not limited to, metabolic syndrome, hyperglycemia, hyperinsulinemia, metabolic disorders such as insulin resistance or glucose intolerance, diabetes such as diabetes mellitus, gestational diabetes, insulin-dependent diabetes mellitus, or non-insulin-dependent diabetes mellitus, diabetic complications such as diabetic retinopathy, diabetic nephropathy, or diabetic neuropathy, dyslipidemia such as hypercholesterolemia, hypertriglyceridemia, elevated postprandial plasma triglyceride level, hypoalphalipoproteinemia, or combined hyperlipidemia, obesity, hyperphagia, and steatosis.

The term "preventing" a disorder or "prevention" of a disorder in a subject refers to preventing the disorder from occurring in the subject that is predisposed or does not yet display symptoms of the disorder. The term "treating" a disorder or "treatment" of a disorder in a subject refers to 1) inhibiting the disorder or arresting its development; or 2) ameliorating or causing regression of the disorder.

The term "subject" as used herein refers to an animal. Typically the animal is a mammal. The subject also includes primates (e.g., humans), cows, sheep, goats, horses, dogs, cats, rabbits, rats, mice, fish and birds. In one embodiment, the subject is a primate. In another embodiment, the subject is a human. In another embodiment, the subject is a companion animal, particularly a dog or a cat.

In general, the compound of the invention is administered in a therapeutically effective amount by any of accepted modes of administration for agents that serve similar utilities. The actual amount of the compound, i.e., the active ingredient, depends upon numerous factors such as the severity of the disorder to be treated, the age and relative health of the subject, the potency of the used compound, the route and form of the administration, and other factors. The compound of the invention may be administered more than once a day, for example three or four times a day. All of these factors are within the skill of the attending clinician.

The amount of the active ingredient that may be combined with a carrier material to produce a single dosage form will vary depending upon the host to be treated and the particular mode of administration. It will be understood, however, that the specific dose level for any particular subject will depend upon a variety of factors including the activity of the specific compound employed, the age, body weight, general health, sex, and diet of the subject, the time and route of the administration, the rate of the excretion, the drug combination, and the severity of the specific disorder to be treated. The therapeutically effective amount for a given situation can be readily determined by routine experimentation and is within the skill and judgment of the ordinary clinician.

A therapeutically effective amount generally can be a total daily dose administered to a host in single or divided doses which may be in amounts, for example, of from about 0.001 to about 1000 mg/kg body weight daily and from about 1.0 to about 30 mg/kg body weight daily. A dosage unit composition may contain such amounts of submultiples thereof to make up the daily dose.

Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, and ion exchange resins, as well as combinations of any two or more thereof. Liquid and semisolid excipients may be selected from glycerol, propylene glycol, water, ethanol and various oils, including those of petroleum, animal, vegetable or synthetic origin, e.g., peanut oil, soybean oil, mineral oil, or sesame oil. In some embodiments, liquid carriers, particularly for injectable solutions, include water, saline, aqueous dextrose, and glycols. Other suitable pharmaceutically acceptable excipients are described in "Remington's Pharmaceutical Sciences," Mack Pub. Co., New Jersey (1991).

The choice of formulation depends on various factors such as the mode of drug administration and bioavailability of the drug substance. The drug can be administered as pharmaceutical compositions by any one of the following routes or combination of two or more of them: oral, systemic (e.g., transdermal, intranasal or by suppository), or parenteral (e.g., intramuscular, intravenous or subcutaneous) administration. An exemplary manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administration is inhalation such as for delivering a therapeutic agent directly to the respiratory tract (see U.S. Pat. No. 5,607,915). Topical administration may also involve the use of transdermal administration such as transdermal patches or ionophoresis devices. The term "parenteral" as used herein includes subcutaneous injections, intravenous, intraperitoneal, intramuscular, intrasternal injection, or infusion techniques.

Injectable preparations, for example, sterile injectable aqueous or oleaginous suspensions may be formulated according to the known art using suitable dispersing or wetting agents or suspending agents. The sterile injectable preparation may also be a sterile injectable solution or suspension in a nontoxic parenterally acceptable diluent or solvent, for example, as a solution in 1,3-propanediol.

Among the acceptable vehicles and solvents that may be employed are water, Ringer's solution, and isotonic sodium chloride solution. In addition, sterile, fixed oils are conventionally employed as a solvent or suspending medium. For this purpose fixed oils of any grade may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compound of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain agents such as stabilizers, preservatives, and excipients. Examples of lipids are the phospholipids and phosphatidylcholines (lecithins), both natural and synthetic. Methods to form liposomes are known in the art. See, for example, Prescott, Ed., Methods in Cell Biology, Volume XIV, Academic Press, New York, N. W., p. 33 et seq. (1976).

Compressed gases may be used to disperse the compound of the invention in aerosol form. Inert gases suitable for this purpose include nitrogen and carbon dioxide. Other suitable pharmaceutical excipients and their formulations are described in Remington's Pharmaceutical Sciences, edited by E. W. Martin (Mack Publishing Company, 18th ed., 1990).

For delivery via inhalation the compound can be formulated as liquid solutions, suspensions, aerosol propellants or dry powder and loaded into a suitable dispenser for administration. There are several types of pharmaceutical inhalation devices, nebulizers, inhalers, metered dose inhalers (MDI) and dry powder inhalers (DPI). Nebulizer devices produce a stream of high velocity air that causes the therapeutic agents (which are formulated in a liquid form) to spray as a mist that is carried into the subject's respiratory tract. MDIs typically are formulation packaged with a compressed gas. Upon actuation, the device discharges a measured amount of therapeutic agent by the compressed gas, thus affording a reliable method of administering a set amount of the agent. DPI dispenses therapeutic agents in the form of a free flowing powder that can be dispersed in the subject's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The compound according to the invention can be used alone or, if required, in combination with other active ingredients. The pharmaceutical composition of the invention comprises at least one compound according to the invention and one or more further active ingredients, in particular for treating and/or preventing a disorder associated with leptin resistance.

As used herein, using ingredients "in combination" or "combining" ingredients means not only using a dosage form comprising all the ingredients or using a combination of dosage forms comprising each ingredient separately, but also administering each ingredient at the same time or different times as long as the ingredients are used for preventing and/or treating the same disorder. Two or more further active ingredients may be used in combination.

Suitable active ingredients for combination are, for example, active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics, for example aspirin, antidepressants, and other psychopharmaceuticals, in particular active ingredients which modulate lipid metabolism, antidiabetics, hypotensive agents, and antithrombotic agents. Particularly suitable active ingredients for combination are leptin receptor agonists such as leptin.

Active ingredients which modulate lipid metabolism include, for example, HMG-CoA reductase inhibitors (e.g., statins such as lovastatin, simvastatin, pravastatin, fluvastatin, atorvastatin, rosuvastatin, or pitavastatin), inhibitors of HMG-CoA reductase expression, squalene synthesis inhibitors (e.g., BMS-188494 or TAK-475), ACAT inhibitors (e.g., avasimibe, melinamide, pactimibe, eflucimibe, or SMP-797), LDL receptor inductors, cholesterol absorption inhibitors (e.g., ezetimibe, tiqueside, or pamaqueside), polymeric bile acid adsorbers (e.g., cholestyramine, colestipol, colesolvam, CholestaGel, or colestimide), bile acid reabsorption inhibitors (e.g., ASBT (=IBAT) inhibitors such as AZD-7806, S-8921, AK-105, BARI-1741, SC-435 or, SC-635), MTP inhibitors (e.g., implitapide, BMS-201038, R-103757, or JTT-130), lipase inhibitors (e.g., orlistat), LpL activators, fibrates, niacin receptor agonists (e.g., niacin, acipimox, acifran, or radecol), CETP inhibitors (e.g., dalcetrapib, BAY 60-5521, anacetrapib, or CETP vaccine), PPAR-α agonists (e.g., fibrates such as bezafibrate, ciprofibrate, clofibrate, or fenofibrate, GW7647, leukotriene $B_4$, oleylethanolamide, tetradecylthioacetic acid, WY-14643, GW6471, or MK-886), PPAR-γ agonists (e.g., thiazolidinediones such as pioglitazone or rosiglitazone), PPAR-δ agonists (e.g., GW-501516 or BAY 68-5042), RXR modulators, FXR modulators, LXR modulators, thyroid hormones and/or thyroid mimetics (e.g., such as D-thyroxine or 3,5,3'-triiodothyronine (T3)), ATP citrate lyase inhibitors, Lp(a) antagonists, cannabinoid receptor 1 antagonists (e.g., rimonabant or SR-147778), leptin receptor agonists (e.g., leptin), bombesin receptor agonists, histamine receptor agonists, and antioxidants/radical scavengers (e.g., probucol, AGI-1067, BO-653, or AEOL-10150).

Antidiabetics are to be understood as meaning insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients include sulfonylureas (e.g., tolbutamide, glibenclamide, glimepiride, glipizide, or gliclazide), biguanides (e.g., metformin), meglitinide derivatives (e.g., repaglinide or nateglinide), glucosidase inhibitors (e.g., miglitol or acarbose) and PPAR-gamma agonists. Antidiabetics include SGLT2 inhibitors (e.g., ipragliflozin, luseogliflozin, dapagliflozin, or tofogliflozin), inhibitors of dipeptidyl-peptidase IV (DPP-IV inhibitors) (e.g., sitagliptin or vildagliptin), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake, and also potassium channel openers, such as, for example, those disclosed in WO 97/26265 and WO 99/03861.

Hypotensive active ingredients include calcium antagonists (e.g., nifedipine, amlodipine, verapamil, or diltiazem), angiotensin AII antagonists (e.g., losartan, valsartan, candesartan, embusartan, olmesartan, or telmisartan), ACE inhibitors (e.g., enalapril, captopril, lisinopril, ramipril, delapril, fosinopril, quinopril, perindopril, or trandopril), renin inhibitors, beta-receptor blockers (e.g., propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol, or bucindolol), alpha-receptor blockers (e.g., prazosin), diuretics (e.g., furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride, or triamteren), aldosterone or mineralocorticoid receptor antagonists (e.g., spironolactone or eplerenone), ECE inhibitors, ACE/NEP inhibitors, and vasopeptidase inhibitors.

Antithrombotic agents include platelet aggregation inhibitors (e.g., aspirin, clopidogrel, ticlopidine, or dipyridamol), thrombin inhibitors (e.g., ximelagatran, melagatran, dabigatran, bivalirudin, or clexane), GPIIb/IIIa antagonists (e.g., tirofiban or abciximab), factor Xa inhibitors (e.g., rivaroxaban, DU-176b, apixaban, otamixaban, fidexaban, razaxaban, fondaparinux, idraparinux, PMD-3112, YM-150, KFA-1982, EMD-503982, MCM-17, MLN-1021, DX9065a, DPC906, JTV803, SSR-126512, or SSR-128428), heparin or low molecular weight (LMW) heparin derivatives, vitamin K antagonists (e.g., coumarin), and anticoagulants.

In another aspect, the present invention provides a compound of formula (I):

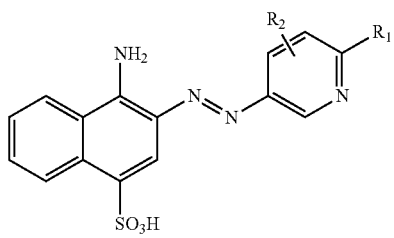

wherein $R_1$ is aryl or heteroaryl, wherein the aryl or heteroaryl may be substituted with 1 to 3 substituents selected from the group consisting of halo, hydroxy, alkyl, halo-substituted alkyl, aryl, halo- or alkyl-substituted aryl, alkoxy, hydroxy- or carboxy-substituted alkoxy, alkylthio, aryloxy, CHO, C(O)-alkyl, C(O)-aryl, C(O)-alkylene-carboxyl, C(O)-alkylene-carboxy ester, cyano, oxo, heterocycloalkyl, and heteroaryl-substituted alkoxy, and $R_2$ is hydrogen, halo, alkyl, phenyl, or pyridyl, or an oxide, ester, prodrug, pharmaceutically acceptable salt, or solvate thereof for use in improving lipid metabolism and/or treating and/or preventing steatosis, as well as a pharmaceutical composition comprising at least one of them.

"Improving lipid metabolism" as used herein means preventing blood total cholesterol level, HDL cholesterol level, LDL cholesterol level, free fatty acid level, and/or triglyceride level from deviating from normal range, as well as normalizing blood total cholesterol level, HDL cholesterol level, LDL cholesterol level, free fatty acid level, and/or triglyceride level that deviate from the normal range.

In an embodiment of the last aspect, the compound of the invention is a compound of formula (I), wherein $R_1$ is aryl or heteroaryl, wherein the aryl or heteroaryl may be substituted with 1 to 3 substituents selected from the group consisting of halo, hydroxy, alkyl, halo-substituted alkyl, aryl, halo- or alkyl-substituted aryl, alkoxy, hydroxy- or carboxy-substituted alkoxy, aryloxy, CHO, C(O)-alkyl, C(O)-aryl, C(O)-alkylene-carboxyl, C(O)-alkylene-carboxy ester, cyano, heterocycloalkyl, and heteroaryl-substituted alkoxy, and $R_2$ is hydrogen, alkyl, phenyl, or pyridyl, or an oxide, ester, prodrug, pharmaceutically acceptable salt, or solvate thereof.

In an embodiment of the last aspect, the compound of the invention is a compound of formula (I), wherein $R_1$ is phenyl which may be substituted with 1 to 3 substituents independently selected from the group consisting of halo, hydroxy, alkyl, halo-substituted alkyl, aryl, halo- or alkyl-substituted aryl, alkoxy, hydroxy- or carboxy-substituted alkoxy, alkylthio, aryloxy, CHO, C(O)-alkyl, C(O)-aryl, C(O)-alkylene-carboxyl, C(O)-alkylene-carboxy ester, cyano, heterocycloalkyl, and heteroaryl-substituted alkoxy, or an oxide, ester, prodrug, pharmaceutically acceptable salt, or solvate thereof.

In an embodiment of the last aspect, the compound of the invention is a compound of formula (I), wherein $R_1$ is phenyl which may be substituted with 1 to 3 substituents independently selected from the group consisting of halo, hydroxy, alkyl, halo-substituted alkyl, aryl, halo- or alkyl-substituted aryl, alkoxy, hydroxy- or carboxy-substituted alkoxy, aryloxy, CHO, C(O)-alkyl, C(O)-aryl, C(O)-alkylene-carboxyl, C(O)-alkylene-carboxy ester, cyano, heterocycloalkyl, and heteroaryl-substituted alkoxy, or an oxide, ester, prodrug, pharmaceutically acceptable salt, or solvate thereof.

In an embodiment of the last aspect, the compound of the invention is a compound of formula (I), wherein $R_1$ is phenyl which may be substituted with 1 to 3 substituents independently selected from the group consisting of halo, hydroxy, alkyl, halo-substituted alkyl, alkoxy, alkylthio, phenyl, halo- or alkyl-substituted phenyl, pyridyl, and morpholinyl, or an oxide, ester, prodrug, pharmaceutically acceptable salt, or solvate thereof.

In an embodiment of the last aspect, the compound of the invention is a compound of formula (I), wherein
$R_1$ is phenyl which may be substituted with 1 to 3 substituents independently selected from the group consisting of halo, hydroxy, alkyl, halo-substituted alkyl, alkoxy, phenyl, halo- or alkyl-substituted phenyl, pyridyl, and morpholinyl,
or an oxide, ester, prodrug, pharmaceutically acceptable salt, or solvate thereof.

In an embodiment of the last aspect, the compound of the invention is a compound of formula (I), wherein
$R_1$ is phenyl which may be substituted with 1 to 3 substituents independently selected from the group consisting of halo, alkyl, halo-substituted alkyl, alkoxy, and alkylthio,
or an oxide, ester, prodrug, pharmaceutically acceptable salt, or solvate thereof.

In an embodiment of the last aspect, the compound of the invention is a compound of formula (I), wherein
$R_1$ is phenyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is phenyl which is substituted with halo and alkyl,
or an oxide, ester, prodrug, pharmaceutically acceptable salt, or solvate thereof.

In an embodiment of the last aspect, the compound of the invention is a compound of formula (I), wherein
$R_1$ is phenyl which is substituted with fluoro and methyl,
or an oxide, ester, prodrug, pharmaceutically acceptable salt, or solvate thereof.

In an embodiment of the last aspect, the compound of the invention is a compound of formula (I), wherein
$R_1$ is naphthyl, fluorenyl, furanyl, benzofuranyl, dibenzofuranyl, thiophenyl, benzothiophenyl, dibenzothiophenyl, pyrrolyl, indolyl, carbazole, benzothiazole, oxazole, isoxazole, pyridyl, quinolyl, isoquinolyl, thianthrenyl, phenoxathiinyl, phenothiazyl, or phenoxazyl which may be substituted with 1 to 3 substituents independently selected from the group consisting of halo, oxo, and alkyl,
or an oxide, ester, prodrug, pharmaceutically acceptable salt, or solvate thereof.

In an embodiment of the last aspect, the compound of the invention is a compound of formula (I), wherein
$R_1$ is naphthyl, furanyl, benzofuranyl, dibenzofuranyl, thiophenyl, benzothiophenyl, dibenzothiophenyl, pyrrolyl, indolyl, carbazole, oxazole, isoxazole, pyridyl, quinolyl, isoquinolyl, thianthrenyl, phenoxathiinyl, phenothiazyl, or phenoxazyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is naphthyl, benzofuranyl, dibenzofuranyl, benzothiophenyl, dibenzothiophenyl, indolyl, carbazole, benzothiazole, quinolyl, isoquinolyl, thianthrenyl, phenoxathiinyl, phenothiazyl, or phenoxazyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is naphthyl, benzofuranyl, dibenzofuranyl, benzothiophenyl, dibenzothiophenyl, indolyl, carbazole, quinolyl, isoquinolyl, thianthrenyl, phenoxathiinyl, phenothiazyl, or phenoxazyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is benzofuranyl, dibenzofuranyl, benzothiophenyl, dibenzothiophenyl, or thianthrenyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is dibenzofuranyl, benzothiophenyl, dibenzothiophenyl, carbazole, benzothiazole or thianthrenyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is dibenzofuranyl, benzothiophenyl, dibenzothiophenyl, or thianthrenyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is benzothiophenyl or dibenzothiophenyl which may be substituted with 1 to 3 substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is dibenzothiophenyl which may be substituted with 1 to 3substituents independently selected from the group consisting of halo and alkyl,
or an oxide, ester, prodrug, pharmaceutically acceptable salt, or solvate thereof.

In an embodiment of the last aspect, the compound of the invention is a compound of formula (I), wherein
$R_1$ is unsubstituted benzothiophenyl or dibenzothiophenyl,
or an oxide, ester, prodrug, pharmaceutically acceptable salt, or solvate thereof.

In an embodiment of the last aspect, the compound of the invention is a compound of formula (I), wherein
$R_1$ is unsubstituted dibenzothiophenyl,
or an oxide, ester, prodrug, pharmaceutically acceptable salt, or solvate thereof.

In an embodiment of the last aspect, the compound of the invention is a compound of formula (I), wherein
$R_2$ is hydrogen, halo or alkyl,
or an oxide, ester, prodrug, pharmaceutically acceptable salt, or solvate thereof.

In an embodiment of the last aspect, the compound of the invention is a compound of formula (I), wherein $R_2$ is hydrogen or alkyl, or an oxide, ester, prodrug, pharmaceutically acceptable salt, or solvate thereof.

In an embodiment of the last aspect, the compound of the invention is a compound of formula (I), wherein $R_2$ is hydrogen, or an oxide, ester, prodrug, pharmaceutically acceptable salt, or solvate thereof.

In an embodiment of the last aspect, the compound of the invention is a compound selected from Compounds 1 to 76 listed in Table 1 above, or a free acid form, oxide, ester, prodrug, pharmaceutically acceptable salt, or solvate thereof.

In an embodiment of the last aspect, the compound of the invention is the compound of the formula

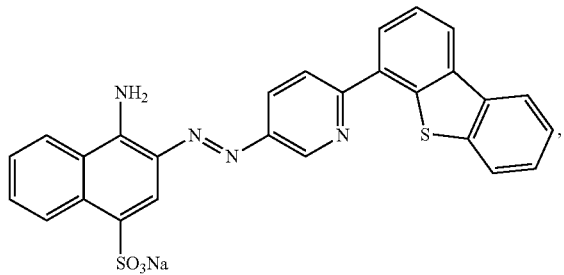

which is Compound 57 listed in Table 1 above, or an oxide, ester, prodrug, pharmaceutically acceptable salt, or solvate thereof, particularly a sodium salt thereof.

EXAMPLES

The following Examples illustrate the present invention, but not limit the scope thereof.

Synthesis Examples

Synthesis Example 1

Synthesis of Compound 32: 4-amino-3-[6-(4-fluoro-2-methylphenyl)pyridine-3-ylazo]naphthalene-1-sulfonic acid sodium salt

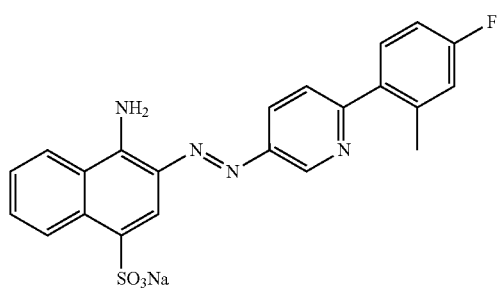

(i) 2-(4-Fluoro-2-methylphenyl)-5-nitropyridine

2-Chloro-5-nitropyridine (5.0 g, 31.5 mmol) and tetrakis(triphenylphosphine)palladium (0.35 g, 0.3 mmol) were added to 1,2-dimethoxyethan (50 ml), then degassed and purged with nitrogen three times under reduced pressure. Under nitrogen atmosphere the mixture was stirred at room temperature for 20 minutes, 4-fluoro-2-methylphenylboronic acid (31.5 mmol) and 2M aqueous sodium carbonate (31.5 ml) were poured in, and the temperature was raised to 80° C. After the reaction at 80° C. for 3 hours, the mixture was cooled to room temperature and extracted with addition of ethyl acetate and water. The organic layer was dried with anhydrous sodium sulfate, and concentrated under reduced pressure. The products were purified by column chromatography to give the title compound.

(ii) 6-(4-Fluoro-2-methylphenyl)pyridine-3-ylamine

Ethanol (20 ml) and water (5 ml) was mixed, added with iron powder, and heated to 70-80° C. Ammonium chloride (0.1 g, 2.1 mmol) was added, followed by 2-(4-fluoro-2-methylphenyl)-5-nitropyridine (10.0 mmol) obtained in (i). The reaction was carried out at 70-80° C. for 1 hour. After the completion of the reaction, the iron powder was filtered while hot through Celite, and the filtrate was concentrated under reduced pressure. The residue was dissolved in isopropyl alcohol, crystallized and filtered with addition of water to give the title compound.

(iii) 4-Amino-3-[6-(4-fluoro-2-methylphenyl)pyridine-3-ylazo]naphthalene-1-sulfonic acid sodium salt 6-(4-Fluoro-2-methylphenyl)pyridine-3-ylamine (58.9 mmol) obtained in (ii) was dissolved in 99% acetic acid (50 ml), and added with 35% hydrochloric acid (25 g) to form hydrochloride. With cooling on ice a 36% aqueous solution of sodium nitrite (12 g, 62.5 mmol) was added dropwise at 0-5° C., and the reaction was carried out for about 15 minutes. Amide sulfuric acid was added and the reaction was carried out for additional 5 minutes, resulting in a diazo solution. 4-Amino-1-naphthalenesulfonic acid (13.0 g, 58.4 mmol) was suspended in water (130 ml), and the pH of the suspension was adjusted to pH 8 to 9 with 10% aqueous sodium hydroxide. The mixture was cooled to 5-10° C., and added dropwise with the obtained diazo solution at 5-10° C., during which 10% aqueous sodium hydroxide was added to keep the pH at 7 to 9. After the completion of the addition, the reaction was carried out at 5-10° C. for 1 hour, then the temperature was raised to room temperature. Salting-out was performed with saturated aqueous sodium chloride, and the precipitated crystals were filtered with suction. Purification by column chromatography gave the title compound.

$^1$H-NMR δ [ppm]=9.22 (1H, d, J=2.4 Hz), 8.76 (1H, d, J=8.1), 8.49-8.44 (2H, m), 8.34 (1H, s), 7.82 (2H, bs), 7.67-7.47 (4H, m), 7.21-7.11 (2H, m), 2.41 (3H, s)

$^{13}$C-NMR (DMSO-d6) δ [ppm]=163.5, 160.3, 158.2, 147.1, 146.7, 145.4, 138.8, 138.7, 136.1, 136.1, 132.4, 132.1, 131.8, 131.7, 129.2, 128.6, 128.3, 127.2, 125.1, 124.6, 124.2, 124.0, 117.3, 117.1, 116.6, 112.9, 112.6, 20.4, 20.4

Synthesis Example 2

Synthesis of Compound 57: 4-amino-3-(6-dibenzo-thiophene-4-ylpyridine-3-ylazo)naphthalene-1-sulfonic acid sodium salt

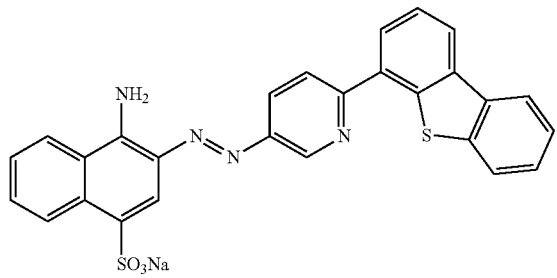

(i) 2-Dibenzothiophene-4-yl-5-nitropyridine

2-Chloro-5-nitropyridine (3.0 g, 18.9 mmol), 4-dibenzothiopheneboronic acid (4.7 g, 20.8 mmol), and tetrakis(triphenylphosphine)palladium (0.2 g, 0.2 mmol) were added to 1,2-dimethoxyethan (30 ml), then degassed and purged with nitrogen three times under reduced pressure. Under nitrogen atmosphere the mixture was stirred at room temperature for 20 minutes, then 1M aqueous sodium carbonate (40 ml) was poured in, and the temperature was raised to 80° C. After the reaction at 80° C. for 6 hours, the mixture was cooled to room temperature and crystallized with addition of water. The precipitated crystals were filtered to give the title compound.

(ii) 6-Dibenzothiophene-4-ylpyridine-3-ylamine

Ethanol (20 ml) and water (5 ml) was mixed, added with iron powder, and heated to 70-80° C. Ammonium chloride (0.1 g, 2.1 mmol) was added, followed by 2-dibenzothiophene-4-yl-5-nitropyridine (3.3 g, 10.0 mmol) obtained in (i). The reaction was carried out at 70-80° C. for 1 hour. After the completion of the reaction, the iron powder was filtered while hot through Celite, and the filtrate was concentrated under reduced pressure. The residue was dissolved in isopropyl alcohol, crystallized and filtered with addition of water to give the title compound.

(iii) 4-Amino-3-(6-dibenzothiophene-4-ylpyridine-3-ylazo)naphthalene-1-sulfonic acid sodium salt 6-Dibenzothiophene-4-ylpyridine-3-ylamine (39.5 g, 143.0 mmol) obtained in (ii) was dissolved in tetrahydrofuran/water (2600 ml), added with 98% sulfuric acid (42.5 g) to form sulfate. With cooling on ice, an aqueous solution of sodium nitrite (13.3 g, 192.5 mmol) was added dropwise at 0-5° C., and the reaction was carried out for about 15 minutes. Amide sulfuric acid was added and the reaction was carried out for additional 5 minutes, resulting in a diazo solution.

4-Amino-1-naphthalenesulfonic acid (31.6 g, 141.5 mmol) was suspended in water, and pH of the suspension was adjusted to pH 8 to 9 with 10% aqueous sodium hydroxide. The mixture was cooled to 5-10° C., and added dropwise with the obtained diazo solution at 5-10° C., during which 10% aqueous sodium hydroxide was added to keep the pH at 7 to 9. After the completion of the addition, the reaction was carried out at 5-10° C. for 1 hour, then the temperature was raised to room temperature. Under reduced pressure tetrahydrofuran was distilled off and a saturated sodium chloride solution was added. The precipitated crystals were filtered with suction, purified by column chromatography to give the title compound (29.0 g, 38.1%).

$^1$H-NMR (DMSO-d6) δ [ppm]=9.40 (1H, d, J=2.4 Hz), 8.77 (1H, d, J=8.1 Hz), 8.61 (1H, dd, J=8.7, 2.4 Hz), 8.51 (1H, J=7.8 Hz), 8.50 (1H, d, J=8.7 Hz), 8.44-8.39 (3H, m), 8.36 (1H, s), 8.10-8.07 (1H, m), 7.88 (2H, bs), 7.72-7.66 (1H, m), 7.65-7.60 (1H, m), 7.56-7.49 (3H, m)

$^{13}$C-NMR (DMSO-d6) δ [ppm]=154.7, 147.6, 147.2, 144.7, 141.6, 136.9, 136.5, 134.2, 132.5, 132.2, 132.1, 129.4, 128.7, 128.4, 127.9, 127.2, 125.6, 125.2, 125.1, 124.6, 124.3, 124.1, 123.1, 122.6, 121.9, 121.4, 116.1

Biological Test Examples

Test Example 1: Analysis of Effects of Compounds 32 and 57 to Improve Metabolism in Wild Type Mice and Transgenic Mice Overexpressing Leptin Under a High Fat Diet Condition Eight-week old male wild type mice and transgenic mice overexpressing leptin (LepTg) (Ogawa et al. Diabetes 48: 1822-1829, 1999, prepared in Department of Endocrinology and Metabolism, Kyoto University) were divided into three treatment groups, respectively: "standard diet (SD)+vehicle (V)", "60% high fat diet (HFD)+vehicle", and "60% high fat diet+Compound 57". The mice were kept for four weeks with ad libitum feeding, and the body weight and the food intake of the mice were measured. The vehicle and Compound 57 were administered to the mice by intraperitoneal injection once a day. The dosage of Compound 57 was 50 mg/kg/day. After the four weeks the mice were sacrificed and blood, epididymal adipose tissues, and the liver were collected. The weight of the adipose tissues, the liver weight, the liver triglyceride levels, and the plasma levels of glucose, insulin, total cholesterol (T-chol), triglyceride (TG), and nonesterified fatty acid (NEFA) were measured (n=5 for each group). The equivalent dosage of Compound 32 was tested in a similar manner (n=5 for each group).

The body weight of the transgenic mice was lower than that of the wild type mice before they were fed with the high fat diet (FIG. 1, left). The weight gain caused by the high fat diet was more remarkable in the transgenic mice than in the wild type mice. After the four weeks, the body weight of the transgenic mice was as high as that of the wild type mice. The body weight of the wild type mice and the transgenic mice administered with Compound 57 or 32 did not increase under the high fat diet condition. The food intake of the wild type mice and the transgenic mice administered with Compound 57 or 32 did not increase under the high fat diet condition (FIG. 1, right).

The weight of the adipose tissues increased under the high fat diet condition in the wild type mice and the transgenic mice, but did not increase in the mice administered with Compound 57 or 32 in the both groups (FIG. 2, left). The liver weight and liver triglyceride levels were analyzed as indicators of steatosis (FIG. 2, middle and right). The liver weight and the liver triglyceride levels increased under the high fat diet condition in the wild type mice and the transgenic mice, but did not increase in the mice administered with Compound 57 or 32 in the both groups.

Figure 3:
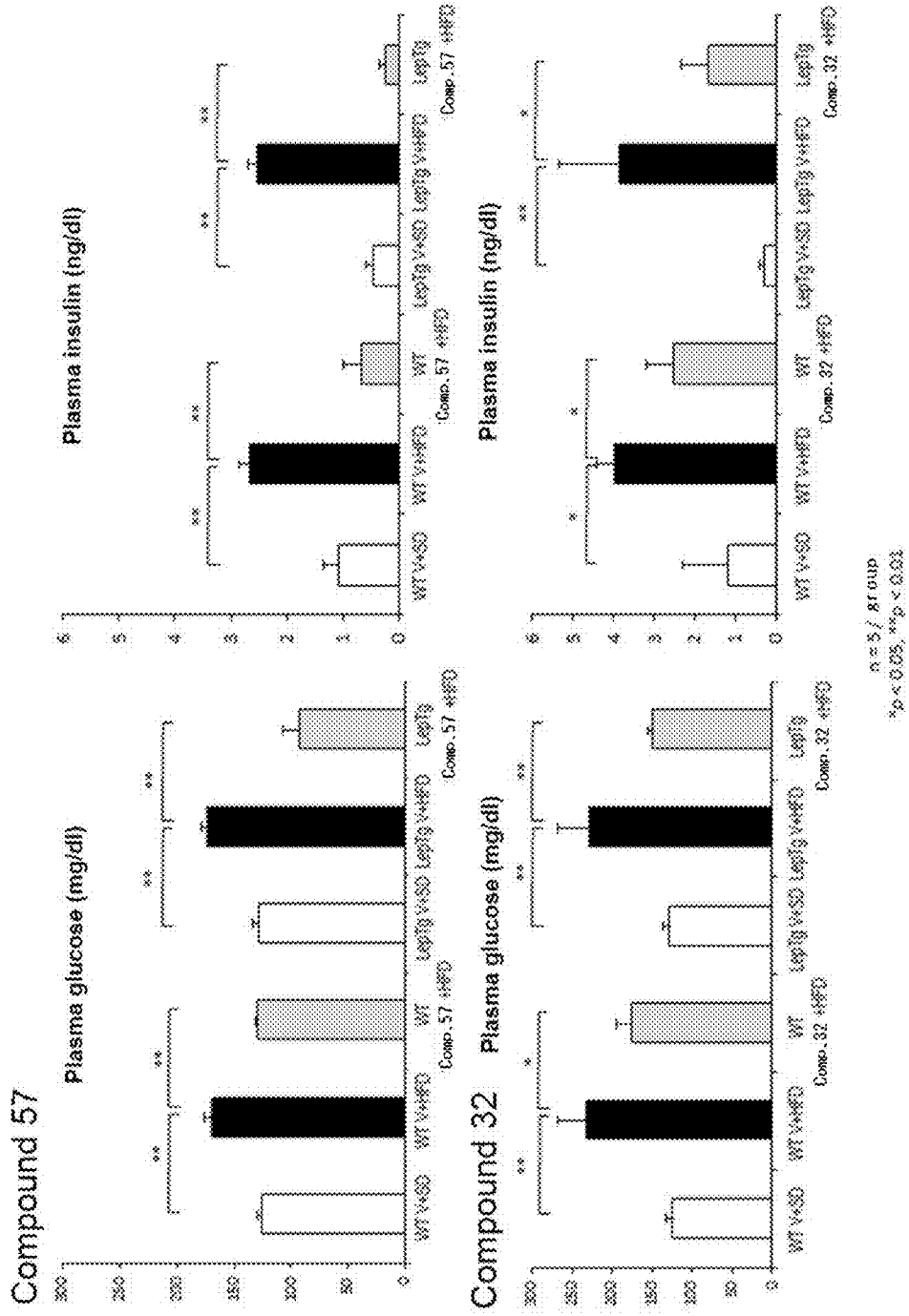
FIG. 3 shows the effects of Compounds 57 and 32 to improve insulin resistance in the wild type and the LepTg mice under the high fat diet condition.

Regarding glucose metabolism, the random plasma glucose levels and the plasma insulin levels increased under the high fat diet condition in the wild type mice and the transgenic mice, but did not increase in the mice administered with Compound 57 or 32 in the both groups (FIG. 3).

Figure 4:
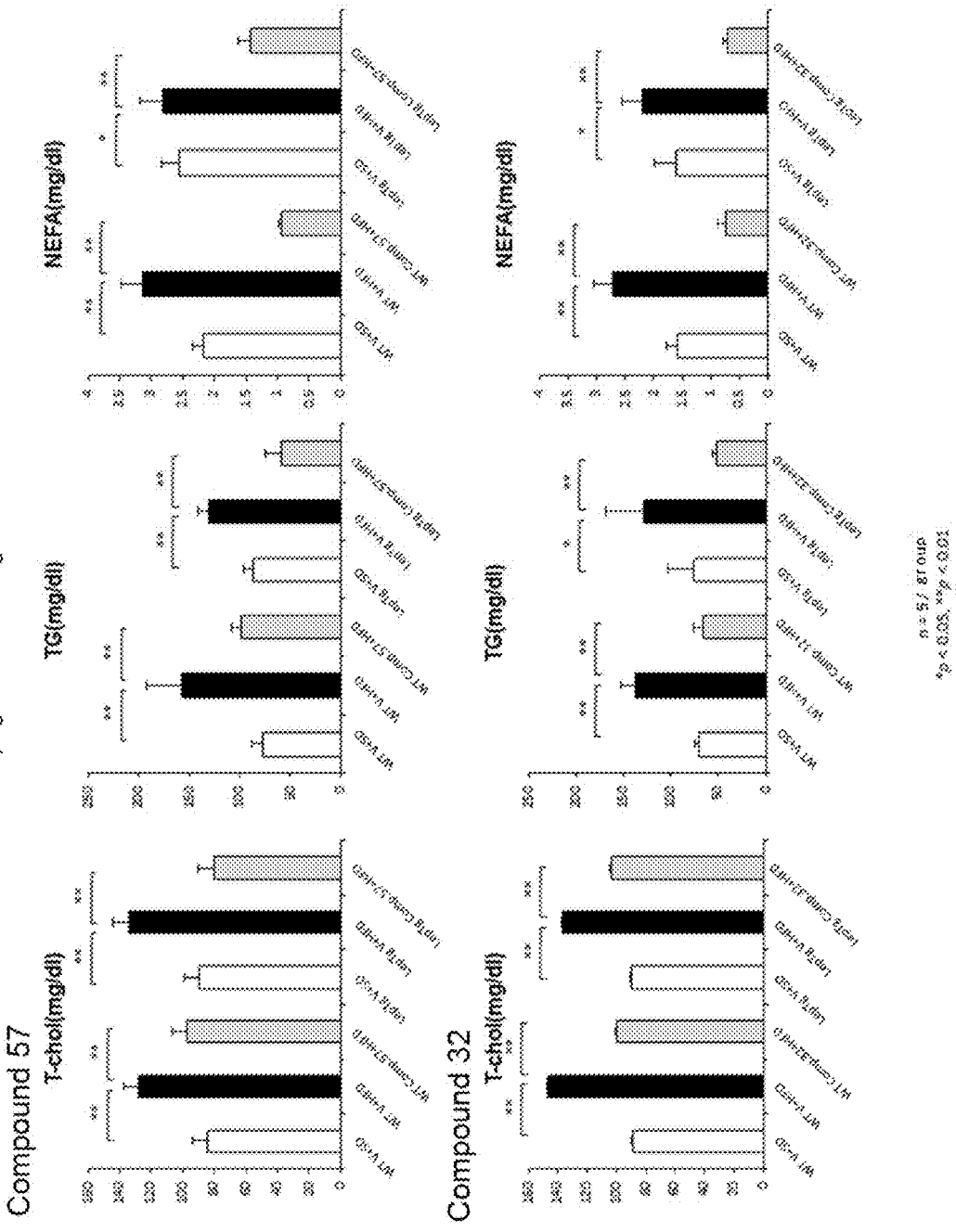
FIG. 4 shows the effects of Compounds 57 and 32 to improve lipid metabolism in the wild type and the LepTg mice under the high fat diet condition.

Regarding lipid metabolism, the plasma levels of total cholesterol, triglyceride, and nonesterified fatty acid were analyzed (FIG. 4). They increased under the high fat diet condition in the wild type mice and the transgenic mice, but did not increase in the mice administered with Compound 57 or 32 in the both groups.

High fat diet is generally known to induce leptin resistance. It has been reported that leptin resistance is strongly induced in LepTg mice fed with high fat diet. In this study the high fat diet caused the remarkable weight gain in the transgenic mice overexpressing leptin up to the same level as that of the wild type mice. The result suggests that a condition wherein leptin is ineffective in spite of its overexpression, leptin resistance, was induced. Though the high fat diet increased the body weight, the food intake, the weight of the adipose tissues, the liver weight, the liver triglyceride levels, and the plasma levels of glucose and insulin in the wild type mice and the transgenic mice, the increases were suppressed by the administration of Compound 57 or 32. In the treated mice these parameters were as low as those of the mice fed with the standard diet, in which no leptin resistance developed. The results mean that the compounds prevent development of leptin resistance.

Test Example 2: Analysis of Effects of Compounds 32 and 57 to Improve Metabolism in Leptin-Deficient Ob/Ob Mice Ob/ob mice cannot produce leptin due to a mutation in the leptin gene (Zhang et al. Nature 372: 425-432, 1994). Eight-week old male ob/ob mice, purchased from CHARLES RIVER LABORATORIES JAPAN, INC., were divided into two treatment groups: "Vehicle (V)" and "Compound 57". The mice were kept for four weeks with ad libitum feeding of standard diet (SD), and the body weight and the food intake of the mice were measured. The vehicle and Compound 57 were administered to the mice by intraperitoneal injection once a day. The dosage of Compound 57 was 50 mg/kg/day. After the four weeks the mice were sacrificed and blood, epididymal adipose tissues, and the liver were collected. The weight of the adipose tissues, the liver weight, the liver triglyceride levels, and the plasma levels of glucose, insulin, total cholesterol (T-chol), triglyceride (TG) and nonesterified fatty acid (NEFA) were measured (n=5 for each group). The equivalent dosage of Compound 32 was tested in a similar manner (n=5 for each group).

Figure 5:
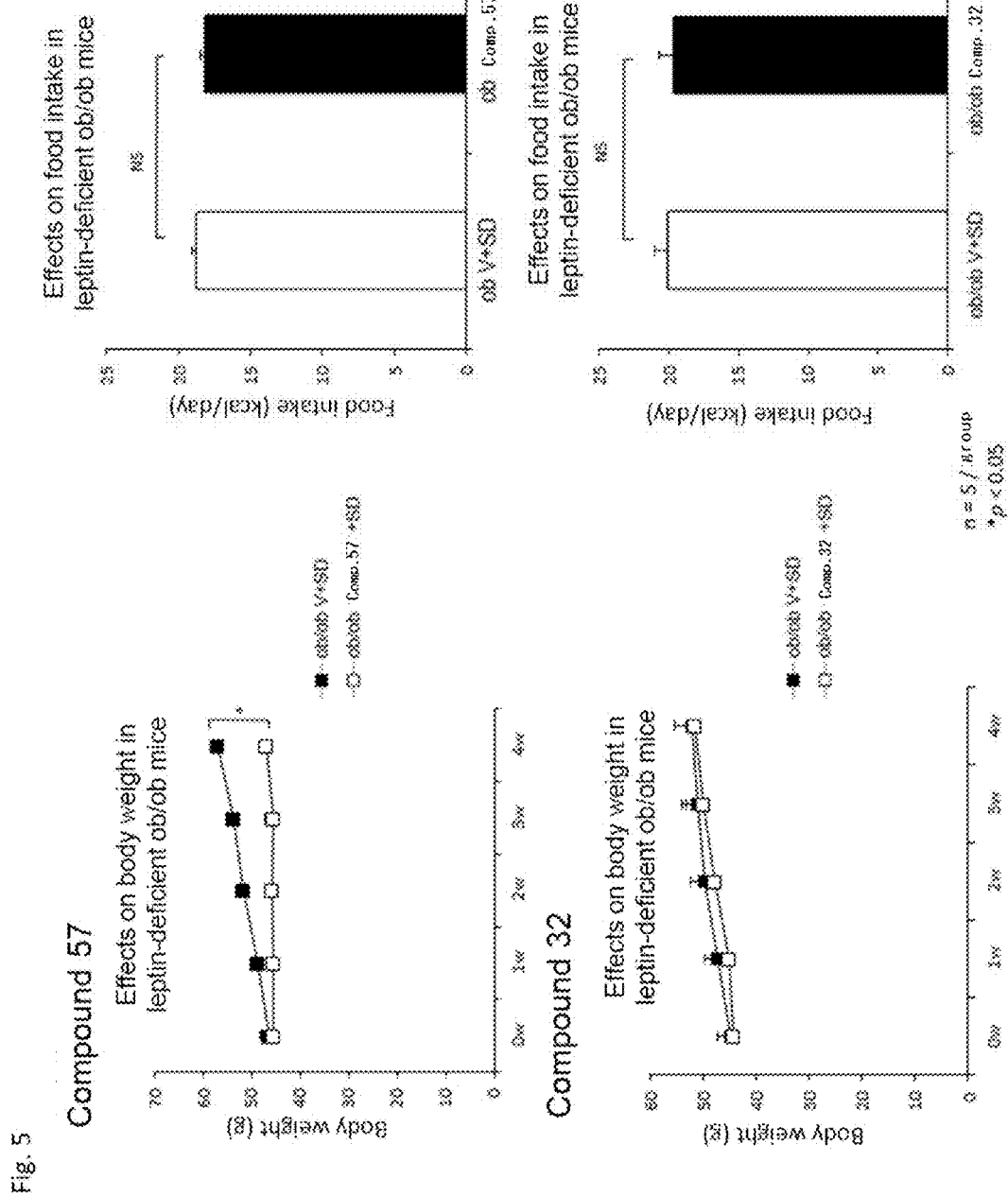
FIG. 5 shows the effects of Compounds 57 and 32 on the body weight and the food intake in the leptin-deficient ob/ob mice.

The administration of Compound 57 decreased the body weight in the ob/ob mice, but Compound 32 did not (FIG. 5, left). The food intake did not change in the either groups administered with Compound 57 or 32 (FIG. 5, right). The weight of the adipose tissues decreased in the group administered with Compound 57, but did not change in the group administered with Compound 32 (FIG. 6, left). The liver weight and the liver triglyceride levels, indicators of steatosis, decreased in the group administered with Compound 57, but did not change in the group administered with Compound 32 (FIG. 6, middle and right). Regarding glucose metabolism, the random plasma glucose levels and the plasma insulin levels did not change in the both groups (FIG. 7). Regarding lipid metabolism, Compound 57 decreased the total cholesterol levels and the nonesterified fatty acid levels, but did not clearly change the triglyceride levels (FIG. 8, upper panels). Compound caused no clear change in these parameters (FIG. 8, lower panels).

In Test Example 2 the effects of Compounds 57 and 32 in the absence of leptin were tested. Compound 57 did not change the food intake and the plasma levels of glucose, insulin, and triglyceride, but decreased the body weight, the weight of the adipose tissues, the liver weight, the liver triglyceride levels, and the plasma levels of total cholesterol, and nonesterified fatty acid. Compound 32 did not change these parameters. The results suggest that in Test Example 1 Compounds 57 and 32 suppressed the increase of the parameters such as the body weight through a leptin-dependent effect, for example the effect to suppress food intake. The results also suggest the possibility that Compound 57 has a leptin-independent effect to improve lipid metabolism, for example an effect to decrease lipid in blood or tissues, in addition to the effect to improve leptin resistance.

Test Example 3: Analysis of Effects of Compounds 32 and 57 to Improve Metabolism in A-ZIP/F-1 Mice, a Model of Generalized Lipodystrophy A-ZIP/F-1 mice, which are used as a model of generalized lipodystrophy, have substantially no white adipocyte and thus cannot produce leptin (Moitra et al. Genes Dev 12: 3168-3181, 1998). Eight-week old male A-ZIP/F-1 mice, gifted from Dr. Reitman of National Institutes of Health, were divided into two treatment groups: "Vehicle (V)" and "Compound 57". The mice were kept for four weeks with ad libitum feeding of standard diet (SD), and the body weight and the food intake of the mice were measured. The vehicle and Compound 57 were administered to the mice by intraperitoneal injection once a day. The dosage of Compound 57 was 50 mg/kg/day. After the four weeks the mice were sacrificed and blood, epididymal adipose tissues, and the liver were collected. The weight of the adipose tissues, the liver weight, the liver triglyceride levels, the plasma levels of glucose, insulin, total cholesterol (T-chol), triglyceride (TG) and nonesterified fatty acid (NEFA) were measured (n=5 for each group). The equivalent dosage of Compound 32 was tested in a similar manner (n=5 for each group).

The administration of Compound 57 slightly decreased the body weight in the A-ZIP/F-1 mice, but Compound 32 did not (FIG. 9, left). The food intake did not change in the either groups administered with Compound 57 or 32 (FIG. 9, right). The weight of the adipose tissues cannot be estimated because the mice are a model of generalized lipodystrophy (FIG. 10, left). The liver weight and the liver triglyceride levels, the indicators of steatosis, decreased in the group administered with Compound 57, but did not change in the group administered with Compound 32 (FIG. 10, middle and right). Regarding glucose metabolism, the random plasma glucose levels and the plasma insulin levels did not change in the both groups (FIG. 11). Regarding lipid metabolism, Compound 57 decreased the levels of total cholesterol, triglyceride, and nonesterified fatty acid, but Compound 32 did not change these parameters (FIG. 12).

In Test Example 3, as in Test Example 2, the effects of Compounds 57 and 32 in the absence of leptin were tested. Compound 57 did not change the food intake and the plasma levels of glucose and insulin, but decreased the body weight, the liver weight, the liver triglyceride levels, and the plasma levels of total cholesterol, triglyceride and nonesterified fatty acid. Compound 32 did not cause the improvement of leptin resistance, which was observed in Test Example 1. The results suggest that in Test Example 1 Compounds 57 and 32 suppressed the increase of the parameters such as the body weight through a leptin-dependent effect, for example the effect to suppress food intake. The results also suggest the possibility that Compound 57 has a leptin-independent effect to improve lipid metabolism, for example an effect to decrease lipid in blood or tissues, in addition to the effect to improve leptin resistance.

Test Example 4: Analysis of Effects of Compounds 32 and 57 to Improve Metabolism in Mice Having Diet-Induced Obesity Caused by a High Fat Diet Eight-week old male wild type mice and transgenic mice overexpressing leptin (LepTg) (see Test Example 1) were divided into two groups, respectively (n=4 and 12), and kept for four weeks under a standard diet (SD) or a high fat diet (HFD) condition. All the mice fed with the standard diet for the four weeks were assigned to the group "vehicle (V)" and fed with the standard diet for further four weeks, and then the body weight and the food intake of the mice were measured. The mice fed with the high fat diet for the four weeks were divided into three groups: "vehicle (V)", "Compound 57", and "Compound 32", and fed with the high fat diet for further four weeks, and then the body weight and the food intake of the mice were measured. The vehicle, Compound 57, and Compound 32 were administered to the mice by intraperitoneal injection once a day. The each dosage of Compounds 57 and 32 was 50 mg/kg/day. Finally the mice were sacrificed and blood, epididymal adipose tissues, and the liver were collected. The weight of the adipose tissues, the liver weight, and the plasma levels of glucose and triglyceride were measured (n=4 for each group).

Figure 13:
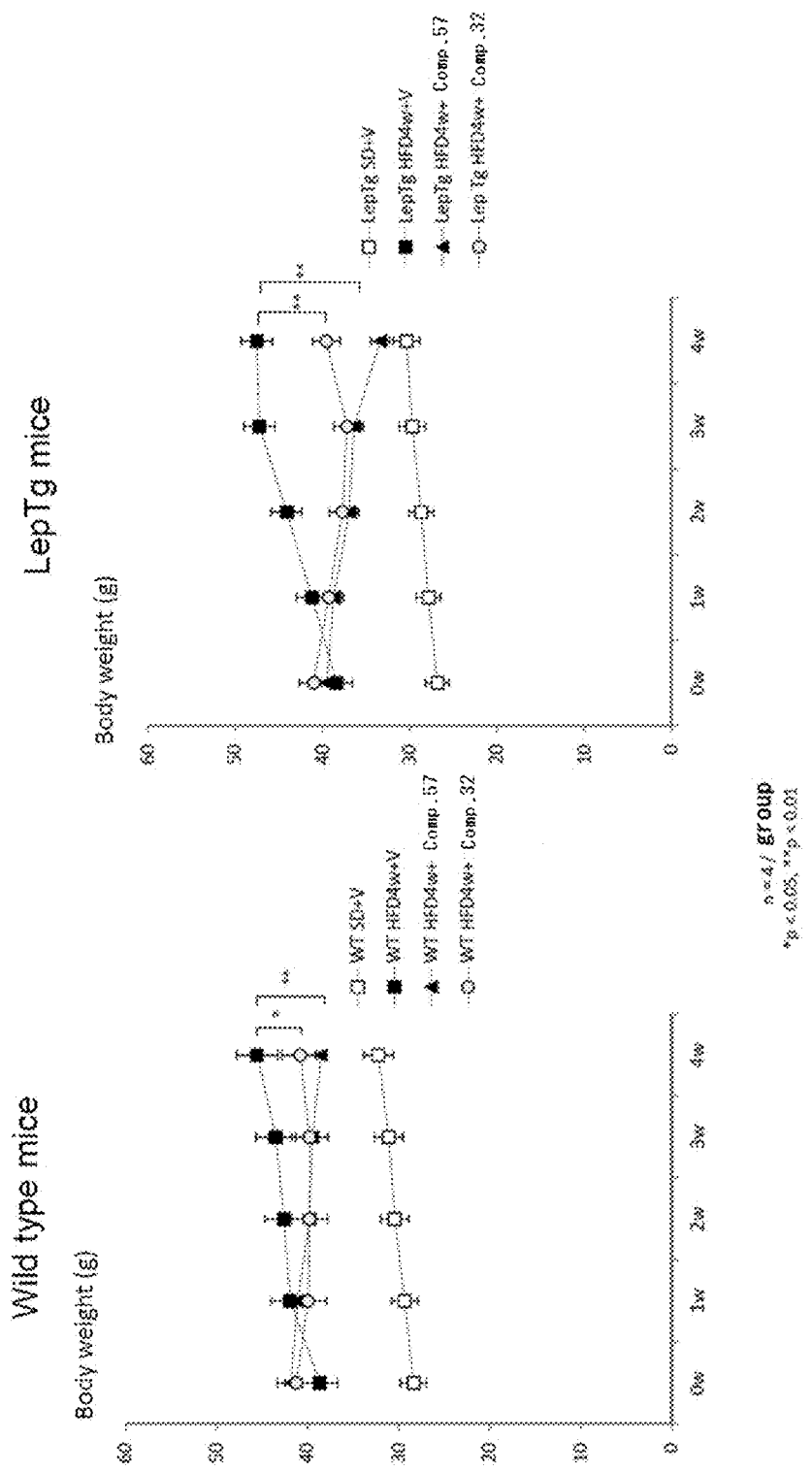
FIG. 13 shows the effects of Compounds 57 and 32 to decrease the body weight in the mice having diet-induced obesity.
Figure 14:
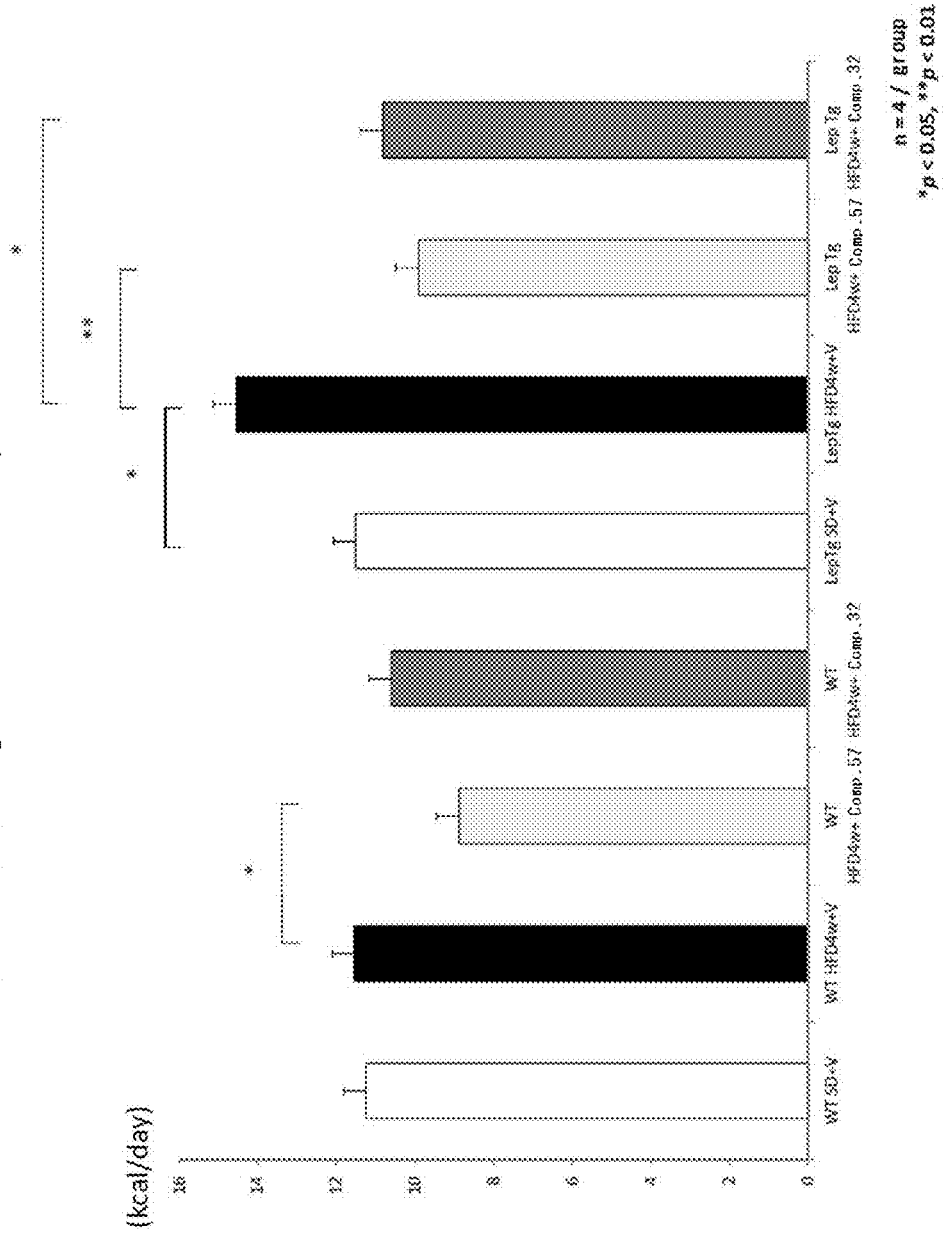
FIG. 14 shows the effects of Compounds 57 and 32 to suppress the food intake in the mice having diet-induced obesity.
Figure 15:
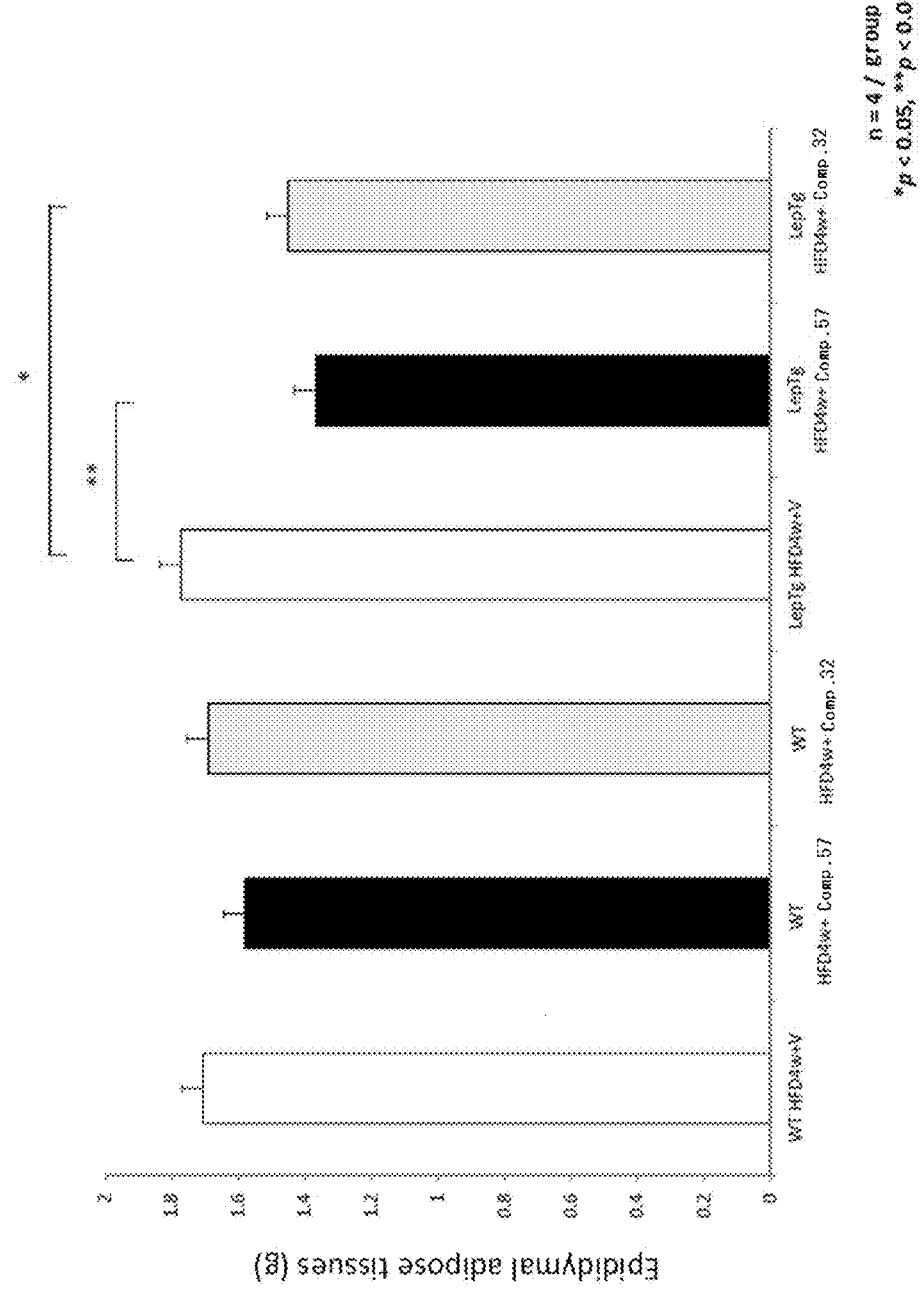
FIG. 15 shows the effects of Compounds 57 and 32 to decrease the adipose tissues in the mice having diet-induced obesity.
Figure 16:
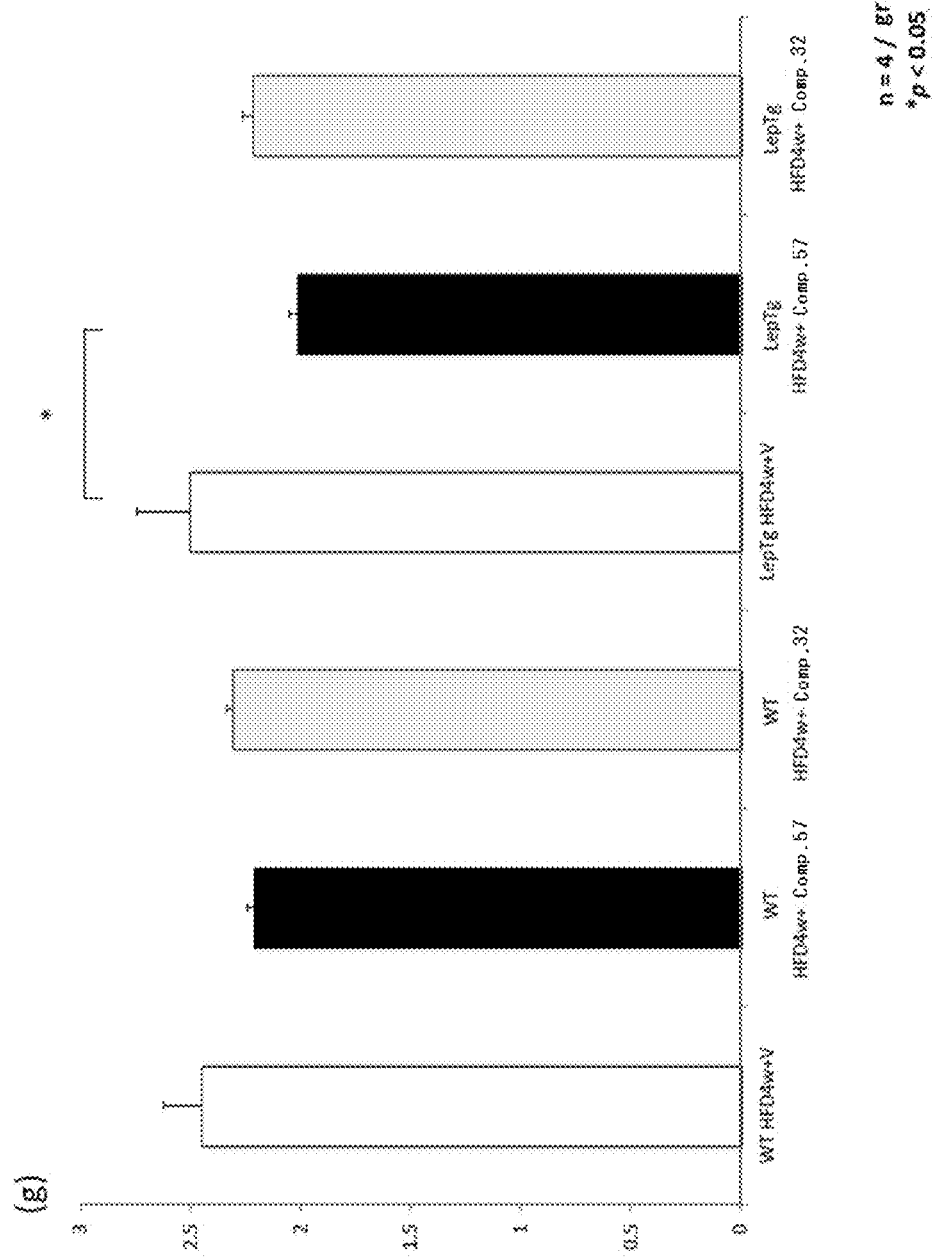
FIG. 16 shows the effects of Compounds 57 and 32 to decrease the liver weight in the mice having diet-induced obesity.
Figure 17:
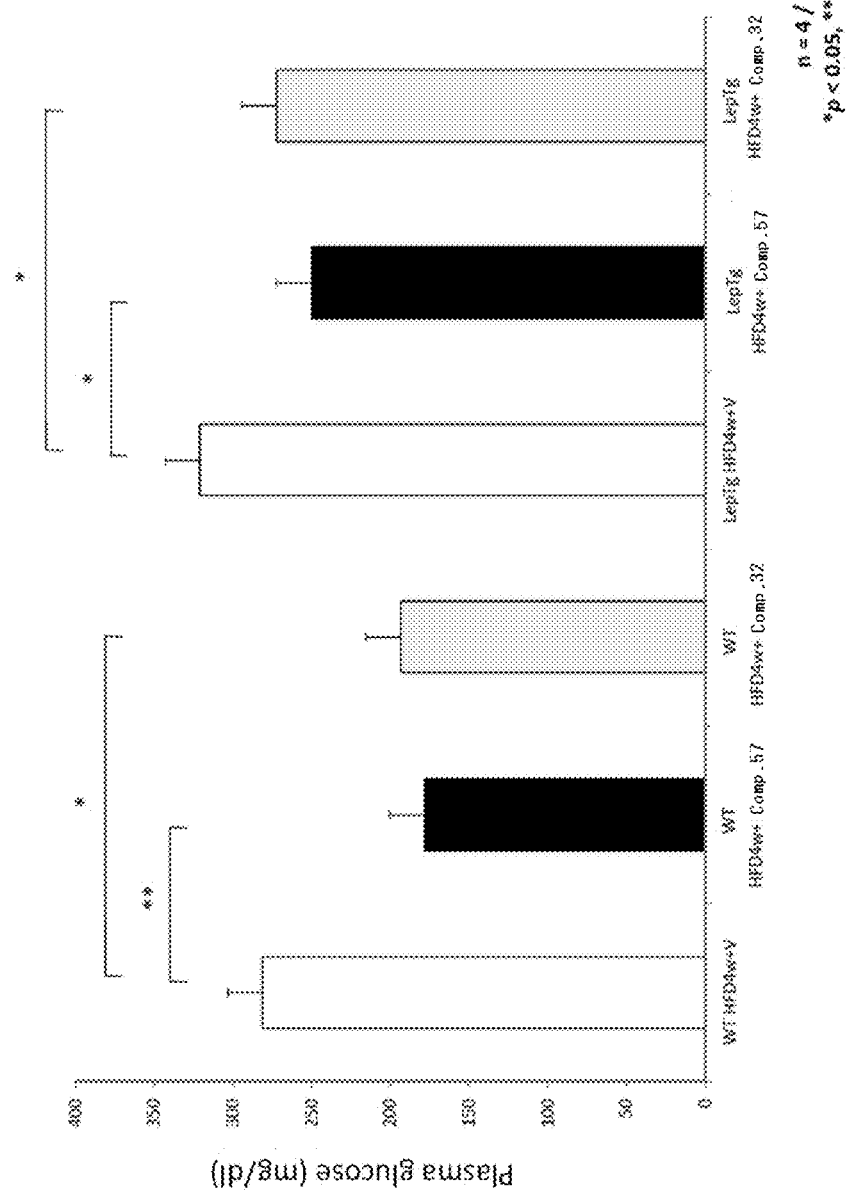
FIG. 17 shows the effects of Compounds 57 and 32 to improve glucose metabolism in the mice having diet-induced obesity.
Figure 18:
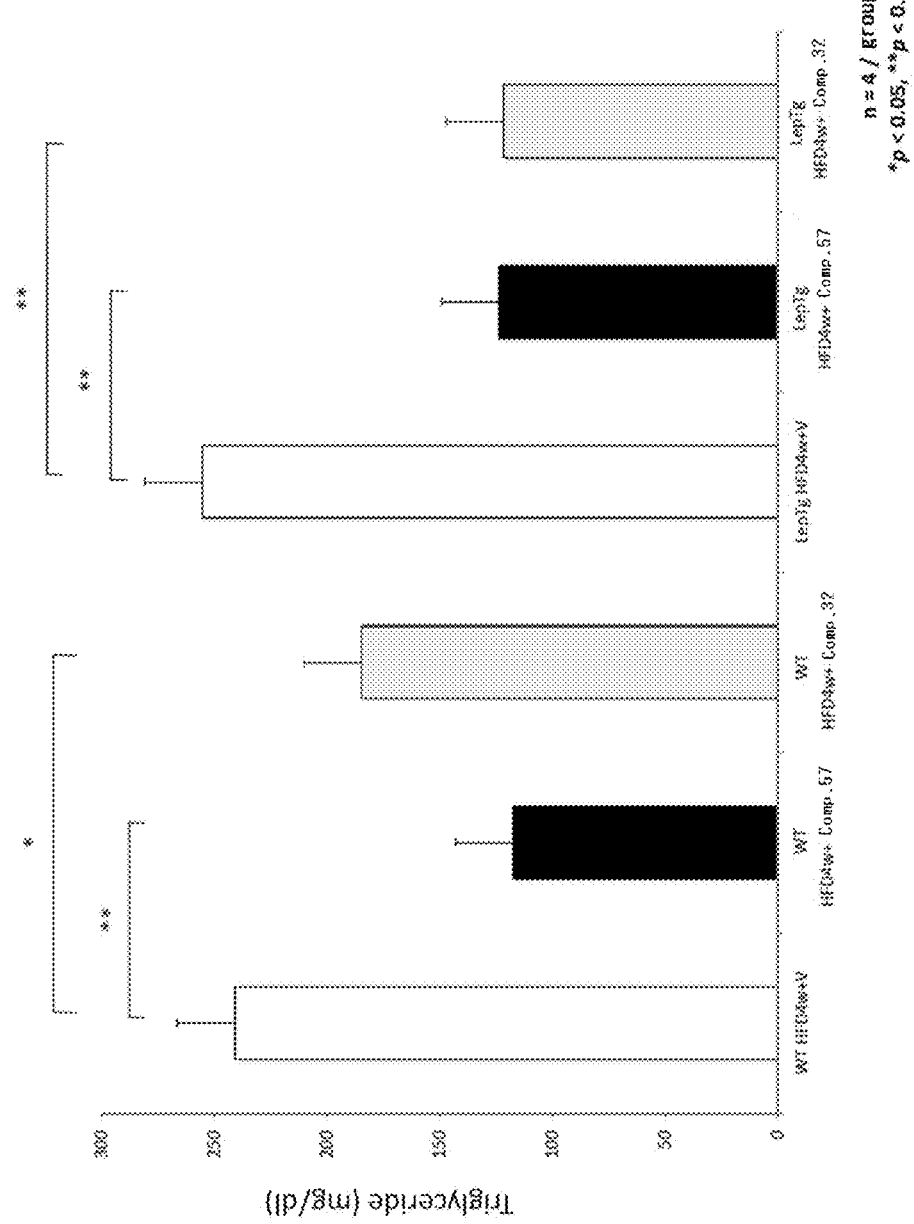
FIG. 18 shows the effects of Compounds 57 and 32 to improve lipid metabolism in the mice having diet-induced obesity.

When Compound 57 or 32 was administered to the wild type mice and the transgenic mice in which obesity was caused by the four-week high fat diet, their body weight was decreased in spite of the continued high fat diet (FIG. 13). The weight loss was more remarkable in the transgenic mice than in the wild type mice. The food intake significantly decreased in the wild type mice administered with Compound 57 and the transgenic mice administered with Compound 57 or 32 (FIG. 14). The weight of the adipose tissues significantly decreased in the transgenic mice administered with Compound 57 or 32 (FIG. 15). The liver weight, an indicator of steatosis, decreased only in the transgenic mice administered with Compound 57 (FIG. 16). The blood levels of glucose and triglyceride decreased in the both of the wild type mice and the transgenic mice when they were administered with Compound 57 or 32 (FIGS. 17 and 18).

In Test Example 4 the effects of Compounds 57 and 32 in the mice having obesity were tested. According to the results of Test Example 1, the mice are thought to have leptin resistance. In this study Compound 57 decreased the body weight, the food intake, the weight of the adipose tissues, the liver weight, and the plasma levels of glucose and triglyceride, and Compound 32 decreased the body weight, the food intake, the weight of the adipose tissues, and the plasma levels of glucose and triglyceride. The results indicate that the compounds not only prevent the development of leptin resistance, but improve leptin resistance that has developed already.

Test Example 5: Analysis of Effects of Compounds 32 and 57 to Improve Metabolism in Wild Type Rats Under a High Fat Diet Condition Eight-week old male wild type rats were divided into four treatment groups: "standard diet (SD)+vehicle (V)", "60% high fat diet (HFD)+vehicle", "60% high fat diet+Compound 57", and "60% high fat diet+Compound 32". The rats were kept for four weeks with ad libitum feeding, and the body weight of the rats was measured. The vehicle, Compound 32 and Compound 57 were administered to the rats by intraperitoneal injection once a day. The each dosage of Compounds 32 and 57 was 20 mg/kg/day. After the four weeks the rats were sacrificed, blood was collected, and the plasma levels of glucose and insulin were measured (n=5 for each group).

Figure 19:
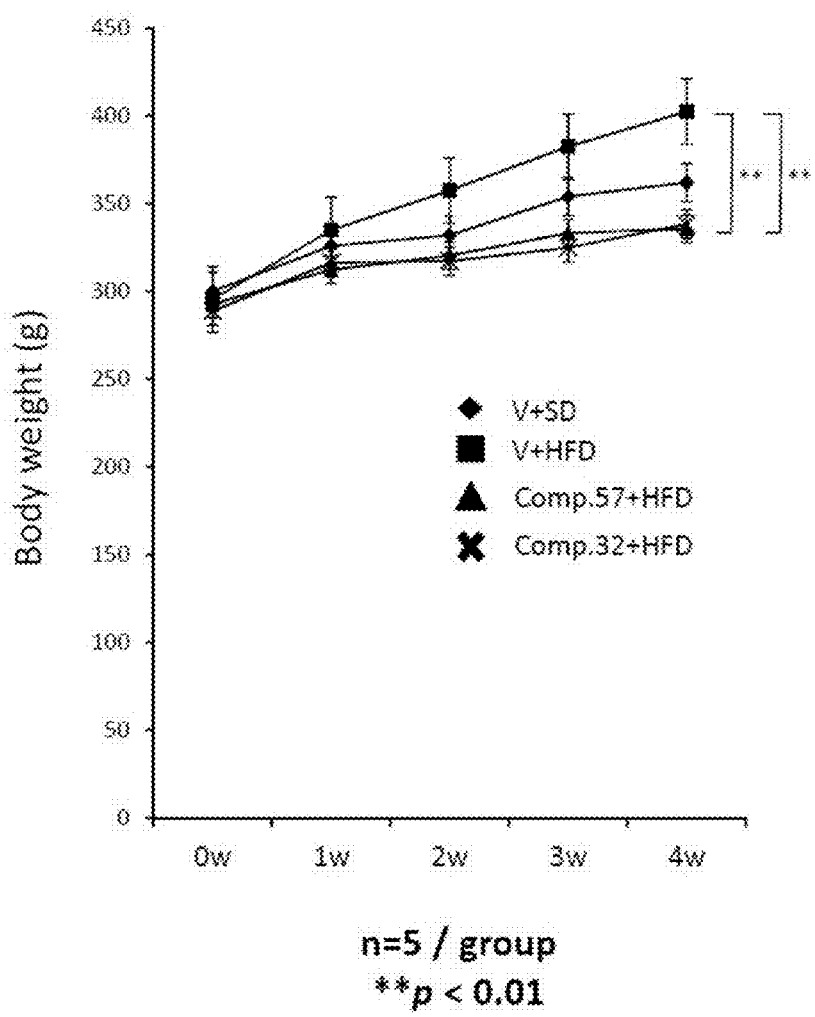
FIG. 19 shows the effects of Compounds 57 and 32 to suppress the weight gain in the wild type rats under the high fat diet condition.
Figure 20:
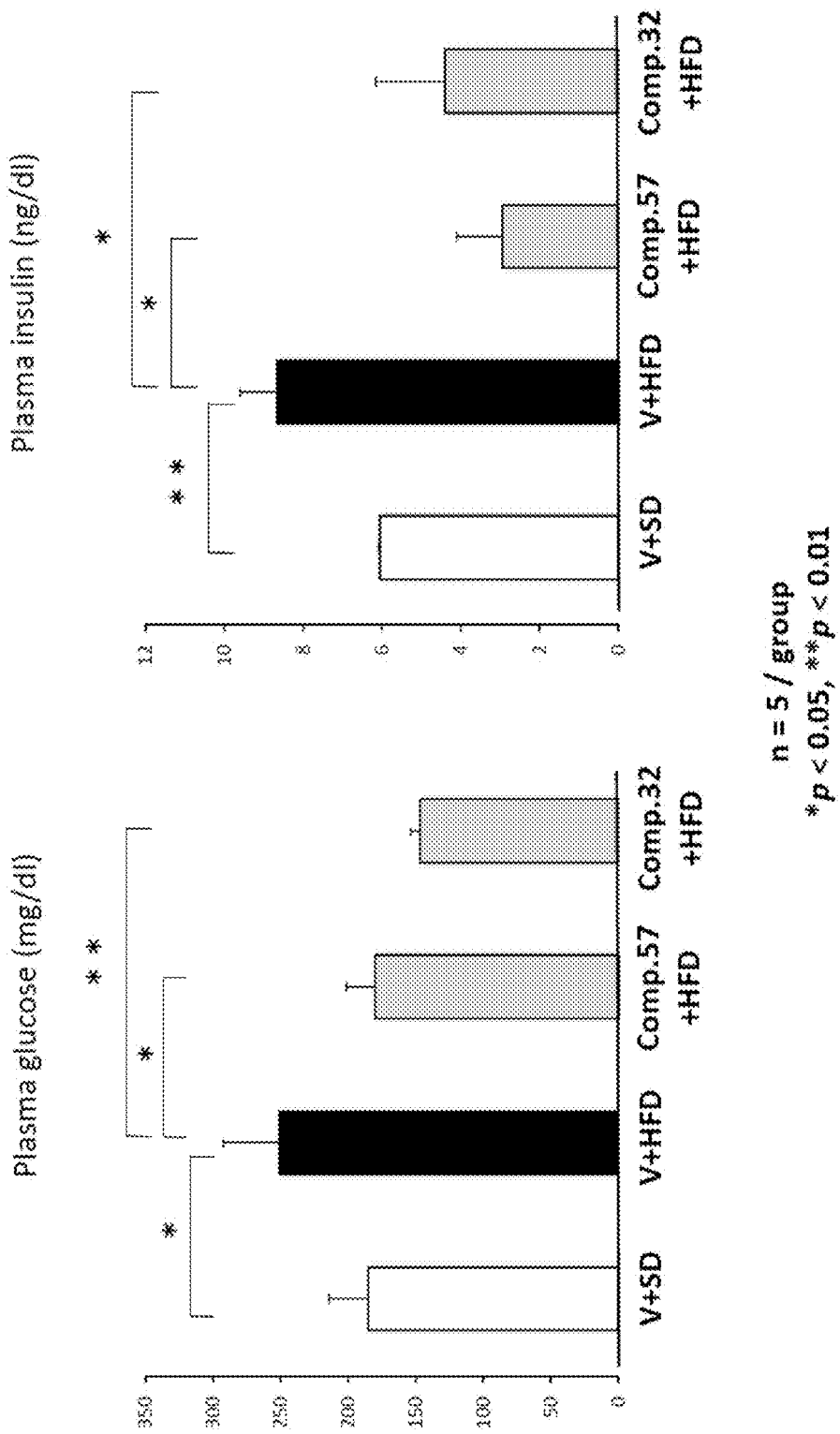
FIG. 20 shows the effects of Compounds 57 and 32 to improve insulin resistance in the wild type rats under the high fat diet condition.

The body weight increased more remarkably in the wild type rats fed with the high fat diet than in those fed with the standard diet (FIG. 19). The weight gain caused by the high fat diet was not observed in the wild type rats administered with Compound 57 or 32. Regarding glucose metabolism, the random plasma glucose levels and the plasma insulin levels increased in the wild type rats fed with the high fat diet, but did not increase when administered with Compound 57 or 32 (FIG. 20).

The high fat diet increased the body weight and the plasma levels of glucose and insulin in the wild type rats, as seen in the wild type mice. The results suggest that leptin resistance was induced in the rats as in the mice. Compound 57 or 32 suppressed the increases also in the rats to the levels as low as those of the rats fed with the standard diet, in which no leptin resistance developed. The results mean that the compounds prevent development of leptin resistance also in rats.

Test Example 6: Analysis of effects of Compounds 32 and 57 to improve metabolism in leptin-deficient Lepmkyo/Lepmkyo rats Lepmkyo/Lepmkyo rats cannot produce leptin due to a mutation in the leptin gene (Aizawa-Abe et al. Physiol Genomics 45: 786-793, 2013, prepared in Institute of Laboratory Animals, Graduate School of Medicine, Kyoto University). Eight-week old male Lepmkyo/Lepmkyo rats were divided into three treatment groups: "Vehicle (V)", "Compound 57", and "Compound 32". The rats were kept for four weeks with ad libitum feeding of standard diet, and the body weight of the rats were measured. The vehicle, Compound 57, and Compound 32 were administered to the rats by intraperitoneal injection once a day. The each dosage of Compounds 57 and 32 was 20 mg/kg/day. After the four weeks the rats were sacrificed, blood was collected, and the plasma levels of glucose and insulin were measured (n =5 for each group).

Figure 21:
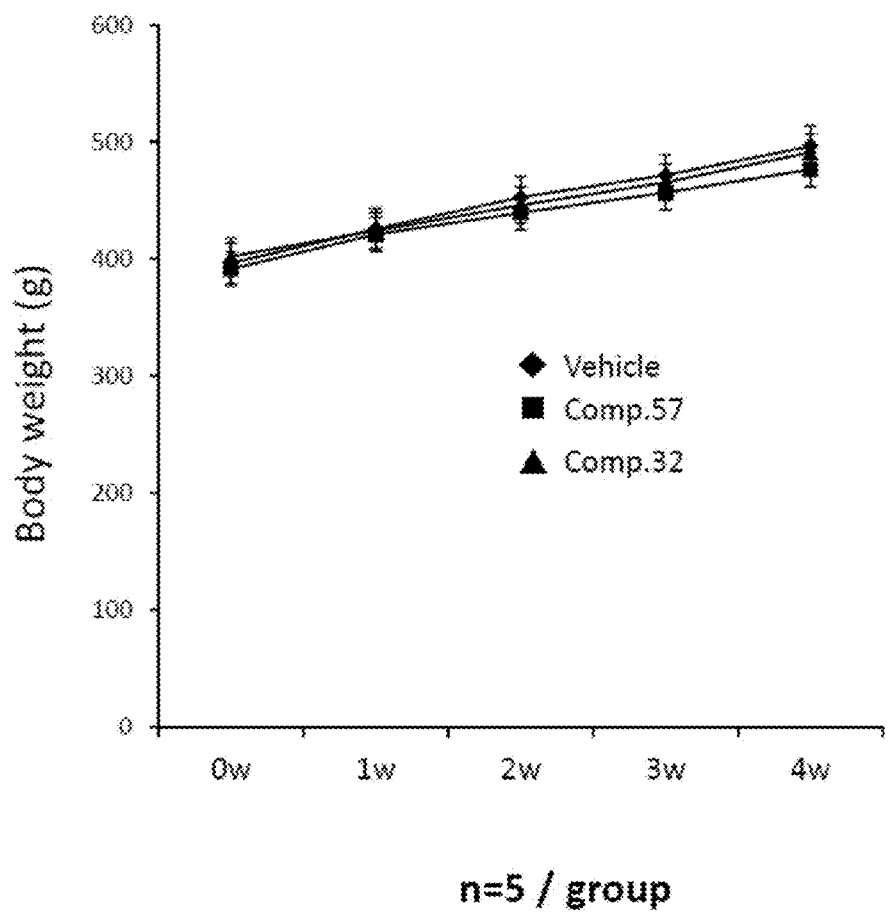
FIG. 21 shows the effects of Compounds 57 and 32 on the body weight in the $Lep^{mkyo}/Lep^{mkyo}$ rats.
Figure 22:
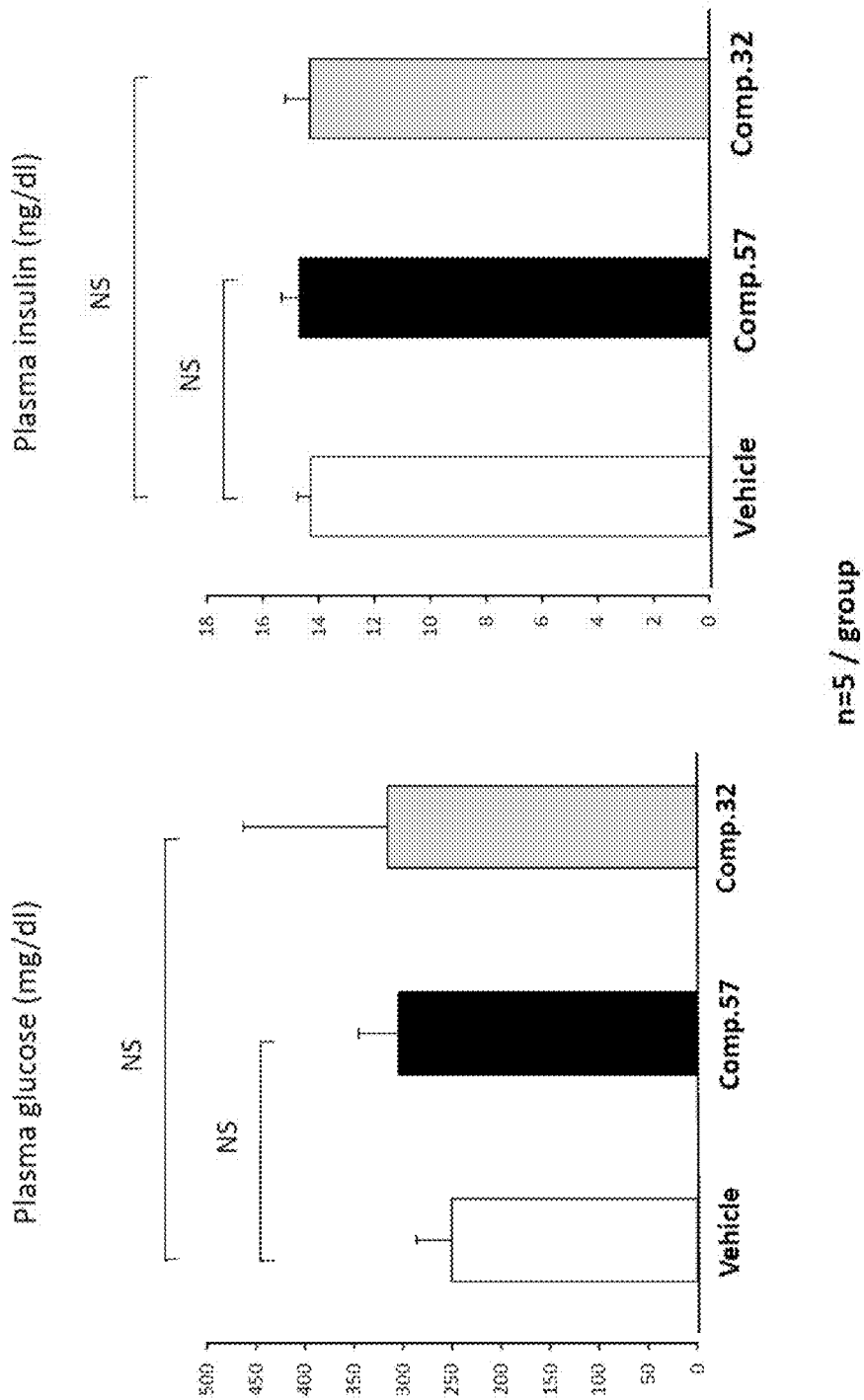
FIG. 22 shows the effects of Compounds 57 and 32 on insulin resistance in the $Lep^{mkyo}/Lep^{mkyo}$ rats.

No difference in the body weight was found between the $Lep^{mkyo}/Lep^{mkyo}$ rats administered with Compound 57 or 32 and the rats administered with the vehicle (FIG. 21). Regarding glucose metabolism, the random plasma glucose levels and the plasma insulin did not change in the rats administered with Compound 57 or 32 (FIG. 22).

In Test Example 6 the effects of Compounds 57 and 32 in the absence of leptin were tested. Compounds 57 and 32 did not change the body weight and the plasma levels of glucose and insulin. The results suggest that in Test Example 5 Compounds 57 and 32 suppressed the increase of the parameters such as the body weight in a leptin-dependent manner.

Test Example 7: Analysis of Effects of Compounds 32 and 57 to Improve Metabolism in Seipin KO Rats, a Model of Generalized Lipodystrophy Seipin KO rats have a mutation in the Seipin gene, the causative gene of human generalized lipodystrophy, and are used as a model of generalized lipodystrophy. The rats have substantially no white adipocyte and thus cannot produce leptin. The rats were prepared in Department of Endocrinology and Metabolism, Kyoto University. Eight-week old male Seipin KO rats were divided into three treatment groups: "Vehicle (V)", "Compound 57", and "Compound 32". The rats were kept for four weeks with ad libitum feeding of standard diet, and the body weight of the rats were measured. The vehicle, Compound 57, and Compound 32 were administered to the rats by intraperitoneal injection once a day. The each dosage of Compounds 57 and 32 was 20 mg/kg/day. After the four weeks the rats were sacrificed, blood was collected, and the plasma levels of glucose and insulin were measured (n=3 for each group).

Figure 23:
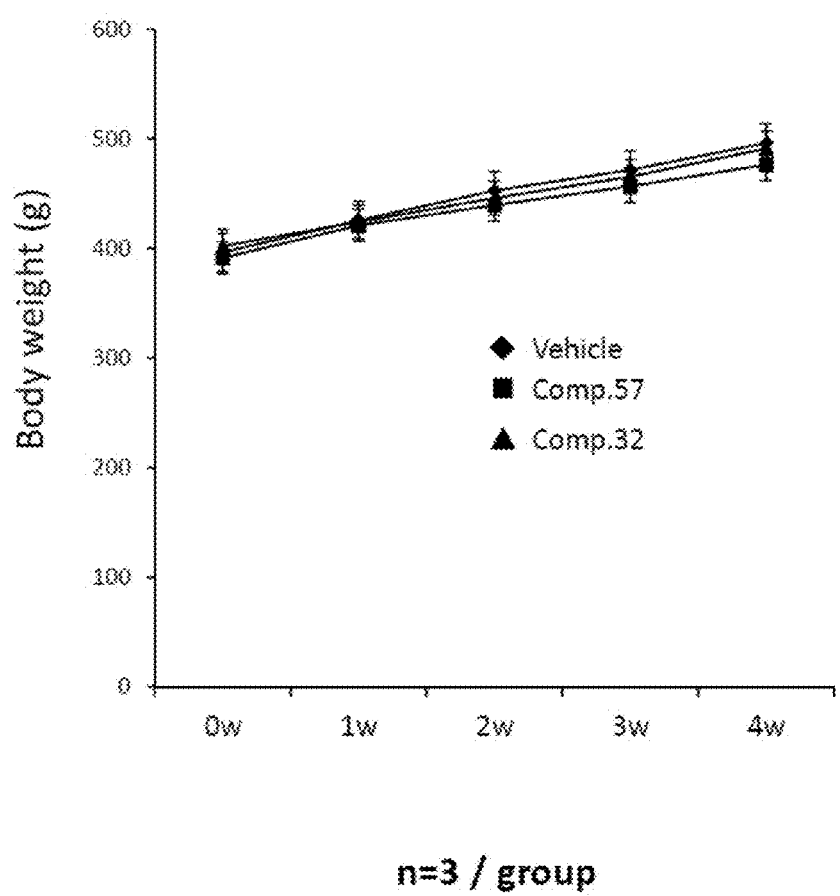
FIG. 23 shows the effects of Compounds 57 and 32 on the body weight in the rats of the lipodystrophy model.
Figure 24:
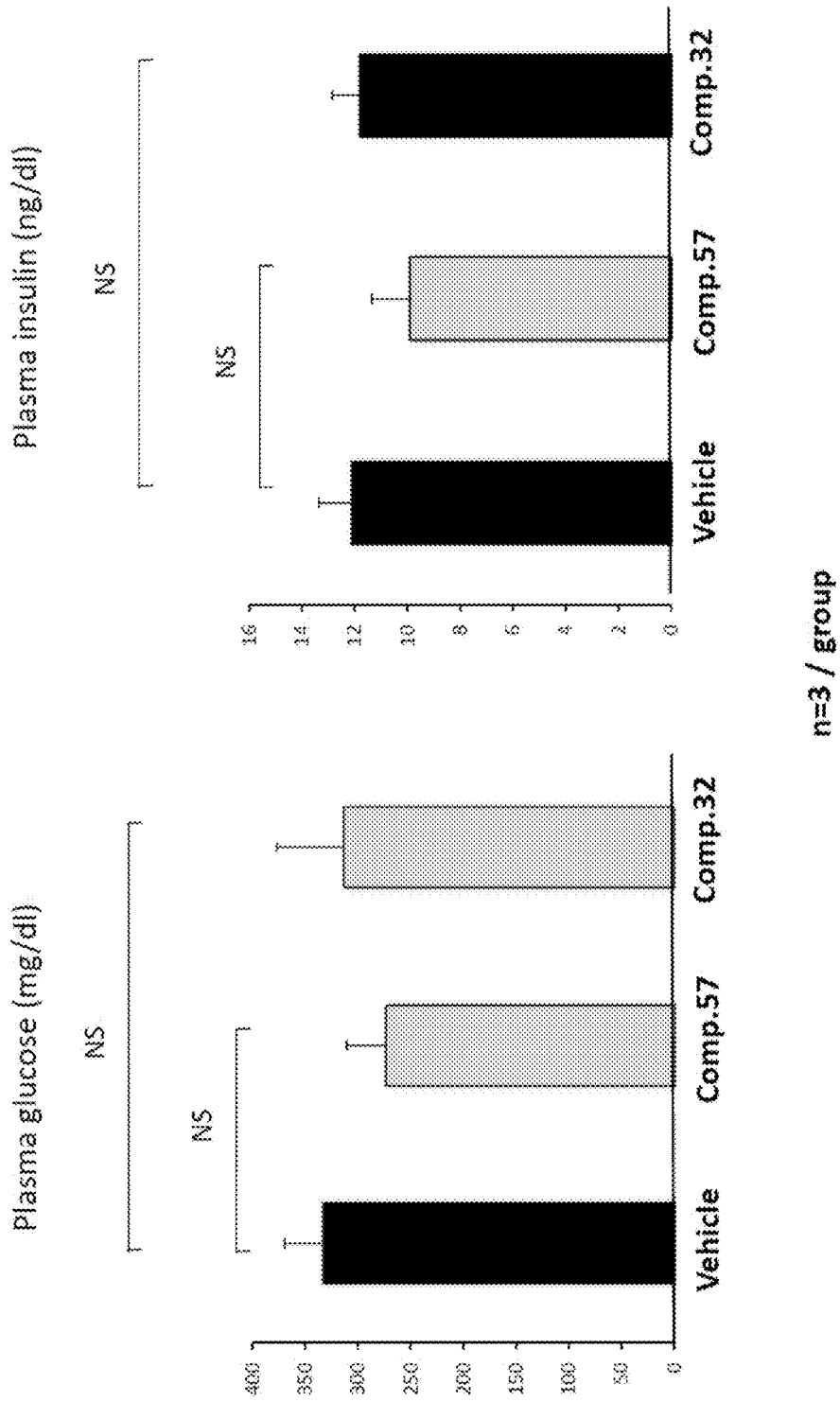
FIG. 24 shows the effects of Compounds 57 and 32 on insulin resistance in the rats of the lipodystrophy model.

The body weight did not change in the Seipin KO rats administered with Compound 57 or 32 (FIG. 23). Regarding glucose metabolism, the random plasma glucose levels and the plasma insulin did not change in the rats administered with Compound 57 or 32 (FIG. 24).

In Test Example 7, like in Test Example 6, the effects of Compounds 57 and 32 in the absence of leptin were tested. Compounds 57 and 32 caused no change in the body weight and the plasma levels of glucose and insulin. The results suggest that in Test Example 5 Compounds 57 and 32 suppressed the increase of the parameters such as the body weight in a leptin-dependent manner.

Test Example 8: Analysis of effects of Compounds 32 and 57 to improve metabolism in rats having diet-induced obesity caused by a high fat diet Eight-week old male wild type rats were divided into two groups (n =5 and 15) and kept for four weeks under a standard diet (SD) or a high fat diet (HFD) condition. All the rats fed with the standard diet for the four weeks were assigned to the group "vehicle (V)" and fed with the standard diet for further four weeks, and then the body weight of the rats was measured. The rats fed with the high fat diet for the four weeks were divided into three groups: "vehicle", "Compound 57", and "Compound 32", and fed with the high fat diet for further four weeks, and then the body weight of the rats was measured. The vehicle, Compound 57, and Compound 32 were administered to the rats by intraperitoneal injection once a day. The each dosage of Compounds 57 and 32 was 20 mg/kg/day. Finally the rats were sacrificed, blood, epididymal adipose tissues, and the liver were collected, and the weight of the adipose tissues, the liver weight, and the plasma levels of glucose, insulin, total cholesterol, triglyceride, and nonesterified fatty acid were measured (n =5 for each group).

Figure 25:
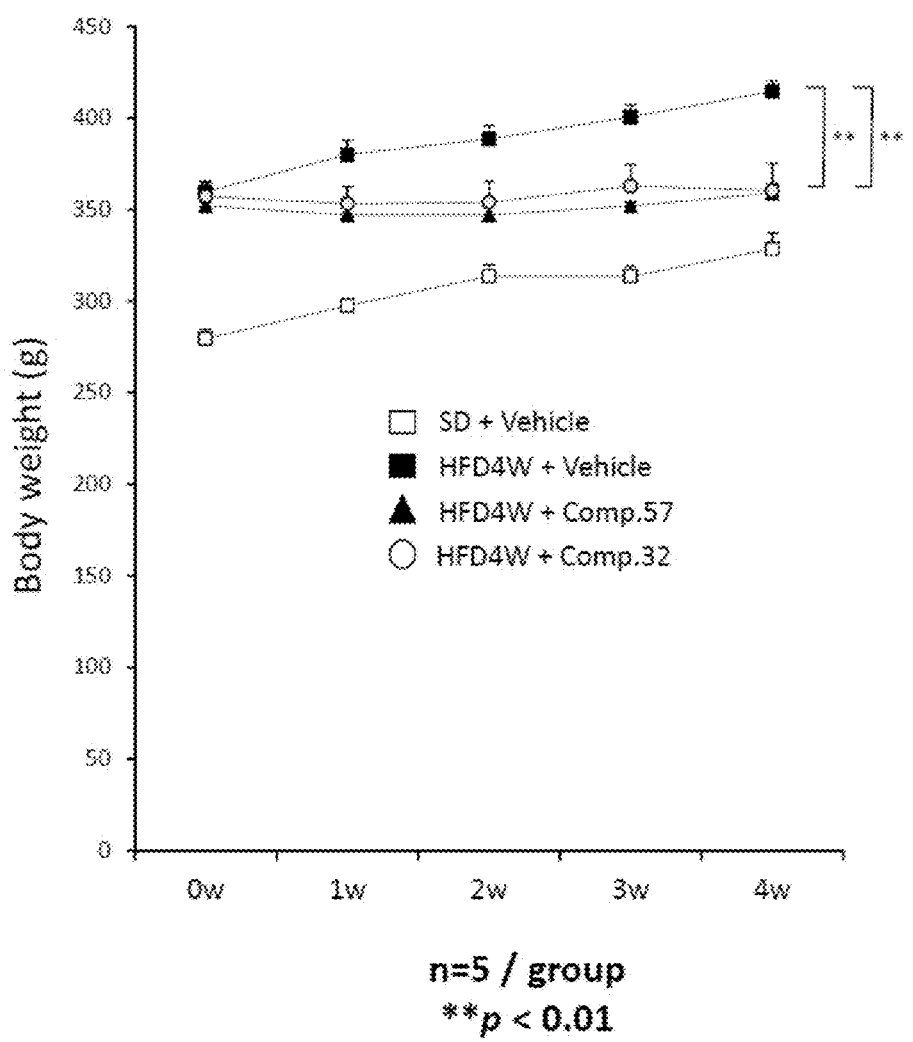
FIG. 25 shows the effects of Compounds 57 and 32 to decrease the body weight in the rats having diet-induced obesity.
Figure 26:
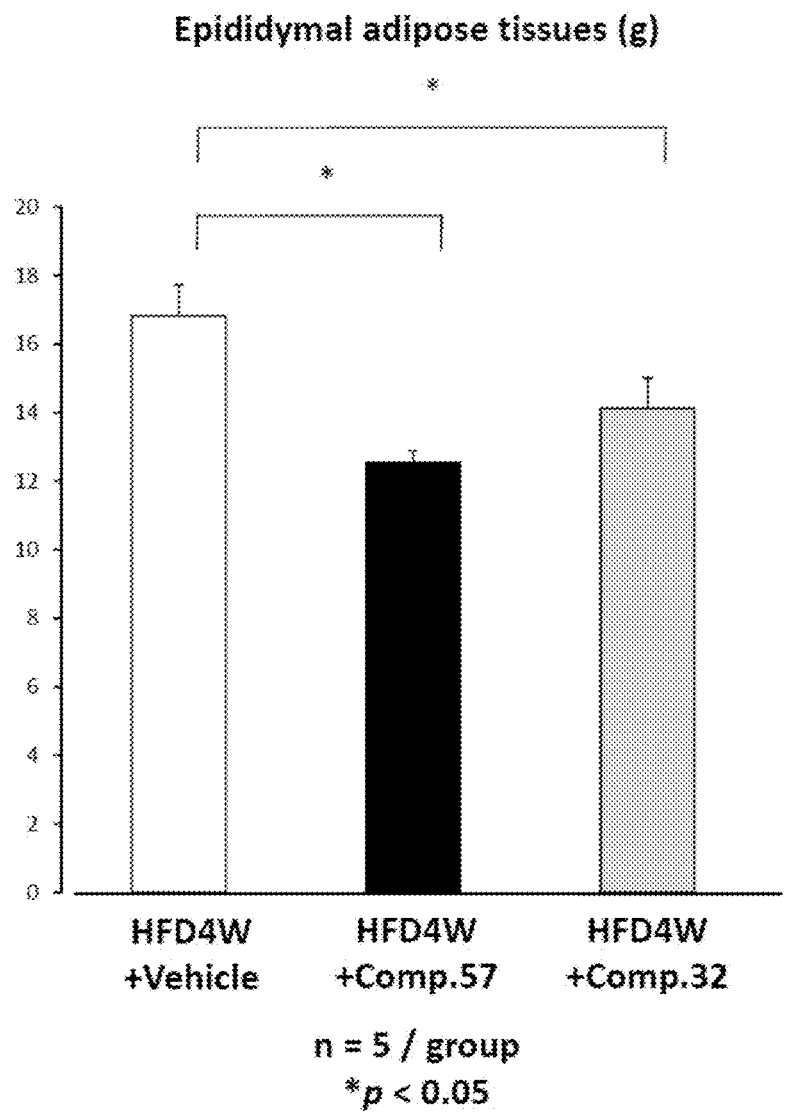
FIG. 26 shows the effects of Compounds 57 and 32 to decrease the weight of the adipose tissues in the rats having diet-induced obesity.
Figure 27:
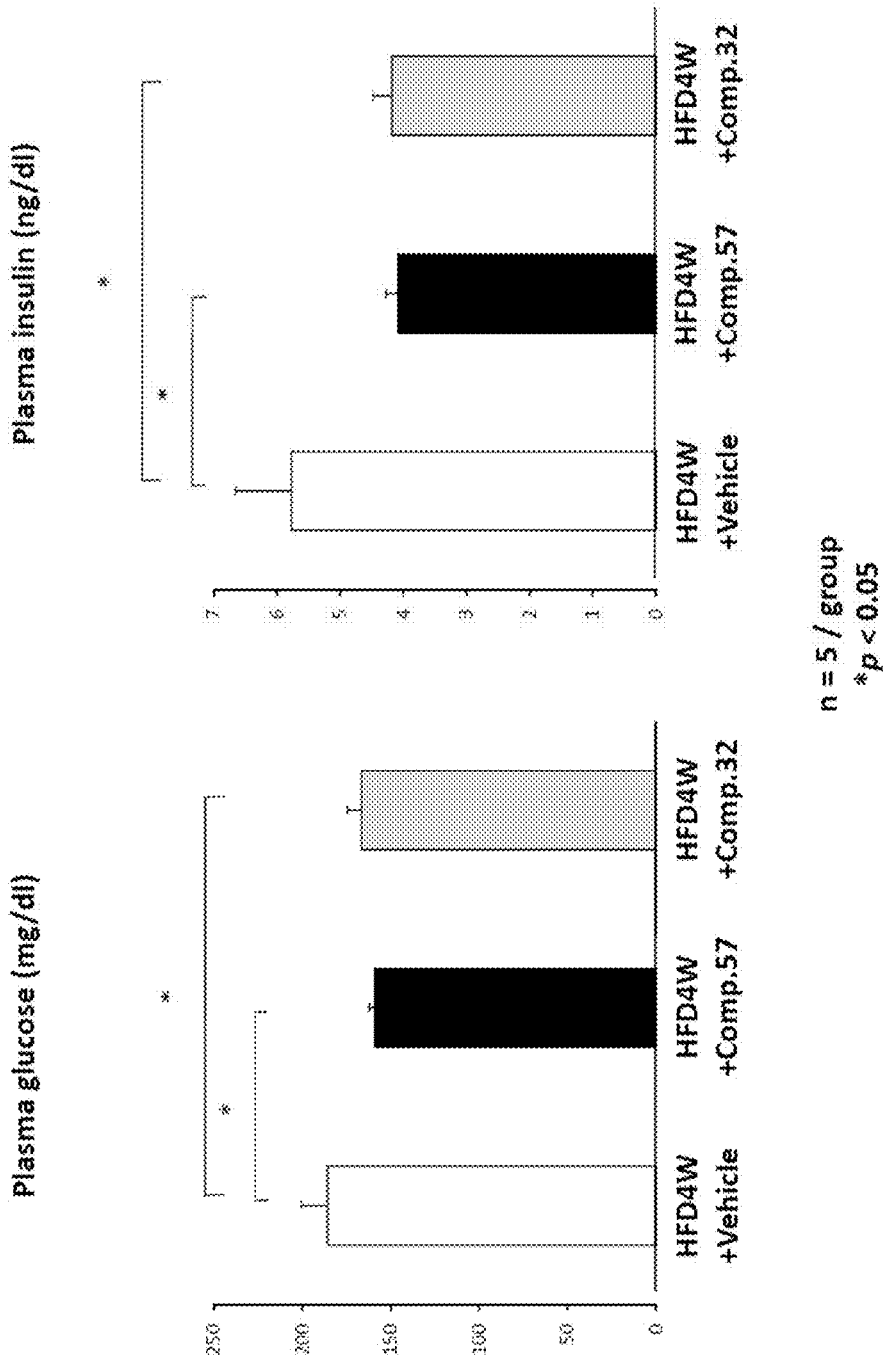
FIG. 27 shows the effects of Compounds 57 and 32 to improve insulin resistance in the rats having diet-induced obesity.
Figure 28:
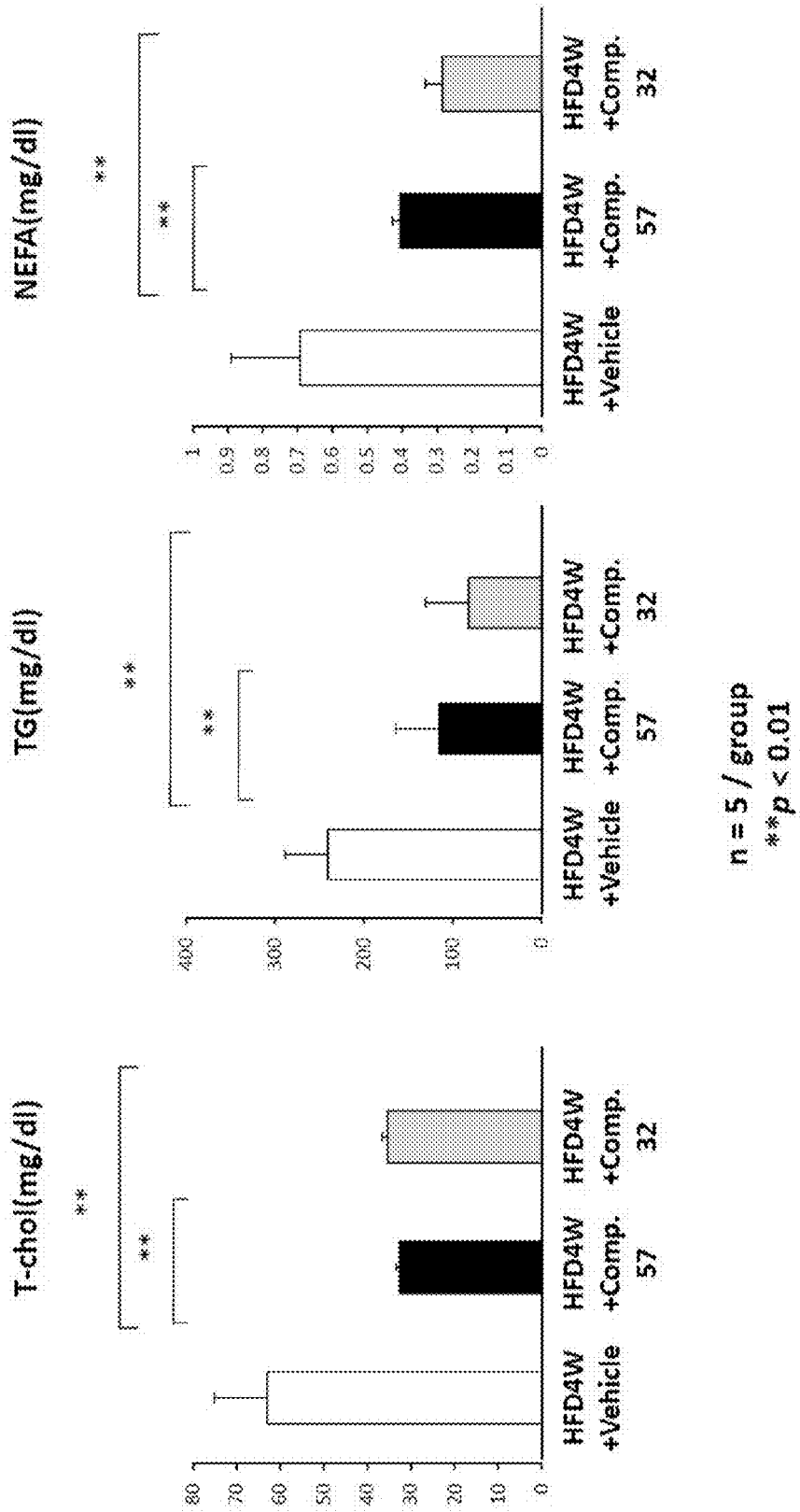
FIG. 28 shows the effects of Compounds 57 and 32 to improve lipid metabolism in the rats having diet-induced obesity.

When Compound 57 or 32 was administered to the wild type rats in which obesity was caused by the four-week high fat diet, their body weight was decreased in spite of the continued high fat diet (FIG. 25). The weight of the adipose tissues increased in the rats fed with the high fat diet, and decreased in the rats administered with Compound or 32 (FIG. 26). Regarding glucose metabolism, the plasma levels of glucose and insulin increased in the rats fed with the high fat diet, and decreased in the rats administered with Compound 57 or 32 (FIG. 27). Regarding lipid metabolism, the plasma levels of total cholesterol, triglyceride, and nonesterified fatty acid decreased in the rats administered with Compound 57 or 32 (FIG. 28).

In Test Example 8 the effects of Compounds 57 and 32 in the rats having obesity were tested. According to the results of Test Example 5, the rats, as well as the mice in the preceding examples, are thought to have leptin resistance. In this study Compounds 57 and 32 decreased the body weight, the weight of the adipose tissues, and the plasma levels of glucose, insulin, total cholesterol, triglyceride, and nonesterified fatty acid. The results indicate that the compounds not only prevent development of leptin resistance, but improve leptin resistance that has developed already in rats as well as in mice.

INDUSTRIAL APPLICABILITY

The results of the pharmacological tests demonstrate that the compounds of the present invention, particularly Compounds 32 and 57 improve leptin resistance and thus useful for treating and/or preventing a disorder associated with leptin resistance.

The invention claimed is:

1. A method of reducing a body weight of a subject suffering from leptin resistance comprising administering to the subject an effective amount of a compound of formula (I):

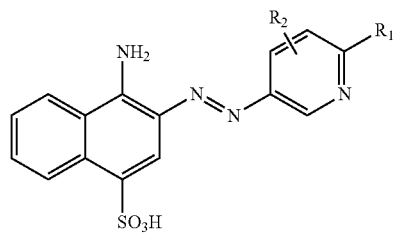

wherein: $R_1$ is phenyl or sulfur-containing heteroaryl, wherein the sulfur-containing heteroaryl is an aromatic group of from 3 to 12 carbon atoms and 1 to 4 sulfur atoms within the ring, and the phenyl or sulfur-containing heteroaryl may be substituted with 1 to 3 substituents independently selected from the group consisting of halo, hydroxy, alkyl, halo-substituted alkyl, alkoxy, hydroxy- or carboxy-substituted alkoxy, alkylthio, CHO, C(O)-alkyl, C(O)-alkylene-carboxyl, C(O)-alkylene-carboxy ester, cyano, and oxo, and $R_2$ is hydrogen, or an oxide, ester, pharmaceutically acceptable salt, or solvate thereof.

2. The method according to claim 1, wherein the subject is a human, a dog or a cat.

3. The method according to claim 1, wherein $R_1$ is, thiophenyl, benzothiophenyl, dibenzothiophenyl, or thianthrenyl which may be substituted with 1 to 3 substituents independently selected from the group consisting of halo, oxo, and alkyl.

4. The method according to claim 1, wherein $R_1$ is benzothiophenyl, dibenzothiophenyl, or thianthrenyl which may be substituted with 1 to 3 substituents independently selected from the group consisting of halo and alkyl.

5. The method according to claim 1, wherein $R_1$ is benzothiophenyl or dibenzothiophenyl which may be substituted with 1 to 3 substituents independently selected from the group consisting of halo and alkyl.

6. The method according to claim 1, wherein $R_1$ is dibenzothiophenyl which may be substituted with 1 to 3 substituents independently selected from the group consisting of halo and alkyl.

7. The method according to claim 1, wherein $R_1$ is phenyl which may be substituted with 1 to 3 substituents independently selected from the group consisting of halo, hydroxy, alkyl, halo-substituted alkyl, alkoxy, hydroxy- or carboxy-substituted alkoxy, alkylthio, CHO, C(O)-alkyl, C(O)-alkylene-carboxyl, C(O)-alkylene-carboxy ester, and cyano.

8. The method according to claim 1, wherein $R_1$ is phenyl which may be substituted with 1 to 3 substituents independently selected from the group consisting of halo, hydroxy, alkyl, halo-substituted alkyl, alkoxy, and alkylthio.

9. The method according to claim 1, wherein $R_1$ is phenyl which may be substituted with 1 to 3 substituents independently selected from the group consisting of halo and alkyl.

10. The method according to claim 1, wherein the compound is selected from the group consisting of
4-amino-3-(6-phenylpyridine-3-ylazo)naphthalene-1-sulfonic acid,
4-amino-3-(6-p-tolylpyridine-3-ylazo)naphthalene-1-sulfonic acid, 4-amino-3-(6-m-tolylpyridine-3-ylazo)naphthalene-1-sulfonic acid,
4-amino-3-(6-o-tolylpyridine-3-ylazo)naphthalene-1-sulfonic acid,
3-[6-(2-acetylphenyl)pyridine-3-ylazo]-4-aminonaphthalene-1-sulfonic acid,
3-[6-(3-acetylphenyl)pyridine-3-ylazo]-4-aminonaphthalene-1-sulfonic acid,
3-[6-(4-acetylphenyl)pyridine-3-ylazo]-4-aminonaphthalenesulfonic acid,
4-amino-3-[6-(2,4-dichlorophenyl)pyridine-3-ylazo]naphthalene-1-sulfonic acid,
4-amino-3-[6-(2-trifluoromethylphenyl)pyridine-3-ylazo]naphthalene-1-sulfonic acid,
4-amino-3-[6-(4-trifluoromethylphenyl)pyridine-3-ylazo]naphthalene-1-sulfonic acid,
4-amino-3-[6-(2-chlorophenyl)pyridine-3-ylazo]naphthalene-1-sulfonic acid,
4-amino-3-[6-(3-chlorophenyl)pyridine-3-ylazo]naphthalene-1-sulfonic acid,
4-amino-3-[6-(4-chlorophenyl)pyridine-3-ylazo]naphthalene-1-sulfonic acid,
4-amino-3-[6-(2-methoxyphenyl)pyridine-3-ylazo]naphthalene-1-sulfonic acid,
4-amino-3-[6-(4-methoxyphenyl)pyridine-3-ylazo]naphthalene-1-sulfonic acid,
4-amino-3-[6-(2-isopropoxyphenyl)pyridine-3-ylazo]naphthalene-1-sulfonic acid,
4-amino-3-[6-(4-isopropoxyphenyl)pyridine-3-ylazo]naphthalene-1-sulfonic acid,
4-amino-3-[6-(3-methoxyphenyl)pyridine-3-ylazo]naphthalene-1-sulfonic acid,
4-amino-3-[6-(2,3-dimethylphenyl)pyridine-3-ylazo]naphthalene-1-sulfonic acid,
4-amino-3-[6-(2,5-dimethylphenyl)pyridine-3-ylazo]naphthalene-1-sulfonic acid,
4-amino-3-[6-(3,5-dimethylphenyl)pyridine-3-ylazo]naphthalene-1-sulfonic acid,
4-amino-3-[6-(3-trifluoromethylphenyl)pyridine-3-ylazo]naphthalene-1-sulfonic acid,
methyl 4-{4-[5-(1-amino-4-sulfonaphthalene-2-ylazo)pyridine-2-yl]phenyl}-4-oxobutyrate,
4-amino-3-[6-(3-cyanophenyl)pyridine-3-ylazo]naphthalene-1-sulfonic acid,
4-amino-3-[6-(4-cyanophenyl)pyridine-3-ylazo]naphthalene-1-sulfonic acid,
4-amino-3-[6-(3,5-bistrifluoromethylphenyl)pyridine-3-ylazo]naphthalenesulfonic acid,
4-amino-3-[6-(2-propoxyphenyl)pyridine-3-ylazo]naphthalene-1-sulfonic acid,
4-amino-3-[6-(4-fluoro-2-methylphenyl)pyridine-3-ylazo]naphthalene-1-sulfonic acid,
4-amino-3-[6-(5-fluoro-2-propoxyphenyl)pyridine-3-ylazo]naphthalene-1-sulfonic acid,
4-amino-3-[6-(2-fluoro-6-propoxyphenyl)pyridine-3-ylazo]naphthalene-1-sulfonic acid,
4-amino-3-[6-(4-fluoro-2-propoxyphenyl)pyridine-3-ylazo]naphthalene-1-sulfonic acid,
4-amino-3-[6-(5-fluoro-2-methylphenyl)pyridine-3-ylazo]naphthalene-1-sulfonic acid,
4-amino-3-[6-(2-fluoro-5-methylphenyl)pyridine-3-ylazo]naphthalene-1-sulfonic acid,
4-amino-3-[6-(2-butoxyphenyl)pyridine-3-ylazo]naphthalene-1-sulfonic acid,
4-amino-3-[6-(2-hexyloxyphenyl)pyridine-3-ylazo]naphthalene-1-sulfonic acid,
4-amino-3-[6-(4-butylphenyl)pyridine-3-ylazo]naphthalene-1-sulfonic acid,
4-amino-3-[6-(2-hydroxyphenyl)pyridine-3-ylazo]naphthalene-1-sulfonic acid,
4-amino-3-{6-[2-(6-hydroxyhexyloxy)phenyl]pyridine-3-ylazo}naphthalene-1-sulfonic acid,
4-{2-[5-(1-amino-4-sulfonaphthalene-2-ylazo)pyridine-2-yl]phenoxy}butyric acid,
4-amino-3-{6-[2-(3-hydroxypropoxy)phenyl]pyridine-3-ylazo}naphthalene-1-sulfonic acid,
4-amino-3-[6-(2-isobutoxyphenyl)pyridine-3-ylazo]naphthalene-1-sulfonic acid,
4-amino-3-[6-(5-chloro-2-hydroxyphenyl)pyridine-3-ylazo]naphthalene-1-sulfonic acid,
4-amino-3-[6-(2,6-dimethylphenyl)pyridine-3-ylazo]naphthalene-1-sulfonic acid,
4-amino-3-[6-(3-formyl-2-isopropoxy-5-methylphenyl)pyridine-3-ylazo]naphthalene-1-sulfonic acid,
4-amino-3-[6-(3-formyl-2-butoxy-5-methylphenyl)pyridine-3-ylazo]naphthalene-1-sulfonic acid,
4-amino-3-(6-thiophene-2-ylpyridine-3-ylazo)naphthalene-1-sulfonic acid,
4-amino-3-(6-thiophene-3-ylpyridine-3-ylazo)naphthalene-1-sulfonic acid,
4-amino-3-(6-dibenzothiophene-4-ylpyridine-3-ylazo)naphthalene-1-sulfonic acid,
4-amino-3-(6-benzo[b]thiophene-3-ylpyridine-3-ylazo)naphthalene-1-sulfonic acid,
4-amino-3-(6-dibenzothiophene-4-ylpyridine-3-ylazo)naphthalene-1-sulfonic acid potassium salt
4-amino-3-[6-(5,5-dioxo-5H-5λ6-dibenzothiophene-4-yl)pyridine-3-ylazo]naphthalene-1-sulfonic acid,
4-amino-3-(6-thianthrene-1-ylpyridine-3-ylazo)naphthalene-1-sulfonic acid,
4-amino-3-[6-(2-butoxy-3-ethoxy-5-formylphenyl)pyridine-3-ylazo]naphthalene-1-sulfonic acid, and
4-amino-3-[6-(2-ethoxy-3-formyl-5-methylphenyl)pyridine-3-ylazo]naphthalene-1-sulfonic acid.

11. The method according to claim 1, wherein the compound is 4-amino-3[6-(4-fluoro-2-methylphenyppyridine-3-ylazo]naphthalene-1-sulfonic acid.

12. The method according to claim 1, wherein the compound is 4-amino-3-(6-dibenzothiophene-4-ylpyridine-3-ylazo)naphthalene-1-sulfonic acid.

13. A method of treating a disorder associated with leptin resistance selected from a metabolic disorder, obesity, hyperphagia, steatosis, diabetes, and dyslipidemia in a subject suffering from leptin resistance by reducing the body weight of the subject in accordance with the method of claim 1.

14. A method of increasing lipid metabolism and/or treating steatosis in a subject suffering from leptin resistance by reducing the body weight of the subject in accordance with the method of claim 1.

15. A method of decreasing a weight of an adipose tissue in a subject suffering from leptin resistance comprising administering to the subject an effective amount of a compound of formula (I):

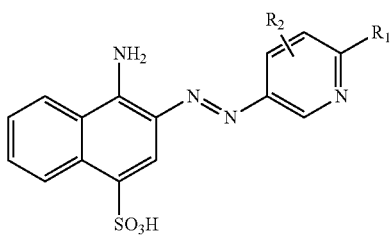

wherein $R_1$ is phenyl or sulfur-containing heteroaryl, wherein the sulfur-containing heteroaryl is an aromatic group of from 3 to 12 carbon atoms and 1 to 4 sulfur atoms within the ring, and the phenyl or sulfur-containing heteroaryl may be substituted with 1 to 3 substituents independently selected from the group consisting of halo, hydroxy, alkyl, halo-substituted alkyl, alkoxy, hydroxy- or carboxy-substituted alkoxy, alkylthio, CHO, C(O)-alkyl, C(O)-alkylene-carboxyl, C(O)-alkylene-carboxy ester, cyano, and oxo, and $R_2$ is hydrogen, or an oxide, ester, pharmaceutically acceptable salt, or solvate thereof.

16. A method of treating a disorder associated with leptin resistance selected from a metabolic disorder, obesity, hyperphagia, steatosis, diabetes, and dyslipidemia in a subject suffering from leptin resistance by decreasing a weight of an adipose tissue in the subject in accordance with the method of claim 15.

17. A method of decreasing insulin resistance in a subject suffering from leptin resistance comprising administering to the subject an effective amount of a compound of formula (I):

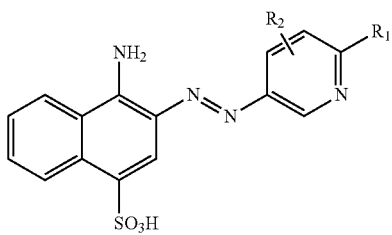

wherein $R_1$ is phenyl or sulfur-containing heteroaryl, wherein the sulfur-containing heteroaryl is an aromatic group of from 3 to 12 carbon atoms and 1 to 4 sulfur atoms within the ring, and the phenyl or sulfur-containing heteroaryl may be substituted with 1 to 3 substituents independently selected from the group consisting of halo, hydroxy, alkyl, halo-substituted alkyl, alkoxy, hydroxy- or carboxy-substituted alkoxy, alkylthio, CHO, C(O)-alkyl, C(O)-alkylene-carboxyl, C(O)-alkylene-carboxy ester, cyano, and oxo, and $R_2$ is hydrogen, or an oxide, ester, pharmaceutically acceptable salt, or solvate thereof.

18. A method of treating a disorder associated with leptin resistance selected from a metabolic disorder, obesity, hyperphagia, steatosis, diabetes, and dyslipidemia in a subject suffering from leptin resistance by decreasing insulin resistance in the subject in accordance with the method of claim 17.

19. A method of increasing lipid metabolism in a subject suffering from leptin resistance comprising administering to the subject an effective amount of a compound of formula (I):

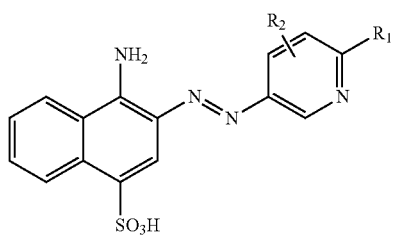

wherein $R_1$ is phenyl or sulfur-containing heteroaryl, wherein the sulfur-containing heteroaryl is an aromatic group of from 3 to 12 carbon atoms and 1 to 4 sulfur atoms within the ring, and the phenyl or sulfur-containing heteroaryl may be substituted with 1 to 3 substituents independently selected from the group consisting of halo, hydroxy, alkyl, halo-substituted alkyl, alkoxy, hydroxy- or carboxy-substituted alkoxy, alkylthio, CHO, C(O)-alkyl, C(O)-alkylene-carboxyl, C(O)-alkylene-carboxy ester, cyano, and oxo, and $R_2$ is hydrogen, or an oxide, ester, pharmaceutically acceptable salt, or solvate thereof.

20. A method of treating a disorder associated with leptin resistance selected from a metabolic disorder, obesity, hyperphagia, steatosis, diabetes, and dyslipidemia in a subject suffering from leptin resistance by increasing lipid metabolism in the subject in accordance with the method of claim 19.

* * * * *